(12) United States Patent
Cowden et al.

(10) Patent No.: US 11,952,607 B2
(45) Date of Patent: Apr. 9, 2024

(54) MICROORGANISMS AND METHODS FOR IMPROVED BIOLOGICAL PRODUCTION OF ETHYLENE GLYCOL

(71) Applicant: LanzaTech, Inc., Skokie, IL (US)

(72) Inventors: Zachary Robert Cowden, San Diego, CA (US); Ching Leang, Evanston, IL (US); Michael Koepke, Chicago, IL (US); Rasmus Overgaard Jensen, Evanston, IL (US); Alexander Paul Mueller, Skokie, IL (US)

(73) Assignee: LanzaTech, Inc., Skokie, IL (US)

( * ) Notice: Subject to any disclaimer, the term of this patent is extended or adjusted under 35 U.S.C. 154(b) by 0 days.

(21) Appl. No.: 17/817,766

(22) Filed: Aug. 5, 2022

(65) Prior Publication Data
US 2023/0065430 A1  Mar. 2, 2023

Related U.S. Application Data

(60) Provisional application No. 63/261,185, filed on Sep. 14, 2021, provisional application No. 63/260,054, filed on Aug. 6, 2021.

(51) Int. Cl.
| | | |
|---|---|---|
| *C12N 15/74* | (2006.01) | |
| *C12N 1/20* | (2006.01) | |
| *C12N 9/02* | (2006.01) | |
| *C12N 9/10* | (2006.01) | |
| *C12N 9/88* | (2006.01) | |
| *C12N 15/52* | (2006.01) | |
| *C12P 7/18* | (2006.01) | |
| *C12R 1/145* | (2006.01) | |

(52) U.S. Cl.
CPC .................. *C12P 7/18* (2013.01); *C12N 1/20* (2013.01); *C12N 9/0008* (2013.01); *C12N 9/1025* (2013.01); *C12N 9/1096* (2013.01); *C12N 9/88* (2013.01); *C12N 15/52* (2013.01); *C12R 2001/145* (2021.05); *C12Y 102/01003* (2013.01); *C12Y 102/01021* (2013.01); *C12Y 203/03001* (2013.01); *C12Y 206/01044* (2013.01); *C12Y 401/03001* (2013.01)

(58) Field of Classification Search
CPC ........... C12P 7/18; C12N 1/20; C12N 9/0008; C12N 9/1025; C12N 9/1096; C12N 9/88; C12N 15/52; C12R 2001/145; C12Y 102/01003; C12Y 102/01021; C12Y 203/03001; C12Y 206/01044; C12Y 401/03001
USPC ....................................................... 435/158
See application file for complete search history.

(56) References Cited

U.S. PATENT DOCUMENTS

| | | | |
|---|---|---|---|
| 2,218,234 | A | 10/1940 | Fisher |
| 5,552,023 | A | 9/1996 | Zhou |
| 5,593,886 | A | 1/1997 | Gaddy |
| 6,368,819 | B1 | 4/2002 | Gaddy |
| 7,704,723 | B2 | 4/2010 | Huhnke |
| 7,951,980 | B2 | 5/2011 | Reimann |
| 7,972,824 | B2 | 7/2011 | Simpson |
| 8,222,013 | B2 | 7/2012 | Simpson |
| 8,293,509 | B2 | 10/2012 | Simpson |
| 8,323,950 | B2 | 12/2012 | Burk |
| 8,445,244 | B2 | 5/2013 | Burgard |
| 8,658,408 | B2 | 2/2014 | Simpson |
| 8,658,845 | B2 | 2/2014 | Oroskar |
| 8,900,836 | B2 | 12/2014 | Simpson |
| 9,068,202 | B2 | 6/2015 | Tran |
| 9,284,564 | B2 | 3/2016 | Mueller |
| 9,347,076 | B2 | 5/2016 | Liew |
| 9,359,611 | B2 | 6/2016 | Koepke |
| 9,410,130 | B2 | 8/2016 | Koepke |
| 9,738,875 | B2 | 8/2017 | Koepke |
| 9,890,384 | B2 | 2/2018 | Mueller |
| 9,920,335 | B2 | 3/2018 | Medoff |
| 9,994,878 | B2 | 6/2018 | Koepke |
| 10,174,303 | B2 | 1/2019 | Behrendorff |
| 10,494,600 | B2 | 12/2019 | Heijstra |
| 10,590,406 | B2 | 3/2020 | Koepke |
| 10,913,958 | B2 | 2/2021 | Koepke |
| 2010/0151543 | A1 | 6/2010 | Reeves |
| 2011/0312049 | A1 | 12/2011 | Osterhout |
| 2012/0045807 | A1 | 2/2012 | Simpson |
| 2013/0157322 | A1 | 6/2013 | Simpson |
| 2013/0330809 | A1 | 12/2013 | Mueller |
| 2015/0147794 | A1 | 5/2015 | Chung |
| 2016/0177353 | A1 | 6/2016 | Yu |
| 2017/0121717 | A1 | 5/2017 | Stephanopoulos |
| 2019/0185888 | A1 | 6/2019 | Koepke |
| 2019/0352679 | A1 | 11/2019 | Gonzalez |
| 2020/0048665 | A1 | 2/2020 | Simpson |
| 2020/0277635 | A1 | 9/2020 | Pandit |

FOREIGN PATENT DOCUMENTS

| | | | | |
|---|---|---|---|---|
| WO | WO2014/036152 A1 * | 8/2013 | ............... | C12N 1/21 |
| WO | 2014004625 A1 | 1/2014 | | |

(Continued)

OTHER PUBLICATIONS

Hille et al: "Structure: Function Studies of the Cytosolic, Mo- and NAD+-Dependent Formate Dehydrogenase from Cupriavidus necator," Inorganics, vol. 8, issue 41, pp. 1-13 (Year: 2020).*

(Continued)

*Primary Examiner* — Tekchand Saidha

(57) ABSTRACT

The disclosure provides genetically engineered microorganisms and methods for improved biological production of ethylene glycol and precursors of ethylene glycol. The microorganism of the disclosure produces ethylene glycol or a precursor of ethylene glycol through one or more of 5,10-methylenetetrahydrofolate, oxaloacetate, citrate, malate, and glycine. The disclosure further provides compositions comprising ethylene glycol or polymers of ethylene glycol such as polyethylene terephthalate.

20 Claims, 18 Drawing Sheets

Specification includes a Sequence Listing.

(56) References Cited

FOREIGN PATENT DOCUMENTS

| WO | 2017156166 A1 | 9/2017 | |
| WO | WO2019/126400 A1 * | 12/2018 | ............... C12P 7/18 |

OTHER PUBLICATIONS

Extended European Search Report issued in corresponding European Patent Application No. 18891435.2, dated Oct. 27, 2021, 8 pages.
International Search Report and Written Opinion issued in corresponding International Application No. PCT/US2018/066619, dated Apr. 18, 2019 (pp. 1-6).
Abrini, Arch Microbiol, 161: 345-351, 1994.
Alkim et al., Microb Cell Fact, 14: 127, 2015.
Atul, Chem Eng Sci, 59: 2881-2890, 2004.
Bourgade et al. "Design, Analysis, and Implementation of a Novel Biochemical Pathway for Ethylene Glycol Production in Clostridium autoethanogenum" ACS Synthetic Biology 2022 11 (5), 1790-1800. https://doi.org/10.1021/acssynbio.1c00624.
Chiba, Section 18: Diet Formulation and Common Feed Ingredients, Animal Nutrition Handbook, 3rd revision, pp. 575-633, 2014.
Chinn, Recovery of Glycols, Sugars, and Related Multiple -OH Compounds from Dilute-Aqueous Solution by Regenerable Adsorption onto Activated Carbons, University of California Berkeley, 1999.
Dhale, Atul, et al., Chem Eng Sci, 59: 2881-2890, 2004.
Drake, Acetogenic Prokaryotes, In: The Prokaryotes, 3rd edition, p. 354, New York, NY, 2006.
Ebrahim., COBRApy: Constraints-Based Reconstruction and Analysis for Python, BMC Syst Biol, 7: 74, 2013.
Flamholz, E. Noor, A. Bar-Even, R. Milo (2012) eQuilibrator—the biochemical thermodynamics calculator, Nucleic Acids Res 40:D770-5.
Herzberger et al., Chem Rev., 116(4): 2170-2243 (2016).
Hungate, "Chapter IV A Roll Tube Method for Cultivation of Strict Anaerobes," Methods in Microbiology, vol. 3, Part B, 1969, pp. 117-132.
Islam et al., Metab Eng, 41: 173-181, 2017.
Jensen, Optlang: An Algebraic Modeling Language for Mathematical Optimization, The Journal of Open Source Software, 2, doi:10.21105/joss.00139, 2017.
Khusnutdinova et al., "Exploring bacterial carboxylate reductases for the reduction of bifunctional carboxylic acids," Biotechnol J. Nov. 2017 ; 12(11): . doi: 10.1002/biot.201600751. pp. 1-25.
Köpke, Curr Opin Biotechnol, 22: 320-325, 2011.
Maia, Proceedings of the Genetic and Evolutionary Computation Conference Companion on—GECCO '17, New York, New York, ACM Press, 1661-1668, 2017.
Marcellin, Green Chem, 18: 3020-3028, 2016.
Noor et al. "An integrated open framework for thermodynamics of reactions that combines accuracy and coverage" vol. 28 No. 15, 2012, pp. 2037-2044. doi:10.1093/bioinformatics/bts317.
Noor et al. "Consistent Estimation of Gibbs Energy Using Component Contributions" Jul. 2013, vol. 9, Issue 7, e1003098.
Noor et al. "Pathway Thermodynamics Highlights Kinetic Obstacles in Central Metabolism" PLOS Computational Biology, Feb. 2014, vol. 10, Issue 2, e1003483.
Pereira et al., Metab Eng, 34: 80-87, 2016.
Perez, Biotechnol Bioeng, 110:1066-1077, 2012.
Ragsdale, Biochim Biophys Acta, 1784: 1873-1898, 2008.
Scheffen et al., "A new-to-nature carboxylation module to improve natural and synthetic CO2 fixation," Nature Catalysis | www.nature.com/natcatal, https://doi.org/10.1038/s41929-020-00557-y, Published: Jan. 4, 2021, 13 pages.
Tanner, Int J System Bacteriol, 43: 232-236, 1993.
Tirado-Acevedo, Production of bioethanol from synthesis gas using Clostridium ljungdahlii, PhD thesis, North Carolina State University, 2010.
Jranukul et al., Metab Eng, 51: 20-31, 2019.
Williams et al., "Conjugative plasmid transfer from *Escherichia coli* to Clostridium acetobutylicum," J Gen Microbiol. May 1990; 136(5): 819-26. doi: 10.1099/00221287-136-5-819. 1990.
Wolfe, "Microbial Formation of Methane," Advances in Microbial Physiology, vol. 6, 1971, pp. 107-146.
Xiao et al., Ind Eng Chem Res. 54(22): 5862-5869 (2015).
Zhang et al. "Production of C2-C4 diols from renewable bioresources: new metabolic pathways and metabolicengineering strategies", Biotechnology for Biofuels, vol. 10, No. 1, Dec. 1, 2017 (Dec. 1, 2017), p. 299.
International Search Report and Written Opinion issued in corresponding International Application No. PCT/US2022/074592, dated Nov. 24, 2022, 13 pages.
Pandit, Aditya Vikram et al., "Engineering *Escherichia coli* for the utilization of ethylene glycol", Microbial Cell Factories, Jan. 22, 2021 (published online), vol. 20, article No. 22, pp. 1-17.
Sambrook J, Fritsch EF, Maniatis T: Molecular Cloning: A laboratory Manual, Cold Spring Harbour Laboratory Press, Cold Spring Harbour, 1989.

\* cited by examiner

SEQUENCE LISTING

```
Sequence total quantity: 82
SEQ ID NO: 1           moltype = DNA  length = 1101
FEATURE                Location/Qualifiers
misc_feature           1..1101
                       note = Codon-adapted nucleotide sequence
source                 1..1101
                       mol_type = other DNA
                       organism = synthetic construct
SEQUENCE: 1
atggtacatt atggattaaa gggaataact tgtgtagaaa cttctatatc tcatatagat   60
ggagaaaagg gaaggcttat atacagagga catcatgcta aggacatagc actaaatcat  120
agctttgaag aggctgctta tttaatctta tttggaaagc tcccaagtac agaagagctt  180
caagtcttca aagacaaatt ggcagcagaa agaaatttac cagaacatat agaaagactt  240
attcaatcct taccaaataa tatggatgat atgtcagttt taagaactgt tgtaagtgca  300
cttggtgaaa atacctatac atttcatcct aaaacagaag aggctataag acttatagca  360
ataactcctt ccataattgc ttatagaaaa agatggacaa gaggtgaaca agcaatagca  420
ccatcatcac aatatggaca tgttgaaaat tattattaca tgcttacagg agaacagcct  480
agtgaggcta agaaaaaagc acttgaaacc tatatgatat tagctacaga acatggcatg  540
aatgcttcta cttttttctgc aagagtaact ttaagcactg aatcagattt agtatcagca  600
gtaacagcag cattaggtac tatgaaggga ccactacatg gcggcgctcc ctctgcagtt  660
acaaagatgt tagaagacat aggagaaaag gaacatgcag aggcttatct aaaagaaaaa  720
cttgaaaagg gagagagact catgggtttt ggacatagag tatacaagac taaagatcct  780
agagcagaag cattaagaca aaaggcagaa gaagtggcag gaaatgatag agatcttgat  840
cttgcattgc acgttgaagc agaggctata agattacttg aaatatataa accaggaaga  900
aaactttata ctaatgttga attttatgca gctgctgtta tgagggctat agactttgac  960
gatgaattat ttactcctac tttttccgct tctcgtatgg ttggatggtg tgcgcatgtg 1020
cttgaacagg cagagaataa catgattttt agaccatctg cacaatatac aggtgctatc 1080
ccagaagaag tactttctta a                                           1101

SEQ ID NO: 2           moltype = AA  length = 366
FEATURE                Location/Qualifiers
source                 1..366
                       mol_type = protein
                       organism = Bacillus subtilis
SEQUENCE: 2
MVHYGLKGIT CVETSISHID GEKGRLIYRG HHAKDIALNH SFEEAAYLIL FGKLPSTEEL   60
QVFKDKLAAE RNLPEHIERL IQSLPNNMDD MSVLRTVVSA LGENTYTFHP KTEEAIRLIA  120
ITPSIIAYRK RWTRGEQAIA PSSQYGHVEN YYYMLTGEQP SEAKKKALET YMILATEHGM  180
NASTFSARVT LSTESDLVSA VTAALGTMKG PLHGGAPSAV TKMLEDIGEK EHAEAYLKEK  240
LEKGERLMGF GHRVYKTKDP RAEALRQKAE EVAGNDRDLD LALHVEAEAI RLLEIYKPGR  300
KLYTNVEFYA AAVMRAIDFD DELFTPTFSA SRMVGWCAHV LEQAENNMIF RPSAQYTGAI  360
PEEVLS                                                             366
```

| SEQ ID NO: 3 | moltype = DNA length = 1362 |
| --- | --- |
| FEATURE | Location/Qualifiers |
| misc_feature | 1..1362 |
| | note = Codon-adapted nucleotide sequence |
| source | 1..1362 |
| | mol_type = other DNA |
| | organism = synthetic construct |

SEQUENCE: 3

```
atgaaaaaat gttcttacga ctataaatta aataatgtaa atgatcctaa cttctataaa   60
gatatattcc cttatgaaga agtacctaaa atagtattta ataatattca attaccaatg  120
gatctgcctg ataacatata cataactgat actaccttcc gtgatggaca acaatcaatg  180
cctcctttata caagtagaga aatagtaagg attttttgatt atttgcatga attagacaac  240
aattcaggaa taataaaaca aacagaattt tttttatata ccaaaaaaga tagaaaagca  300
gctgaagttt gtatggaaag aggatacgag ttccctgtaa ctacttcttg gattagggca  360
gataaagagg acttaaaatt agttaaggat atgggcataa aggaaacagg tatgttaatg  420
agttgttcag actatcacat ttttaagaaa ttaaaaatga caagaaaaga gacaatggat  480
atgtatcttg atttagctag agaggctcta aataatggta ttagacctag atgtcattta  540
gaagatatta caagagcaga tttttatgga tttgtagtac cttttgtaaa tgaacttatg  600
aaaatgagca agaggcaaa catcccaata aaaataaggg cttgtgatac tcttggatta  660
ggggtacctt ataatggagt tgaaatacca agatctgtac agggaataat tcatggtttg  720
agaaacatat gtgaagttcc ttctgaatct attgaatggc atggacataa tgatttctat  780
ggagtagtaa ctaactcctc cacggcatgg ctatatgaga caagcagcat aaacacttcc  840
ttcttgggaa taggagaaag aacaggaaac tgtccacttg aagcaatgat atttgaatat  900
gctcaaataa aggaaatac taaaaatatg aaacttcatg taataacgga gcttgctcaa  960
tattttgaaa aggaaataaa atattctgta cctgttagaa ctcctttgt tggaactgat 1020
tttaatgtaa caagggctgg catacatgca gatggtatcc taaaagatga agaaatatat 1080
aatattttg atacagataa gatactggga aggcctgtag tagtagctgt tccccagtat 1140
tcaggaaggg ctggaatagc agcatgggtg aacacttatt ataggcttaa agatgaagat 1200
aaagttaata aaaatgacag cagaatagat caaattaaaa tgtgggtaga tgagcaatac 1260
cgcgctggta ggacatcgt aattggaaac aatgaactag aacttttagt ttcaaaagta 1320
atgccagaag taatagaaaa aacagaagaa agggcttctt aa                    1362
```

| SEQ ID NO: 4 | moltype = AA length = 453 |
| --- | --- |
| FEATURE | Location/Qualifiers |
| source | 1..453 |
| | mol_type = protein |
| | organism = Clostridium kluyveri |

SEQUENCE: 4

```
MKKCSYDYKL NNVNDPNFYK DIFPYEEVPK IVFNNIQLPM DLPDNIYITD TTFRDGQQSM   60
PPYTSREIVR IFDYLHELDN NSGIIKQTEF FLYTKKDRKA AEVCMERGYE FPEVTSWIRA  120
DKEDLKLVKD MGIKETGMLM SCSDYHIFKK LKMTRKETMD MYLDLAREAL NNGIRPRCHL  180
EDITRADFYG FVVPFVNELM KMSKEANIPI KIRACDTLGL GVPYNGVEIP RSVQGIIHGL  240
RNICEVPSES IEWHGHNDFY GVVTNSSTAW LYGASSINTS FLGIGERTGN CPLEAMIFEY  300
AQIKGNTKNM KLHVITELAQ YFEKEIKYSV PVRTPFVGTD FNVTRAGIHA DGILKDEEIY  360
NIFDTDKILG RPVVVAVSQY SGRAGIAAWV NTYYRLKDED KVNKNDSRID QIKMWVDEQY  420
RAGRTSVIGN NELELLVSKV MPEVIEKTEE RAS                              453
```

| SEQ ID NO: 5 | moltype = DNA length = 1359 |
| --- | --- |
| FEATURE | Location/Qualifiers |
| misc_feature | 1..1359 |
| | note = Codon-adapted nucleotide sequence |
| source | 1..1359 |
| | mol_type = other DNA |
| | organism = synthetic construct |

SEQUENCE: 5

```
atgtcaataa acaacatagg tcctttact aaatcccact tagatatgtg tattaaaaac   60
aattcaattg atgatgcctt gtatgaaaag tatggagtaa agagatcact tagagatctt  120
aatggtattg aataaatgc tgggataaca atgtcagtt gtcaaagtc ttttactaca  180
gatgaaaatg gtaacagagt accttgtgca ggagagttat attatagagg atacgagatt  240
catgatctta taagggatt ttttttggac aatagatttg gatttgagga atgtacttat  300
ttgttacttt ttggcgtact tcctgacgaa aaagaacttc aaaattttcaa acaagtctta  360
aatatctctt acgatttacc tcatcatttt atacaagatg ttataatgaa atctcctaca  420
gcagacataa tagctaatat gactaaatcc acgcttgcac taggttccta tgataaaag  480
atgggagata actcacttga aaatgtcctt caacaatgta ttcaattaat atctatgttt  540
ccaaggcttg ctgtatactc ctatcagggt tatagacatt atgaattagg taaatcttgc  600
tatatacaca aacctcttcc agaattaagt tttgcagaaa atatattatc aactcttaga  660
tcaaatagaa aatatacaag attggaagca agtacttg atcttgccct agttttacac  720
atggaacatg gcggcggctc aaattctact tttactacaa gggtagttac ttcatcagga  780
agtgatacg atgcaactat ggcagcagca ttatgttact taaaaggacc tttaaatgga  840
ggcggcgatt atcaagtaat gggtatgatg aagaatataa agataatgt aagtgatata  900
actgacgaag aagaagttgg tgaatatatt agaaaaattg taaaccgtga agcgtatgat  960
aaaacaggaa tagtatacgg aatgggtcat ccattctata gcatatctga ccccaaggct 1020
ttagagttca gaaatatgt aaaattactt gcagcagaaa aggaatgga tgaagaatat 1080
gcattatatg aaatgataga aaggattgca ccagaaatta cgcaagaaa gaagaagata 1140
tataaaggag tatgtattaa tatagattat tattctggtt tgcttttaaa aatgttaaag 1200
atcccagcag agatgtttac tccattattt gctattgcca gagttgtagg atggtcggca 1260
catagaatgg aagaacttgt aaattcttac aaaattcataa gacctgctta tacatctata 1320
gcagagataa aggaatacgt acctataat gaaagataa                        1359
```

```
SEQ ID NO: 6              moltype = AA   length = 452
FEATURE                   Location/Qualifiers
source                    1..452
                          mol_type = protein
                          organism = Clostridium sp. L2-50
SEQUENCE: 6
MSINNIGPFT KSHLDMCIKN NSIDDALYEK YGVKRSLRDL NGIGINAGIT NVSLSKSFTT   60
DENGNRVPCA GELYYRGYEI HDLIKGFFLD NRFGFEECTY LLLFGVLPDE KELQNFKQVL  120
NISYDLPHHF IQDVIMKSPT ADIIANMTKS TLALGSYDKK MGDNSLENVL QQCIQLISMF  180
PRLAVYSYQG YRHYELGKSC YIHKPLPELS FAENILSTLR SNRKYTRLEA RVLDLALVLH  240
MEHGGGSNST FTTRVVTSSG SDTYATMAAA LCSLKGPLNG GGDYQVMGMM KNIRDNVSDI  300
TDEEEVGEYI RKIVNREAYD KTGIVYGMGH PFYSISDPRA LEFKKYVKLL AAEKGMDEEY  360
ALYEMIERIA PEIIAEERKI YKGVCINIDY YSGLLYKMLK IPAEMFTPLF AIARVVGWSA  420
HRMEELVNSY KIIRPAYTSI AEIKEYVPIN ER                                452

SEQ ID NO: 7              moltype = DNA   length = 1119
FEATURE                   Location/Qualifiers
misc_feature              1..1119
                          note = Codon-adapted nucleotide sequence
source                    1..1119
                          mol_type = other DNA
                          organism = synthetic construct
SEQUENCE: 7
atgacagcaa caaggggcct tgaaggggta gtagcgacta ctagtagtgt aagttcaatt    60
atagatgata ctttgactta tgttggatat gatatagatg atcttacgga aaatgcaagc   120
tttgaagaaa taatatattt attgtggcat ttgagattac aaaacaaaaa ggaattagaa   180
gaattaaaac aacaattagc caaagaggca gctgttcctc aggaaataat agaacatttc   240
aaatcctata gcttagaaaa tgttcatcct atggctgcac ttagaactgc tatatccctc   300
ttaggtcttt tggattctga ggcagatact atgaatccag aggctaacta tagaaaagca   360
ataagattac aggctaaagt cccaggatta gttgcagcat tttcaagaat acgaaaagga   420
ttagaaccag tagagccaag agaagattac ggaatagcag agaattttt tgtatacttt   480
aatggcgaag agcctagtcc aatagaagtt gaagcattta taaagcact tatacttcat   540
gctgaccatg aacttaacgc atctacattt acagctagag tttgtgtagc cactcttcct   600
gatatttatt ccggcattac tgctgcaatt gggctctta agggacctct acatggcggc   660
gccaacgagg gtgtaatgaa gatgttaaca gagattggag aggttgaaaa tgctgaacct   720
tatataagag ccaaacttga aaaaaaggaa aaaataatgg gatttggtca tagagtatac   780
aaacatggag atcctagagc aaaacatctt aagaaatgt caaagagact tacaaattta   840
acaggtgaat caaaatggta tgaaatgagt attcgtattg aagatatagt tacgtcgag   900
aagaaacttc cccctaatgt agattttac agtgcatctg tttatcattc gcttggaatc   960
gatcacgatt tatttacgcc tatatttgct gtaagtagaa tgagcggatg gttagctcat  1020
attctcgaac agtacgacaa taacagactt ataagaccac gtgctgatta tacaggtcct  1080
gacaaacaaa aatttgtacc tatagaagaa agagcataa                         1119

SEQ ID NO: 8              moltype = AA   length = 372
FEATURE                   Location/Qualifiers
source                    1..372
                          mol_type = protein
                          organism = Bacillus subtilis
SEQUENCE: 8
MTATRGLEGV VATTSSVSSI IDDTLTYVGY DIDDLTENAS FEEIIYLLWH LRLPNKKELE   60
ELKQQLAKEA AVPQEIIEHF KSYSLENVHP MAALRTAISL LGLLDSEADT MNPEANYRKA  120
IRLQAKVPGL VAAFSRIRKG LEPVEPREDY GIAENFLYTL NGEEPSPIEV EAFNKALILH  180
ADHELNASTF TARVCVATLS DIYSGITAAI GALKGPLHGG ANEGVMKMLT EIGEVENAEP  240
YIRAKLEKKE KIMGFGHRVY KHGDPRAKHL KEMSKRLTNL TGESKWYEMS IRIEDIVTSE  300
KKLPPNVDFY SASVYHSLGI DHDLFTPIFA VSRMSGWLAH ILEQYDNNRL IRPRADYTGP  360
DKQKFVPIEE RA                                                      372

SEQ ID NO: 9              moltype = DNA   length = 1785
FEATURE                   Location/Qualifiers
misc_feature              1..1785
                          note = Codon-adapted nucleotide sequence
source                    1..1785
                          mol_type = other DNA
                          organism = synthetic construct
SEQUENCE: 9
atgcaaatta tggaagaaga aggaagattt gaagcagaag tggcagaagt agaaagttgg    60
tggggaacag agcgttttag gcttactaaa aggccttata cggcaaggga cgttgtactt   120
ttaagaggaa ccttgagaca gtcttatgcc agtggcgaga tggctaagaa attatggaga   180
actttaaag cgcatcaggc tggcggcact gcttcaagaa cttttggtgc tttagatcca   240
gttcaagtta caatgatggc taagcaccta gatactattt atgtaagcgg atggcagtgt   300
tcatctacac acacatcaac aaatgaacct ggcccagatc ttgcagacta tccttatgat   360
actgtgccaa ataggtaga acatcttttt tttgctcaat atatcatga ccgcaagcaa   420
agagaggcaa gaatgagtct tccgcgagca gaaagagccc gtgctcctta tgtagatttt   480
ttaacctat aatagcaga tggattggca gcgccacgac tacagttaaa                540
ctttgtaaac tttttgtaga gagaggtgct gcgggagttc accttgagga tcaatcatct   600
gttacaaaaa aatgtggaca catggctgga aaagttttag tggcagtttc agagcatgtt   660
aataggcttg tagctgctag acttcaattt gacgttatgg gcgtgagac agtttttagtg  720
gcaaggacag atgcagtagc agctacactt atacaaacta atgtagatgc cagggatcac   780
caattcatag taggagccac aaatccagga ttgagaggtc agtctcttgc agctgtatta   840
```

-continued

```
tctgctggta tgtcagctgg taagagcgga agagaattgc aagcaatcga agatgaatgg    900
ctagcagcag cacaattaaa gacttttagc gaatgtgtac gagatgctat tgcaggacta    960
ggcgtggcag caaaggaaaa gcaaagaaga ctccaagaat gggacagggc aacaggcggc   1020
tatgatagat gtgtaagcaa tgatcaagca agagatatcg cagcatccct ggagtaact    1080
tctgtattct gggattggga tttgcctaga actagagaag gtttttacag attcagaggc   1140
tcagtagctg ccgcagtagt tagaggcaga gcatttgctc cacatgcaga tgtattatgg   1200
atggaaacat cttcaccaaa tgtggcagaa tgtactgcat tttcagaagg agttaaggca   1260
gcatgtccag aagcaatgct cgcgtataat ttgtcaccat cctttaactg ggacgcaagt   1320
ggcatgacag atgcagaaat ggcagcattt attccatctg tactagatt gggatatgta   1380
tggcaattta taactcttgc tggttttcat gctgatgcct tggttacaga tacttttgct   1440
agggattttg ctagaagagg tatgttagct tatgttgaaa gaatacagag aagaagaaga   1500
ataaatggtg tagaaactct tgaacatcaa aaatggtcag gagcaaattt ttacgaccgt   1560
gtgttgaaag cagtacaagg cggcataagc agtactgcag ctatgggaaa aggtaaagta   1620
cctcacttcc cagcatttt tttttgctta gaaaaaaata agccatcatt cgttcacagt   1680
tttgatgtag tactttttac aggtgttaca gaggaacaat tcaaagatcc aaggcctgcc   1740
actggttcaa gtggacttca ggttatggcc aaatcacgta tttaa                   1785

SEQ ID NO: 10           moltype = AA   length = 594
FEATURE                 Location/Qualifiers
source                  1..594
                        mol_type = protein
                        organism = Zea mays
SEQUENCE: 10
MQIMEEEGRF EAEVAEVESW WGTERFRLTK RPYTARDVVL LRGTLRQSYA SGEMAKKLWR    60
TLKAHQAGGT ASRTFGALDP VQVTMMAKHL DTIYVSGWQC SSTHTSTNEP GPDLADYPYD   120
TVPNKVEHLF FAQLYHDRKQ REARMSLPRA ERARAPYVDF LKPIIADGDT GFGGATATVK   180
LCKLFVERGA AGVHLEDQSS VTKKCGHMAG KVLVAVSEHV NRLVAARLQF DVMGVETVLV   240
ARTDAVAATL IQTNVDARDH QFIVGATNPG LRGQSLAAVL SAGMSAGKSG RELQAIEDEW   300
LAAAQLKTFS ECVRDAIAGL GVAAKEKQRR LQEWDRATGG YDRCVSNDQA RDIAASLGVT   360
SVFWDWDLPR TREGFYRFRG SVAAAVVRGR AFAPHADVLN METSSPNVAE CTAFSEGVKA   420
ACPEAMLAYN LSPSFNWDAS GMTDAEMAAF IPSVARLGYV WQFITLAGFH ADALVTDTFA   480
RDFARRGMLA YVERIQREER INGVETLEHQ KWSGANFYDR VLKAVQGGIS STAAMGKGKV   540
PHFPAFFFCL EKNKPSFVHS FDVVLFTGVT EEQFKDPRPA TGSSGLQVMA KSRI          594

SEQ ID NO: 11           moltype = DNA   length = 1305
FEATURE                 Location/Qualifiers
misc_feature            1..1305
                        note = Codon-adapted nucleotide sequence
source                  1..1305
                        mol_type = other DNA
                        organism = synthetic construct
SEQUENCE: 11
atgaaaacaa gaactcaaca aatagaagaa ttacaaaaag aatggacgca accaagatgg    60
gaaggtatta cgaggcctta ttctgcagaa gatgtagtaa aattaagagg ttctgtaaat   120
ccagaatgta ctcttgccca gcttggagca gctaaaatgt ggagactttt gcacggtgaa   180
tcaaagaagg gttatataaa ctctcttggc gctttaacag gcggcaggc acttcaacag   240
gctaaggcag gaatagaagc agtttatctt tctggatagc aagtagcagc agatgcaaat   300
ttagcagcat caatgtatcc tgatcagagc ttatacccag caaattcagt cccagctgta   360
gtagagagaa taaataatac ctttagaagg gcagatcaaa ttcaatgtc tgctggtatt   420
gaaccaggtg atccaagata cgtggattat tttttgccaa ttgtagcaga tgctgaggct   480
ggttttggcg gcgtattaaa tgcatttgaa ttaatgaaaa caatgatga ggctggtgct   540
gcagctgtcc attttgaaga tcagttagct tcagttaaga atgtggaca catgggcggc   600
aaggtattag ttccaaccca agaagcaata caaaaattag tggcagctag acttgcagct   660
gatgtaacag gtgtgcctac attactagtt gcaagaacga atgcagatgc tgcagatctt   720
attactagtg actgtgatcc ttatgattca gaatttatta caggagaaag aaccagtgag   780
ggattttta gaactcatgc aggaatagaa caggctatat caagaggat agcttatgct   840
ccttatgcag atcttgtttg gtgtgaaaca tctacaccag atctcgaact tgcccgtaga   900
tttgccagg caatacatgc taagtatcca ggaaaattat agcgtacaa tgttctcct   960
tcatttaatt ggcagaagaa cttagatgac aaaacaatag caagttttca gcaacaatta  1020
tcagatatgg gatacaaatt tcagttcata acattagctg gaatacatag tatgtggttt  1080
aatatgtttg atcttgcaaa tgcttatgca caaggagaag gcatgaagca ttatgtagaa  1140
aaagtacaac agccagaatt tgcagctgcc aaggatggat atactttcgt ttctcatcaa  1200
caagaggttg gaactggata ttttgataag gttacaacaa ttatacaggg cggcacatcg  1260
tctgttactg cactaacagg ttcaactgaa gaatctcaat tttaa                  1305

SEQ ID NO: 12           moltype = AA   length = 434
FEATURE                 Location/Qualifiers
source                  1..434
                        mol_type = protein
                        organism = Escherichia coli
SEQUENCE: 12
MKTRTQQIEE LQKEWTQPRW EGITRPYSAE DVVKLRGSVN PECTLAQLGA AKMWRLLHGE    60
SKKGYINSLG ALTGGQALQQ AKAGIEAVYL SGWQVAADAN LAASMYPDQS LYPANSVPAV   120
VERINNTFRR ADQIQWSAGI EPGDPRYVDY FLPIVADAEA GFGGVLNAFE LMKAMIEAGA   180
AAVHFEDQLA SVKKCGHMGG KVLVPTQEAI QKLVAARLAA DVTGVPTLLV ARTDADAADL   240
ITSDCDPYDS EFITGERTSE GFFRTHAGIE QAISRGLAYA PYADLVWCET STPDLELARR   300
FAQAIHAKYP GKLLAYNCSP SFNWQKNLDD KTIASFQQQL SDMGYKFQFI TLAGIHSMWF   360
NMFDLANAYA QEGMKHYVE KVQQPEFAAA KDGYTFVSHQ QEVGTYFDK VTTIIQGGTS    420
SVTALTGSTE ESQF                                                     434
```

-continued

```
SEQ ID NO: 13            moltype = DNA  length = 1218
FEATURE                  Location/Qualifiers
misc_feature             1..1218
                         note = Codon-adapted nucleotide sequence
source                   1..1218
                         mol_type = other DNA
                         organism = synthetic construct
SEQUENCE: 13
atgacagtta ctccacattt atttataccg ggcccaacaa acataccaga tgcagtacgt   60
atggcaatga atatacctat ggaagacatg cgttcaccag agttcccaaa atttacatta  120
cctttatttg aggatttaaa aaaagcattt aagatgaaag atggaagagt ttttatattt  180
ccatcttcag gaacaggcgc atgggaatca gctgtagaaa acactcttgc cactggagat  240
aaggttttaa tgtcaagatt tggacaattt ctttgctat gggtagatat gtgtgaaaga  300
tgggattaa aagttgaagt atgtgatgaa gaatgggaca caggagtgcc agtagaaaaa  360
tatgctgata tacttgctaa agataaaaat catgaaataa aggctgtttt tgtaactcac  420
aatgaaacag caacaggtgt ttcttcagat gtggctggtg taagaaaagc acttgacgca  480
gcaaagcatc cagcactttt gatggtggat ggagtatcat cagttggttc tcttgatatg  540
agaatgggtg aatggggagt tgattgctgt gtatctgtaa gccaaaaggg ttttatgctt  600
cctacaggtt tggcatttt agctgtgtca cagaaggcat tagatattaa taaatcaaag  660
aatggcagaa tgaatagatg ctttttttcc tttgaggata tgataaaaac taatgatcag  720
ggtttttttc cttataccc cgccactcaa ttattgagag gattaagaac ttctctcgat  780
cttttgttcg cagaaggact agataatgta tttgcaagac atactagatt agctagtgga  840
gttagggctg ccgtagatgc atggggatta aaattgtgtg caaaagaacc taatgtat  900
tccgatactg tatcagcaat tttagttcca gaaggtattg attccaatgc tataacaaaa  960
acagcttatt atagatataa tacaagtttt ggtcttggat taaataaggt tgcaggaaaa 1020
gtattcagaa taggccattt aggtatgtta gatgaagtaa tgataggcgg cgctttattt 1080
gcagcagaga tggcacttaa agataatgga gtaaatctaa aattaggatc tggaacaggt 1140
gcagctgctg aatattttag taaaaatgct acaaagtctg ctactgcttt aactccaaaa 1200
caagcaaaag cggcataa                                               1218

SEQ ID NO: 14            moltype = AA  length = 405
FEATURE                  Location/Qualifiers
source                   1..405
                         mol_type = protein
                         organism = Hyphomicrobium methylovorum
SEQUENCE: 14
MTVTPHLFIP GPTNIPDAVR MAMNIPMEDM RSPEFPKFTL PLFEDLKKAF KMKDGRVFIF   60
PSSGTGAWES AVENTLATGD KVLMSRFGQF SLLWVDMCER LGLKVEVCDE EWGTGVPVEK  120
YADILAKDKN HEIKAVFVTH NETATGVSSD VAGVRKALDA AKHPALLMVD GVSSVGSLDM  180
RMGEWGVDCC VSGSQKGFML PTGLGILAVS QKALDINKSK NGRMNRCFFS FEDMIKTNDQ  240
GFFPYTPATQ LLRGLRTSLD LLFAEGLDNV FARHTRLASG VRAAVDAWGL KLCAKEPKWY  300
SDTVSAILVP EGIDSNAITK TAYYRYNTSF GLGLNKVAGK VFRIGHLGML DEVMIGGALF  360
AAEMALKDNG VNLKLGSGTG AAAEYFSKNA TKSATALTPK QAKAA                 405

SEQ ID NO: 15            moltype = DNA  length = 1185
FEATURE                  Location/Qualifiers
misc_feature             1..1185
                         note = Codon-adapted nucleotide sequence
source                   1..1185
                         mol_type = other DNA
                         organism = synthetic construct
SEQUENCE: 15
atgcaattta ggccttttaa tccaccagtt agaactctta tgggaccagg accaagcgat   60
gtacacccaa gaatattaga ggctatgagc cgtcctacaa taggacattt ggatcctgct  120
tttatacaga tgatggaaga agtaaaaact ttacttcagt atgcatttca aactaaaaat  180
gaacttacta tgccagtaag tgccccaggc tctgcaggca tggaaacatg ctttgccaac  240
ttagtagaac caggtgatca ggtatagtt tgccagaatg gtgtatttgg cggcagaatg  300
aaagaaaatg tagaaagatg tggcggcata cctataatgg ttgaagatac ttggggagag  360
gctgttgatc cagataaatt ggagactgca ttaaaggcta atccagaggc ttgtatagtg  420
gcatttgttc atgctgaaac tagtactggt gcacaaagtg atgctgaaac attggtaaaa  480
ttagctcatc agtatgattg tcttactata gttgatgctg ttacatcact tggcggcact  540
ccaataaagg tagatgaaga ggaaatagat gctatttata gtggaactca gaaatgcttt  600
tcatgtactc caggactttc accagtaagt ttcaatgaaa gggctcttga aaaaattagg  660
aacagaaaac aaaaagttca gtcgtggttt atgatttaa atctagttat gggatattgg  720
ggcggcggcg caaagcgtgc ttatcatcat acagcaccaa ttaatgcttt atatggactt  780
catgaggcac ttttgatgct tcaggaagag ggattagaga acgcatgggc aaggcaccaa  840
aaaaatcatc ttgctttacg ggctggactg gaagcaatgg gcctcacttt tatagtaaat  900
gaaggagata gactgcctca gttaaatgct gtatctatac cagaggggagt tgatgatggt  960
gctgttagat caaggcttct aaacgaatat aacttagaaa ttggtgctgg gttaggtgct 1020
ttagctggga aggtatggag aataggctta atgggtcatg caagtagagc agaaaatatt 1080
ctcttatgca taagttcatt agaggctata ttaagtgaga tgggtgctga catatctcaa 1140
ggtgtggcta ttcagcaat gcagaaggca cttgcgcaag cataa                 1185

SEQ ID NO: 16            moltype = AA  length = 394
FEATURE                  Location/Qualifiers
source                   1..394
                         mol_type = protein
                         organism = Sedimenticola thiotaurini
```

```
SEQUENCE: 16
MQFRPFNPPV RTLMGPGPSD VHPRILEAMS RPTIGHLDPA FIQMMEEVKT LLQYAFQTKN   60
ELTMPVSAPG SAGMETCFAN LVEPGDQVIV CQNGVFGGRM KENVERCGGI PIMVEDTWGE  120
AVDPDKLETA LKANPEACIV AFVHAETSTG AQSDAETLVK LAHQYDCLTI VDAVTSLGGT  180
PIKVDEWEID AIYSGTQKCL SCTPGLSPVS FNERALEKIR NRKQKVQSWF MDLNLVMGYW  240
GGGAKRAYHH TAPINALYGL HEALLMLQEE GLENAWARHQ KNHLALRAGL EAMGLTFIVN  300
EGDRLPQLNA VSIPEGVDDG AVRSRLLNEY NLEIGAGLGA LAGKVWRIGL MGHASRAENI  360
LLCISSLEAI LSEMGADISQ GVAIPAMQKA LAQA                              394

SEQ ID NO: 17          moltype = DNA  length = 1185
FEATURE                Location/Qualifiers
misc_feature           1..1185
                       note = Codon-adapted nucleotide sequence
source                 1..1185
                       mol_type = other DNA
                       organism = synthetic construct
SEQUENCE: 17
atgcggactc attcatttca cccaccagtt agaactctta tgggaccagg accttctgat    60
gtaaatccaa gagtacttga ggcaatgtca cgacctacaa ttggacactt agatcctgta   120
tttgtagata tgatggaaga attaaagagt ttgcttcaat atgcatttca aacaggaaat   180
caattaacta tgcctgtaag tggacctggc tcagctggaa tggaaacatg ttttgttaat   240
ctagttgaac ctggagataa agtaatagtt tgtcaaaatg gagtatttgg cggcaggatg   300
aaagaaaatg tagaaagatg tggcggcaca gcagtcatgg tggaagatgc atggggttcc   360
gcagttgacc cacaaaaact taaagatgca cttcaggcac atcctgatgc taaattagtt   420
gcttttgttc atgctgaaac tagtacagga gcacaaagcg atgcaaaggc tttagtagaa   480
attgctcata gacatgactg cttagtaatt gtggatacaa ttacctcatt aggcggcact   540
cctgtaaaag tagatgaatg gggaatagat gcagtttatt caggaaccca aaaatgctta   600
tcatgtaccc caggtctttc accagtatct ttctctgaaa gggctatgga agaataaaaa   660
cataggaaaa ctaaagtaca gtcttggttt atggatttaa atcttgttat gggctattgg   720
ggatcaggag caaaaagggc ttatcatcat actgctccta taaatgcatt gtacggtctt   780
cacgaagcat tagttatact tcaagaagag gggttagaaa atgcatgggc aagacatgct   840
catgctcata gagcactatt agctggtatt gaagcaatgg gattaaaatt tgtagtaaag   900
gaagatgaac ggttaccgca attaaatgct gtaggtattc cagaaggcgt agatgatgca   960
gctgtgcgtg cccagctcct tcaagattat aaccacgaaa taggtgctgg tcttggacct  1020
atggcaggaa aaatctggag aataggtctt atgggctatg gtgctaatcc taaaaatgta  1080
cttttctgct taggagcatt agaggatgta ctttcgcgca tgagggctcc tatagaaaga  1140
ggtgctgctc ttccagcagc tcatgctgca cttggcgctg cataa                  1185

SEQ ID NO: 18          moltype = AA  length = 394
FEATURE                Location/Qualifiers
source                 1..394
                       mol_type = protein
                       organism = Thermithiobacillus tepidarius
SEQUENCE: 18
MRTHSFHPPV RTLMGPGPSD VNPRVLEAMS RPTIGHLDPV FVDMMEELKS LLQYAFQTGN   60
QLTMPVSGPG SAGMETCFVN LVEPGDKVIV CQNGVFGGRM KENVERCGGT AVMVEDAWGS  120
AVDPQKLKDA LQAHPDAKLV AFVHAETSTG AQSDAKALVE IAHRHDCLVI VDTVTSLGGT  180
PVKVDEWGID AVYSGTQKCL SCTPGLSPVS FSERAMERIK HRKTKVQSWF MDLNLVMGYW  240
GSGAKRAYHH TAPINALYGL HEALVILQEE GLENAWARHA HAHRALLAGI EAMGLKFVVK  300
EDERLPQLNA VGIPEGVDDA AVRAQLLQDY NHEIGAGLGP MAGKIWRIGL MGYGANPKNV  360
LFCLGALEDV LSRMRAPIER GAALPAAHAA LGAA                              394

SEQ ID NO: 19          moltype = DNA  length = 1125
FEATURE                Location/Qualifiers
misc_feature           1..1125
                       note = Codon-adapted nucleotide sequence
source                 1..1125
                       mol_type = other DNA
                       organism = synthetic construct
SEQUENCE: 19
atgagaactc catttattat gaccccagga ccaacacaag ttcatgaaga agtaagaaag    60
gctatgtcca gagaagcaac taatcctgat ttagatgaaa attctacgaa gttctataaa   120
aatacctgta taagataaaa agattatta aatacagaaa atcaggtatt aattcttgat    180
ggcgaaggta tttaggtttt ggaagcagct tgtgcaagct taactgaaca aggagataga   240
gtactttgta tagataatgg tatttttgga aagggttttg gtgattttc taaaatgtat    300
ggcggcgaag ttgtatactt cgagtctgat tatagaaagg gtagatgt agaaaaactt     360
gaagagttcc ttaaaagaga ttctaacttc aaatacgcga cactagtaca ctgtgaaaca   420
ccagcgggta taactaatcc tatagataag atatgtactt tattaaataa atatggtgtg   480
ctttcagtag tagatagtgt aagttcagta ggcggcgatg aaataaatgt agatgagtgg   540
aaaaatagata tagcttagg cggctctcaa aagtgtatat cagcgccatc aggattaact   600
ttcctttcaa tttcagaaaa agcaatggat actatgataa atagaaaaac tcctatagca   660
gcattttatt gtaatcttac aatttggaaa ggttggtatg aagaaaagtg gttccctat    720
actcagccaa ttaatgcaat atatgcactt gattgtgctt tagatagact tttagaaaca   780
gattatataa atagacataa agacaatagc ttaaagagcc tgtaaaaagt                840
ggacttgaat tgtatccttt agattcctat tcaaatactg taactacttt tcttgtacca   900
gaaggaataa attttgaaga tgtatttgaa gatatgatga agatcacaa cataatgata   960
ggcggcgcg ttgatattt aaaaggaaaa gttattgaa taggacacat gggcgaaaac     1020
tgctatgaag aaaaatata taaacttta aaggcacttg atacagtttt aaaaaatat     1080
ggagcaaaac taaacggaga gatttacaag cactttgtag attag                   1125
```

```
SEQ ID NO: 20              moltype = AA  length = 374
FEATURE                    Location/Qualifiers
source                     1..374
                           mol_type = protein
                           organism = Clostridium acidi-urici
SEQUENCE: 20
MRTPFIMTPG PTQVHEEVRK AMSREATNPD LDENFYEFYK NTCNKIKRLL NTENQVLILD    60
GEGILGLEAA CASLTEQGDR VLCIDNGIFG KGFGDFSKMY GGEVVYFESD YRKGIDVEKL   120
EEFLKRDSNF KYATLVHCET PAGITNPIDK ICTLLNKYGV LSVVDSVSSV GGDEINVDEW   180
KIDIALGGSQ KCISAPSGLT FLSISEKAMD TMINRKTPIA AFYCNLTIWK GWYEEKWFPY   240
TQPINAIYAL DCALDRLLET DYINRHKTIA NATREALVKS GLELYPLDSY SNTVTTFLVP   300
EGINFEDVFE DMMKDHNIMI GGAFDYLKGK VIRIGHMGEN CYEEKIYITL KALDTVLKKY   360
GAKLNGEIYK HFVD                                                    374

SEQ ID NO: 21              moltype = DNA  length = 1155
FEATURE                    Location/Qualifiers
misc_feature               1..1155
                           note = Codon-adapted nucleotide sequence
source                     1..1155
                           mol_type = other DNA
                           organism = synthetic construct
SEQUENCE: 21
atgggaaaat ttttaaaaaa gcactatata atggcgccag gacctacacc agtaccaaat    60
gatatattaa ctgaaggggc taaagaaact atacaccatc gcacgcccca atttgtatct   120
ataatggaag agacactgga atcagccaaa tatatcttcc aaactaagca caatgtttat   180
gcatttgcat ctacaggtac aggtgctatg gaagcagcag ttgctaactt ggtaagtcca   240
ggtgacaagg ttatagtagt agttgcagga aaatttgggg agagatggag agaactttgt   300
caggcttatg gtgctgatat agtagagatt gccttggagt ggggagatgc tgttactcca   360
gaacaaattg aagaagcctt aaataaaaat cctgatgcta agtagtatt tacaacttat   420
tctgaaacat caactggaac agttatagat cttgaaggaa tagctagagt tactaaagaa   480
aaagatgtgg ttctggttac agatgcagtt tcggcattag tgctgagcc attaaaaatg   540
gatgaatggg gagtagactt agtggttaca ggttctcaaa agggacttat gcttccacca   600
ggacttgcat taataagctt aaatgataaa gcatggggat tagtagaaaa atccagatca   660
ccaagatatt actttgatct tagagcatac agaaaaagct atccagataa cccatacaca   720
ccagcagtaa atatgatata tatgctgaga aaggctcttc agatgataaa ggaagaaggt   780
attgaaaatg tatgggaaag gcatagaata ctgggtgatg ctaccagagc agcagttaaa   840
gcattagggt tagaattact gtcaaagcgt ccgggaaatg tagttacagc tgtaaaagtt   900
ccagaaggta ttgatggtaa acaaaatacct aaaaatgata gatcaaaata tggagttacc   960
attgcaggcg gccaggctaa attaaaaggt aaaatttcc gtattgccca tttaggatat   1020
atgagtccat tgatactat cactgctata tctgcattga acttacatt aaaggaactt   1080
ggatatgaat ttgaattagg agttggagta aaggctgcag aggcagtatt tgctaaagaa   1140
tttataggag aataa                                                   1155

SEQ ID NO: 22              moltype = AA  length = 384
FEATURE                    Location/Qualifiers
source                     1..384
                           mol_type = protein
                           organism = Thermotoga maritima
SEQUENCE: 22
MGKFLKKHYI MAPGPTPVPN DILTEGAKET IHHRTPQFVS IMEETLESAK YIFQTKHNVY    60
AFASTGTGAM EAAVANLVSP GDKVIVVVAG KFGERWRELC QAYGADIVEI ALEWGDAVTP   120
EQIEEALNKN PDAKVVFTTY SETSTGTVID LEGIARVTKE KDVVLVTDAV SALGAEPLKM   180
DEWGVDLVVT GSQKGLMLPP GLALISLNDK AWGLVEKSRS PRYYFDLRAY RKSYPDNPYT   240
PAVNMIYMLR KALQMIKEEG IENVWERHRI LGDATRAAVK ALGLELLSKR PGNVVTAVKV   300
PEGIDGKQIP KIMRDKYGVT IAGGQAKLKG KIFRIAHLGY MSPFDTITAI SALELTLKEL   360
GYEFELGVGV KAAEAVFAKE FIGE                                         384

SEQ ID NO: 23              moltype = DNA  length = 1230
FEATURE                    Location/Qualifiers
misc_feature               1..1230
                           note = Codon-adapted nucleotide sequence
source                     1..1230
                           mol_type = other DNA
                           organism = synthetic construct
SEQUENCE: 23
atgaatttaa gagaaactgc actgaaattt cataagata cgaaggtaa atagcacta     60
aaatgcaaag ttccagtaaa aaataaagaa gatttgacac ttgcctatac accaggagtt   120
gctgaaccct gtcctagaaat aaataagaat cctgaatgca tatatgatta tacatctaaa   180
ggtaactggg tagcagtagt aacaaatgga accgcagtat taggcttagg aaatattgta   240
gctgggctg tcttccagt tatggaaggt aaatctgtcc ttttcaaaac tttgctggt   300
gtagatgcat ttccaatctg cttggaatca aagatataa atgaaatagt agctgcagta   360
aaattaatgg aacctacatt tggcggcata aatttagagg atataaaggc accagaatgt   420
tttgaaatag aatcaaaact taagagggtc tgtaatatac agtattcca tgatgatcag   480
catggtactg cagttgtatc ttctgcatgt tttataaatg cactaaaaat gataataag   540
aaatttgagg acctaaaaat agtagtaaat ggtgcgggtg ctgctggaac agctattact   600
aaattactta taaaaatggg tacaaaaaat gtaaactttt gtgacactaa gggcgctatt   660
tataagagaa ggcctatagg catgaataag ttcaaagatg aaatggctga ataacaaat   720
ccaaatcttc aaaaaggcac actagcagat gtattaaaag gtgctgatgt cttccttgga   780
gtttctgctg caaattgtgt tacagaagaa atggtaaaat caatgaataa ggattcaata   840
```

```
ataatggcaa tggctaatcc aaacccagaa atattaccag atttagctat aaaggctggt    900
gctaaagtag tatgtactgg acggagtgac tttcctaacc aagtaaacaa tgttttagct    960
tttcccggta tatttagagg agcgttggat gtaagagcat cagaaataaa tgatgaaatg   1020
aaaattgctg ctgcttatgc tatagcagaa ttagtttcag aagaagaatt aaaacctgat   1080
tatattatac caaatgcatt tgatttgaga atagctccta aagtagcagc ttatgtagca   1140
aaagcagcaa tagatacagg agtgccttaa aagaaagatg ttacaccaga aatggttgaa   1200
aagcacacaa aaactttgct tggcatttaa                                     1230

SEQ ID NO: 24           moltype = AA  length = 409
FEATURE                 Location/Qualifiers
source                  1..409
                        mol_type = protein
                        organism = Clostridium autoethanogenum
SEQUENCE: 24
MNLRETALKF HKDNEGKIAL KCKVPVKNKE DLTLAYTPGV AEPCLEINKN PECIYDYTSK    60
GNWVAVVTNG TAVLGLGNIG AGAGLPVMEG KSVLFKTFAG VDAFPICLES KDINEIVAAV   120
KLMEPTFGGI NLEDIKAPEC FEIESKLKEV CNIPVFHDDQ HGTAVVSSAC LINALKIVNK   180
KFEDLKIVVN GAGAAGTAIT KLLIKMGTKN VILCDTKGAI YKRRPIGMNK FKDEMAEITN   240
PNLQKGTLAD VLKGADVFLG VSAANCVTEE MVKSMNKDSI IMAMANPNPE ILPDLAIKAG   300
AKVVCTGRSD FPNQVNNVLA FPGIFRGALD VRASEINDEM KIAAAYAIAE LVSEEELKPD   360
YIIPNAFDLR IAPKVAAYVA KAAIDTGVAR KKDVTPEMVE KHTKTLLGI               409

SEQ ID NO: 25           moltype = DNA  length = 1173
FEATURE                 Location/Qualifiers
misc_feature            1..1173
                        note = Codon-adapted nucleotide sequence
source                  1..1173
                        mol_type = other DNA
                        organism = synthetic construct
SEQUENCE: 25
atgaatgtaa agaaaaatc acttaagctg catagagaaa acatggaac aatagaaata      60
gtaggaacaa tgcctttaag aaatggtgat gatcttgcag tagcttatac tcctggagta   120
gctggtcctt gcttagaaat agctaaggat gaagaaaagg cttatgaata tactataaaa   180
ggaaaaacag ttgctgtagt tactaatggt acagctgttc ttggacttgg aaatatagga   240
cctgctgcag gacttcctgt tgtagaagga aaggctttac ttttgaaaag atttgcaaat   300
gtaaatgcta tacctatatg tgtagattct acagatccag atgatatcgt taatacaata   360
aaaaatatag ctccaggatt tggcggcata catctggaag atataaaggc tccagaatgt   420
ttctacatag aagataaact taaggaagaa ttagatatac ctatatacca tgatgatcaa   480
catggtactg ccatcgctgt tttagctgga ttgtataatg cattaaaaat agttaacaaa   540
gatatatcag atataaaagt tgtaataaat ggtgctggtg ctagtggtat agctacagca   600
aaacttctca tatctgcagg agtaaaaaat attgtccttt gtgacattaa tggaatagtt   660
tatgaaggtg acaattgctt aaatgagcct cagaaacaaa tagcaaaagt aactaacaga   720
ggactggcaa agggaacatt aaaagatgct atgaaaaatg cagatgtatt cattggagtt   780
tctgctggta atgtggtaac tggagaaatg gttgaaggta tgaataaaga ttctataata   840
tttgctttag ctaatcctac accagaaatt atgcctgaaa agcaaaaaa ggctggtgct   900
aaagtttatg caacaggaag atctgatttt ccaaaccaaa ttaacaatgt tcttgtattc   960
cctggtatct tcaaaggtgc tctttcagta agggctaagg aaatatgca gaaatgaaa   1020
atagcagctg caaagggact agcaaatcta gtaaagaagg acgagcttaa tgaagaatat   1080
ataataccat cagttttcaa tagaaatgta tgtgatgcag tttccaaggc tgttatggat   1140
gtagcacaaa aaaataataa atttactgca taa                                 1173

SEQ ID NO: 26           moltype = AA  length = 390
FEATURE                 Location/Qualifiers
source                  1..390
                        mol_type = protein
                        organism = Clostridium autoethanogenum
SEQUENCE: 26
MNVKEKSLKL HREKHGTIEI VGTMPLRNGD DLAVAYTPGV AGPCLEIAKD EEKAYEYTIK    60
GKTVAVVTNG TAVLGLGNIG PAAGLPVVEG KALLLKRFAN VNAIPICVDS TDPDDIVNTI   120
KNIAPGFGGI HLEDIKAPEC FYIEDKLKEE LDIPIYHDDQ HGTAIAVLAG LYNALKIVNK   180
DISDIKVVIN GAGASGIATA KLLISAGVKN IVLCDINGIV YEGDNCLNEP QKQIAKVTNR   240
GLAKGTLKDA MKNADVFIGV SAGNVVTGEM VEGMNKDSII FALANPTPEI MPEEAKKAGA   300
KVIATGRSDF PNQINNVLVF PGIFKGALSV RAKEICDEMK IAAAKGLANL VKKDELNEEY   360
IIPSVFNRNV CDAVSKAVMD VAQKNNKFTA                                     390

SEQ ID NO: 27           moltype = DNA  length = 2187
FEATURE                 Location/Qualifiers
misc_feature            1..2187
                        note = Codon-adapted nucleotide sequence
source                  1..2187
                        mol_type = other DNA
                        organism = synthetic construct
SEQUENCE: 27
atgactaact atgaaaaggt aggtaaatta caagtagcaa cggaattata aactttgta      60
aaggaagaag ttttaccagg acttgaaata caaaatgagc aattctggac aaattttgat   120
tcgcttattc atgaacttgc cccagaaaat aaggcacttt tggaaaaaag ggacgagctt   180
cagaagacca tatcagaatg gcatcaaaat aataaaggag aaatagattt tgctaaatac   240
aaagagttct acaagaaaat aggatatctt gaaccagttc cagaagattt caaagttact   300
acagctaatg tagacaatga agtggctaat caggctggtt ctcaattagt tgtacctata   360
```

```
gataatgcaa gatatgctct aaacgctgct aatgcccgct ggggatcact ttatgatgca    420
ttatatggta gtgacgttat aagcgatgag gctggagcag aggctggtgt ccagtataat    480
cctataagag gtcaaaaggt aatagatttt gcaaaaaatt tattagatca agcagctcct    540
cttgcagaag gttctcatgc tgatgtaacc gcctacaaaa ttgttgaagg aaaacttcag    600
gttactttgg aatctggtaa tactgcttta cttcaagatg aatccaaatt tgtaggatat    660
aatggaagtg aggatgcacc gacggcagta ctccttgtaa acaacgggct tcatattgaa    720
atagcaatag ataaaaataa tcctatagga aatctgacaa aggctggtgt taaggacctt    780
gttttagagg ctgcactttc gactttaatg gactgtgagg attcaattgc tgcagtagat    840
gcagaggata aagtaggcgt atatagaaat tggcttggac ttatgaaagg agatttagaa    900
agcactttta agagaggatc aaaaactgtt acaagaagc tgaacgctga cagaacctat    960
acaggtgatg gtaaacaatt aactctcagg ggacgtagtc ttatgtttgt gagaaatgtg    1020
ggacatttaa tgactaacaa tgctatattg gatgaaaacg gaaatgaagt tccagaaggt    1080
atcttagatg gagtattaac aagtcttata gcaactcata atttcaaaga aaatgcgag    1140
ttcaaaaaca gccttcacaa gagtatatat attgttaaac caaaaatgca ttcaccagca    1200
gaagcagctt ttgctaataa gttatttgat agaatagaag atttacttgg agtagaaaga    1260
aatactatta aaattggtgt tatggatgaa gaaagaagaa tgtcattaaa tttaaagtct    1320
gcaataaatg aagttaaaga agaatagct tttattaata caggattcct tgatagaact    1380
ggagatgaaa tacacacttc tatggaagca ggacctgtaa ttagaaagg tgacatgaag    1440
acttcagaat ggctttcttc ttatgaatca gctaatgtag ctgtaggaat aggagcagga    1500
ttaccaggac atgcacagat tggaaaggga atgtgggcaa tgccagacct tatggcagca    1560
atgcttgaac aaaaaatagc acatcctaag gctgggctt caacagcatg ggttccttct    1620
ccaactgcag ctatattgca tgcccttcac tatcatgagg taaacgttaa agaagttcag    1680
gctggtattg atagttctat agattataga gatggaatat tagatatacc tcttgctcca    1740
aatgcagact ggagcgctga ggaagttcag tctgaattag acaacaatgc acaaggaata    1800
cttggatatg ttgtgcgctg gattgatcaa ggtgtaggat gcagcactgt accagatatt    1860
aatgatgttg gtcttatgga agatagggct actctcccgta tttcaagtca gcatatagct    1920
aattggctta gacatggtgt gtgtactaaa gaacaggtag aggaaacttt agagagaatg    1980
gctaaagttg tagaccaaca aaatgcagat gatgaacttt atcaaccaat ggcaccaaac    2040
tacgacgatt caattgcatt ccaggctgca tcagactaa ttttcaaagg agcagagcaa    2100
cctagtgggt atactgagcc aatcctacat gcaagaagaa tagaagcaaa ggctaaggct    2160
aaacaaaaag caacagtaca gaattag                                      2187

SEQ ID NO: 28          moltype = AA  length = 728
FEATURE                Location/Qualifiers
source                 1..728
                       mol_type = protein
                       organism = Sporosarcina sp. P30
SEQUENCE: 28
MTNYEKVGKL QVATELYNFV KEEVLPGLEI QNEQFWTNFD SLIHELAPEN KALLEKRDEL     60
QKTISEWHQN NKGEIDFAKY KEFLQEIGYL EPVPEDFKVT TANVDNEVAN QAGSQLVVPI    120
DNARYALNAA NARWGSLYDA LYGSDVISDE AGAEAGVQYN PIRGQKVIDF AKNLLDQAAP    180
LAEGSHADVT AYKIVEGKLQ VTLESGNTAL LQDESKFVGY NGSEDAPTAV LLVNNGLHIE    240
IAIDKNNPIG KSDKAGVKDL VLEAALSTLM DCEDSIAAVD AEDKVGVYRN WLGLMKGDLE    300
STFKRGSKTV TRKLNADRTY TGDGKQLTLR GRSLMFVRNV GHLMTNNAIL DENGNEVPEG    360
ILDGVLTSLI ATHNFKENAE FKNSLHKSIY IVKPKMHSPA EAAFANKLFD RIEDLLGVER    420
NTIKIGVMDE ERRMSLNLKS AINEVKERIA FINTGFLDRT GDEIHTSMEA GPVIRKADMK    480
TSEWLSSYES ANVAVGIGAG LPGHAQIGKG MWAMPDLMAA MLEQKIAHPK AGASTAWVPS    540
PTAAILHALH YHEVNVKEVQ AGIDSSIDYR DGILDIPLAP NADWSAEEVQ SELDNNAQGI    600
LGYVVRWIDQ GVGCSTVPDI NDVGLMEDRA TLRISSQHIA NWLRHGVCTK EQVEETLERM    660
AKVVDQQNAD DELYQPMAPN YDDSIAFQAA SDLIFKGAEQ PSGYTEPILH ARRIEAKAKA    720
KQKATVQN                                                             728

SEQ ID NO: 29          moltype = DNA  length = 2181
FEATURE                Location/Qualifiers
misc_feature           1..2181
                       note = Codon-adapted nucleotide sequence
source                 1..2181
                       mol_type = other DNA
                       organism = synthetic construct
SEQUENCE: 29
atggaaaatt atgtaaaagt aggctcatta caagtagcaa gtgaacttta tgaatttatt     60
aactcagagg ctctacctgg aagtgatttg aaccagaga attttggag tggatttgaa    120
aaattagttc atgatcttac tcctaaaaat aagcaacttc ttgcccgtag agatgaaata    180
caaagtaaaa taaatacttg gcacagagag aacaatcaat cctttaactt cgaaacttat    240
aagagtttcc tagaagaaat aggatattta gaaacagaag tagaggattt tgatatcaaa    300
acagaaggtg tagatgatga atagctgta caggctggtc cacggcttgt agtacctgta    360
aacaatgcaa gatatgcaat aaatgctgca atgctagat ggggtcact atatgatgct    420
ttatatggta atgatgtcat aagtgaagaa ggcgcgcca cacgtgcagg cggctataat    480
cctgttagag gaagaaaggt aatagatttt gcaagagat ttttagatca agcagtccct    540
cttaatggtt tttcccacaa agaagcaaca agttatttag tagatggg aaaacttaca    600
gttaagctga aaatggaga atctacagga ttaaagaatg aggaaaaatt tgcaggatat    660
cagggtcac cggaacaacc ttctgcagtt cttttaaaga acaatggcct tcactttgaa    720
attcaaatag atagatctca tccaatagga caaactgatg aagcgggagt taagatttg    780
ttacttgaat ctgctgtaac tactataatg gactgtgaag attcagttgc tgcagtagat    840
gcagaagaca aagttttagt ttatagaaat tggcttggat taatgaaagg ggatttggaa    900
gcatctttct caaagggtaa taatcaatg atgagaaaat taaatgcaga cagaaaatac    960
tcctctccaa ctgcggcga attaagtttg aaggagaaga gttgttatt tgtaagaaat    1020
gttggccatc ttatgtctat aaatgcaata cttgatcaag acgttgaaga aatacaggaa    1080
ggtatttag acactgttat gacatcgctt atagctaaac atcattact tggaaacggt    1140
```

```
tcataccaaa atacttcaaa gggttctgtt tatatagtta aacctaagat gcatggttct  1200
gaagaagtag catttgcaaa tgaattattt gatagagtag aagatttact tgaattacag  1260
agaaatacat tgaaaatagg agtaatggat gaagaaagaa ggacatctct aaacttaaaa  1320
gcatgtatta gacaagttaa agatcgtatt gtatttataa atacaggatt ccttgacagg  1380
acaggtgatg agattcatac aagtatgaaa gcaggacctg tagtaagaaa aaatgaaatg  1440
aaatcttcaa aatggcttca agcctatgaa caaagtaatg ttattgctgg attatcatca  1500
ggatttcaag gacaggcaca aataggaaaa ggaatgtggg ctatgccaga tttaatgaaa  1560
gagatgatgg aacagaagat aggacatcta aaaactggtg ctaatactgc ctgggttcca  1620
agccctacag cggctacatt gcatgcactt cattatcatc aagttgacat tacaaaagtt  1680
caagatgaac gtgccaacga taaaagagat ttaagagatg atattttaga atttccagta  1740
gtaactaatc cacagtggac gcccgaagaa atacagaatg aattagataa taatgcacaa  1800
tccatacttg gatacgttgt tagatgggtt gaacagggag ttggttgttc aaaagtacct  1860
gacataaaca atgttggatt aatgaagac agggctacat taagaataag cagtcagcat  1920
gtagctaatt gcttcatca tggaaatatgt aagaaggaac aagttattga aacacttcaa  1980
aggatggcaa aggttgtaga tgaacaaaat gctggaaatt tggcttatag gcctatggca  2040
gcaaattatg atgactcagt agcatttcag gctgcctgtg atttaatttt acaaggatat  2100
gatcagccat ctggatacac agagcctata ctacacagaa ggcgtataga ggctaaggct  2160
aaatttgcaa ttaaacaata a                                            2181

SEQ ID NO: 30          moltype = AA   length = 726
FEATURE                Location/Qualifiers
source                 1..726
                       mol_type = protein
                       organism = Bacillus sp. cl95
SEQUENCE: 30
MENYVKVGSL QVASELYEFI NSEALPGSDL EPEKFWSGFE KLVHDLTPKN KQLLARRDEI   60
QSKINTWHRE NNQSFNFETY KSFLEEIGYL ETEVEDFDIK TEGVDDEIAV QAGPQLVVPV  120
NNARYAINAA NARWGSLYDA LYGTDAISEE GGATRAGGYN PVRGEKVIDF AREFLDQAVP  180
LNGFSHKEAT SYLVVDGKLT VKLKNGESTG LKNEEKFAGY QGAPEQPSAV LLKNNGLHFE  240
IQIDRSHPIG QTDEAGVKDL LLESAVTTIM DCEDSVTAVD AEDKVLVYRN WLGLMKGDLE  300
ASFSKGNKSM MRKLNADRKY SSPTGGELSL KGRSLLFVRN VGHLMSINAI LDQDGEEIQE  360
GILDTVMTSL IAKHTLLGNG SYQNTSKGSV YIVKPKMHGS EEVAFANELF DRVEDLLELQ  420
RNTLKIGVMD EERRTSLNLK ACIRQVKDRI VFINTGFLDR TGDEIHTSME AGPVVRKNEM  480
KSSKWLQAYE QSNVIAGLSS GFQGQAQIGK GMWAMPDLMK EMMEQKIGHL KTGANTAWVP  540
SPTAATLHAL HYHQVDITKV QDERANDKRD LRDDILEFPV VTNPQWTPEE IQNELDNNAQ  600
SILGYVVRWV EQGVGCSKVP DINNVGLMED RATLRISSQH VANWLHHGIC KKEQVIETLQ  660
RMAKVVDEQN AGNLAYRPMA ANYDDSVAFQ AACDLILQGY DQPSGYTEPI LHRRRIEAKA  720
KFAIKQ                                                             726

SEQ ID NO: 31          moltype = DNA   length = 1623
FEATURE                Location/Qualifiers
misc_feature           1..1623
                       note = Codon-adapted nucleotide sequence
source                 1..1623
                       mol_type = other DNA
                       organism = synthetic construct
SEQUENCE: 31
atgtcagcac cagcaccatc aactttagct atagtagatg cagaaccatt accaagacaa   60
gaggaagtgc ttacagatgc tgcacttgct tttgttgctg aattgcacag aagatttaca  120
ccacgtagag atgaattatt agcaagaagg gcagaaagaa gagcggaaat agctagaact  180
tctacactgg atttcttgcc agaaacagca gctatacgtg ctgatgacag ctggaagtta  240
gcccctgctc cagctgctct caacgacaga agagtagaaa taacaggacc tacagataga  300
aagtgactta taaacgctct aaatagtggt gctaaagttt ggctagcaga ttttgaagat  360
gcttcagctc caacttggga aaatgttgtt ttgggacaat taaatcttgc atcagctat   420
actagatcca ttgactttac agatgagaga actggaaaga gttatgcact tcgtccggat  480
gctgaattag caacggtagt tatgaggcct agaggttggc atcttgatga agacatctt   540
caggtagacg gtaggcctgt acctggtgca ttagtggact ttgggcttta tttttttcat  600
aatgcacaaa gattgctcga tctaggtaag ggaccatact tctatttacc taaaactgaa  660
tctcatcttg aagcaagact atggaatgaa gtatttgtat ttgcacagga ttatgtaggt  720
ataccacagg gaactgtcag agcaactgta cttataatgaa ctattacagc agcctatgaa  780
atggaagaaa tactttacga gcttagggac catgcaagtg gcttaaatgc aggaagatgg  840
gattatctat tttccatagt taaaaatttt agggacggcg cgctaaatt tgttttacct  900
gatagaaatg cagttactat gactgctcca tttatgcgtg cttatacaga attattagta  960
cgtacctgtc acaagagagg agcacatgct aataggccgta tggcagcaga taggtacctagt 1020
agaagggatg cagaggtaaa taagtagcca tttgaaaaag taagagcaga taaggaccgt  1080
gaggctggtg atggttttga tggcagctgg gttgctcatc cggatcttgt acctatagca  1140
atggagagtt ttgataaggt acttggagat aaaccaaacc aaaaggacag gcttagaaa  1200
gatgtagatg taaaagcagc tgattaatt gccgtagatt cacttgaggc taaacctacc  1260
tatgcaggat tagttaatgc agttcaagta ggtattaagc atgaagatgc aggcaatgg  1320
ggattaggtg ctgtagctat atttaactta atggaagatg ctgctactgc agaaaatca  1380
aggagtcaga tttggcaatg gattaatgct gaggtagttc ttgataatgg tgaacaggta  1440
acagctgatt tagcccgtaa agtagctgca aagaattgg caggaataag agcagaaata  1500
ggtgaagagg catttgcagc gggcaactgg caacaggctc atgatttgtt acttactgta  1560
tctttagatg aagattatgc agattttttg actttaccag cttatgaaca acttaaagga  1620
taa                                                               1623
```

```
SEQ ID NO: 32              moltype = AA   length = 540
FEATURE                    Location/Qualifiers
source                     1..540
                           mol_type = protein
                           organism = Streptomyces coelicolor
SEQUENCE: 32
MSAPAPSTLA IVDAEPLPRQ EEVLTDAALA FVAELHRRFT PRRDELLARR AERRAEIART    60
STLDFLPETA AIRADDSWKV APAPAALNDR RVEITGPTDR KMTINALNSG AKVWLADFED   120
ASAPTWENVV LGQLNLASAY TRSIDFTDER TGKSYALRPD AELATVVMRP RGWHLDERHL   180
QVDGRPVPGA LVDFGLYFFH NAQRLLDLGK GPYFYLPKTE SHLEARLWNE VFVFAQDYVG   240
IPQGTVRATV LIETITAAYE MEEILYELRD HASGLNAGRW DYLFSIVKNF RDGGAKFVLP   300
DRNAVTMTAP FMRAYTELLV RTCHKRGAHA IGGMAAFIPS RRDAEVNKVA FEKVRADKDR   360
EAGDGFDGSW VAHPDLVPIA MESFDKVLGD KPNQKDRLRE DVDVKAADLI AVDSLEAKPT   420
YAGLVNAVQV GIRYIEAWLR GLGAVAIFNL MEDAATAEIS RSQIWQWINA EVVLDNGEQV   480
TADLARKVAA EELAGIRAEI GEEAFAAGNW QQAHDLLLTV SLDEDYADFL TLPAYEQLKG   540

SEQ ID NO: 33              moltype = DNA   length = 2190
FEATURE                    Location/Qualifiers
misc_feature               1..2190
                           note = Codon-adapted nucleotide sequence
source                     1..2190
                           mol_type = other DNA
                           organism = synthetic construct
SEQUENCE: 33
atgaccaatt atgaaaaagt aggtaagtta caggtagcaa ctgaattagt aaattttgta    60
aatgaggaag tattacctgg cttagaaata cagaaagatc aattctggac caatttcgat   120
tcactgatcc atgaattagc tccagaaaat aaagcacttt tagaaaaaag atcagaactt   180
cagaatgcaa tttctgaatg gcatcagcaa aataaaggac aaatagatgc tgcaaaatat   240
aaggaatttc tggaagaaat aggatattta gagccagttg ctgaagattt tcaggtaact   300
acaagcaatg tagataatga aattgctaat caggctggtt ctcaattagt tgtaccaatt   360
gataatgcaa gatatgcttt aaatgcagct aatgctagat ggggttcact atatgatgca   420
ttatatggaa cagatgttat atctgatgaa gatggagcac aggcaggagc agagtataat   480
cctaaaagag gacaaaaagt tattgctttt gctaagaatt tacttgatca ggctgctcct   540
ttagctgagg gatctcaaag acagtgagct gcttataaaa ttgcagatgg aacattacag   600
gttactttag aaaatggaaa aacaactgca cttcaggatg aaagcaagct ggcaggatat   660
aacggaagtg aagatgcccc agaagcagtg ttactagtaa ataatggact tcatattgaa   720
attgcaatag atagaaatca tcctataggt aaagatgata aggctggtgt aaaagaccta   780
gtgcttgaag cagctttatc tacattaatg gattgtgaag atagtatagc agcagtagat   840
gcagaagaca aagtaggtgt ttataaaatg ggttagggc ttattgaaagg agatttagag   900
gcttcattta agaggaaa taagacagta actagaagaa tgaatgcaga tagaaaaatat   960
aaaactgcag atggtaaaga atttacattg cacggaaggt cattgatgtt tgtaagaaat  1020
gtaggacatc ttatgacaaa taatgcaatc ctagatgaaa acgaaatgaa agttccagaa  1080
ggtatacttg atggagttat aacatcttta attgcaactc ataacttcaa atcagataca  1140
gaatttaaga attcaagaca cggatcaatt tatagtatta agcctaaaat gcatagtcca  1200
gcagaggctg cttttgcaaa taaattattc gatagaatag aggatttatt agggttagag  1260
agaaatacta aaaaatagg attgatggac gaggaacgta gaatgtcctt aaatcttaaa  1320
tctgctataa atgaagttaa agaacgtatt gcttttataa atactggatt ccttgataga  1380
acaggagatg aaatacacac tagcatggaa gcaggacctg taataagaaa agcagacatg  1440
aaggcttcaa actggttaag ttcctatgaa gcaagcaatg ttgcagtagg tataaaagca  1500
ggattaccgg gacatgcaca aataggtaaa ggaatgtggg caatgccaga tatgatggca  1560
gcaatgttag aacagaaggt agctcatcca aaagcaggag catccactgc atgggtacca  1620
tcaccaactg cagctaccct tcatgcacta cattatcatg aagtaaatgt aaaagatgtt  1680
caggctggaa tagattcctc tgtagattat agggatggaa tattagagat acctttggca  1740
ccgtcggtag attggacacc agaagaagtt caatctgaat tagataataa tgcccaagga  1800
atattaggat atgtagtaag agtgatagat caaggtgtga tgtgttcaaa ggtaccagat  1860
ataaatgatg tgggccttat ggaagacagg gcaacattac gaatatctag tcagcatata  1920
gcaaattggc ttagacacgg aatatgtaca aagaacaag ttcaagaaac attagaaaga  1980
atggctaaag ttgtagatgg tcaaaatgca gatgacgaat tgtaccaacc tatggcacca  2040
aattatgatg attctatagc attccaggct gcttgtgact aatatcaa aggagcagaa  2100
cagccaagtg gatatactga accaattcta catgctagaa gaatagaggc taaggctaaa  2160
gccaagcaaa aagcaactgt acagaattag                                   2190

SEQ ID NO: 34              moltype = AA   length = 729
FEATURE                    Location/Qualifiers
source                     1..729
                           mol_type = protein
                           organism = Sporosarcina sp. P35
SEQUENCE: 34
MTNYEKVGKL QVATELVNFV NEEVLPGLEI QKDQFWTNFD SLIHELAPEN KALLEKRSEL    60
QNAISEWHQQ NKGQIDAAKY KEFLEEIGYL EPVAEDFQVT TSNVDNEIAN QAGSQLVVPI   120
DNARYALNAA NARWGSLYDA LYGTDVISDE DGAQAGAEYN PKRGQKVIAF AKNLLDQAAP   180
LAEGSHADAA AYKIADGTLQ VTLENGKTTA LQDESKLAGY NGSEDAPEAV LLVNNGLHIE   240
IAIDRNHPIG KDDKAGVKDL VLEAALSTLM DCEDSIAAVD AEDKVGVYRN WLGLMKGDLE   300
ASFKRGNKTV TRRMNADRKY KTADGKEFTL HGRSLMFVRN VGHLMTNNAI LDENGNEVPE   360
GILDGVITSL IATHNFKSDT EFKNSRHGSI YIVKPKMHSP AEAAFANKLF DRIEDLLGLE   420
RNTIKIGLMD EERRMSLNLK SAINEVKERI AFINTGFLDR TGDEIHTSME AGPVIRKADM   480
KASNWLSSYE ASNVAVGIKA GLPGHAQIGK GMWAMPDMMA AMLEQKVAHP KAGASTAWVP   540
SPTAATLHAL HYHEVNVKDV QAGIDSSVDY RDGILEIPLA PSVDWTPEEV QSELDNNAQG   600
ILGYVVRWID QGVGCSKVPD INDVGLMEDR ATLRISSQHI ANWLRHGICT KEQVQETLER   660
```

```
MAKVVDGQNA DDELYQPMAP NYDDSIAFQA ACDLIFKGAE QPSGYTEPIL HARRIEAKAK  720
AKQKATVQN                                                        729

SEQ ID NO: 35           moltype = DNA  length = 2181
FEATURE                 Location/Qualifiers
misc_feature            1..2181
                        note = Codon-adapted nucleotide sequence
source                  1..2181
                        mol_type = other DNA
                        organism = synthetic construct
SEQUENCE: 35
atggtagcgt ataaacaaat aggaaaactt caggtagctc cagttttata taattttata   60
aatgaagaag cattacctga acaggactt caggaagaag cgttctgggc gggttttgaa   120
cagttaattc atgaattgac tcctgaaaat aaggctctac ttgctaaaag agatgaatta  180
caagcaaaac taaacagatg gtacagagaa aataggact cattcgattt tgaagcatac   240
aaggctttt taacatctat tggatatctt gaagcagatg ttgcagattt tcaaatatca   300
actgctaatg tagatgatga aattgcttta caggctggtc ctcaattagt tgtaccagta   360
aataatgcaa gatatgctat aaatgctgca aatgcaagat ggggttcttt gtatgatgcc   420
ctctacggaa ctgatgcaat atcttctgaa aatggagcag gcgtgcaaag tcaatataat   480
cctattcgag gtgagaaggt aataactttt gctaaaagct ttttaaatca cactattccc   540
ttaaaagaag gaaagcatga agatgtagtt caatacgtgg taacaaataa gatggaagca   600
ttgcttcaag atggaactac tacagagtta aaagaaccat caaatggggt tggctatcaa   660
ggggatggtt caaatccatc agcactttta tttaagaata atggacttca ctttgaaata   720
cagatagata gacaggatgc cataggtaaa tcagatgatg ctggtgtaaa agatgtattg   780
ttagagtcag ctgtaacaac tattatggat tgtgaagata gtgtagctgc cgtagatgca   840
gaagataaag ttgaagtata caggaactgg ttgggattaa tgaaaggtga tctgaaggca   900
agatttaaga aaggtgcaaa actatatgac agaacattga atgatgacag acagtataaa   960
actgcaaatg gagatactgt aacattatca ggtagatcct taatgtttgt tagaaatgta  1020
ggacatttga tgtcaaattc tgctatttta gatgcaaatg gagatgaaat acaggaagga  1080
atacttgatt caataataac ttcacttata gctaaacata ctttattagg aacaggaaaa  1140
taccaaaaca gccaaaaggg aagtgtttat attgtaaaac ctaaaatgca tggttcagaa  1200
gaagtagctt ttgctaataa acttttcgat agagttgaag atcttgtagg actaccaaga  1260
catacttta aaataggtgt catggatgaa gaaagaagaa cttcattaaa tttaaaagca  1320
tgcatagaga aagtaaagaa tagggtagct ttataaaca ctggttttt ggatagaact  1380
ggagatgaaa tgcataccag ggagttatga taagaaaaaa tgacatgaaa  1440
tcaagtgttt ggttggcagg atacgaaaaa agcaatgtat taaccggatt agcttcaggc  1500
tttcagggaa agcccagat aggtaaaggc atgtgggcaa tgcctgatct tatggcagaa  1560
atgttaaaac aaaaagtagg acatcttcag gctggagcca atacagcatg ggtaccttca  1620
ccaacagcag ccactttaca tgcctgcac tatcatgaag tcgtagt gatgtacag  1680
aatcaacttg ctaacaattc tacaaatttg agggatgata ttttacaggt acctcttgca  1740
aaagagccaa attggacaaa agaggaagtt caacaggaat tggacaacaa tgcgcaaggc  1800
atttaggat acgtggtaag atgggtagac caaggtatag ttgttctaa agtgcctgac  1860
ataaatgcta ttggacttat ggaagatagg gcaactctaa gaatatcatc acaacatgta  1920
gcaaattggc ttcatcacgg aatatgtact aaggaacagg tacttgctac tcttcagaga  1980
atggccaaag tagtggattc tcaaaatgct ggtgatgcta attatcagcc aatggctcct  2040
cactacgagg aatctatagc attccaggca gcctgtgatt tagtattcaa aggctatgat  2100
cagccaaatg gatatacaga gcctatattg catgcaagaa gaatagaggc taaggcaaaa  2160
caagcaatag aacagaaata a                                            2181

SEQ ID NO: 36           moltype = AA  length = 726
FEATURE                 Location/Qualifiers
source                  1..726
                        mol_type = protein
                        organism = Bacillus sp. VT 712
SEQUENCE: 36
MVAYKQIGKL QVAPVLYNFI NEEALPETGL QEEAFWAGFE QLIHELTPEN KALLAKRDEL   60
QAKLNRWYRE NRDSFDFEAY KAFLTSIGYL EADVADFQIS TANVDDEIAL QAGPQLVVPV  120
NNARYAINAA NARWGSLYDA LYGTDAISSE NGAVQSQYN PIRGEKVITF AKSFLNHTIP  180
LKEGKHEDVV QYVVTNKMEA LLQDGTTTEL KEPSKWVGYQ GDGSNPSALL FKNNGLHFEI  240
QIDRQDAIGK SDDAGVKDVL LESAVTTIMD CEDSVAAVDA EDKVEVYRNW LGLMKGDLKA  300
RFKKGAKTMT RTLNDDRQYK TANGDTVTLS GRSLMFVRNV GHLMSNSAIL DANGDEIQEG  360
ILDSIITSLI AKHTLLGTGK YQNSQKGSVY IVKPKMHGSE EVAFANKLFD RVEDLVGLPR  420
HTLKIGVMDE ERRTSLNLKA CIEKVKNRVA FINTGFLDRT GDEMHTSMEA GVMIRKNDMK  480
SSVWLAGYEK SNVLTGLASG FQGKAQIGKG MWAMPDLMAE MLKQKVGHLQ AGANTAWVPS  540
PTAATLHALH YHEVSVVDVQ NQLANNSTNL RDDILQVPLA KEPNWTKEEV QQELDNNAQG  600
ILGYVVRWVD QGIGCSKVPD INDVGLMEDR ATLRISSQHV ANWLHHGICT KEQVLATLQR  660
MAKVVDSQNA GDANYQPMAP HYEESIAFQA ACDLVFKGYD QPNGYTEPIL HARRIEAKAK  720
QAIEQK                                                            726

SEQ ID NO: 37           moltype = DNA  length = 2181
FEATURE                 Location/Qualifiers
misc_feature            1..2181
                        note = Codon-adapted nucleotide sequence
source                  1..2181
                        mol_type = other DNA
                        organism = synthetic construct
SEQUENCE: 37
atggcaaact atagaaaaat aggaaattta caggtagacg aggcacttca tcaatttctt   60
caaaagagg ctttaccagg tacaggactt gaagaaaagg cttttggaa tggatttgag  120
```

-continued

```
aaacttatag aagtattaac tccagaaaat aaaagacttc ttgcaaagag agaagagctt   180
caaagagaac ttgatagata tcactcagag aaaagagatg attttcatt tgaagcatac    240
aagcaatttt tacttgattt aggatatctt ttacctgaac ctggagagtt caaaataagg   300
acagaaaatg tagatgatga gattgctctt caagcaggac acaattggt cgttcctgtc    360
aataattcaa gatattcaat aaacgcagca aatgctcgct ggggtagctc atatgatgcc   420
ttgtatggaa cagatgctat aagcgaagaa ggcggcgctg agagatctat agagtacaat   480
agagttagag gaaataaagt tatagaattt gcaagggat tcttagatca ggcagctgca    540
cttgacggtg catcccacaa agaagcagtt agatattccg caaggaagg ttctttagtt    600
ataactttga aagatggaag ttcctctaaa ttaaaagatc aagaggcttt tgctgggtat   660
agaggagata aagaccatcc agaggctgta ttacttaaac atcatggatt gcatttttgaa  720
atacagatag ataggcaag tgacatcgga aagtcagatc ctgctggtat taagatata    780
ttattggaag cagcagtaac tgttataatg gattgtgaag attctgtagc tgctgtagat   840
gctgaagata aggtacttgt atatagaaat tggcttggat tgatgaaagg agaactttcc   900
gcagatttta gcaagggcgg caaaataata tcaagaaaat taatggtgt acgtcattat    960
agagatcctg aaggaaatct ttttcattg cctggaagat cattacttt cgtaagaaat    1020
gtaggtcatc ttatgactaa cccagctgtt ttggataaag aaggaaatga agtttatgaa  1080
ggtattctag atgcagtatt cacatcttta gctgaatgc acagcttatt aaatactgaa   1140
gagcccgcaa actcaagaaa aggtatcta tatatagtta agcaaaaat gcacgggcca    1200
gaagaagttg cttatgcagg agaactattt gataaaactg aagatcttt aggacttgac   1260
agaaacactc ttaaaattgg attaatggat gaagaaagga gaacttcatt aaatttaaag   1320
tcttgtataa aagaagtaaa agatcgtatt gtatttataa atacaggttt tttagataga   1380
acaggtgatg aaatacattc atctatgaa gcaggaccta tggtgagaaa gggagaaatg   1440
aaaaaatcaa actggcttca ggcttatgaa acttcaaatg tttccacggg tctttcagca   1500
ggattttctg gtaaggcaca gatcggaaag ggtatgtggg caatgccaga taaaatgaaa   1560
gaaatgctgg aacagaaagg tgcccagttg aaaactggtg ctaatacagc atgggttcca   1620
tctccatctg cagcagtcat tcatgccta cattatcatc aaataaatgt taaggtata    1680
caagagaaaa aatgccaaaa tccgtctctt tatcgtgacg aaatgctgtc aataccagtt   1740
gaaacctgtg gttcttggtc aagtgaagaa attcaagttg aaatagaaaa taatgcacaa   1800
ggtatattgg gatacgtagt tagatgggta gaacagggta taggatgctc taaagtccct   1860
gatattcatg atgtaggcct catggaagat agagcaactt taagaataag tagtcagcat   1920
cttgctaatt ggatacatca caagatagtt tcaagagaac aggtaatgaa tgcttttaaaa  1980
aagatggcta aaattgtaga tgcacaaaat gaaaatgaac cgggctataa aagaatgagc   2040
gatgacttct ctacatctgt tgcattccag gctgcctgtg aattaatatt tgaaggcaga   2100
aatcaaccta atggatatac ggaacctatt ctccacaaga gaagattaga ggctaaatcc   2160
aaaatggcag taagacaata a                                            2181
```

SEQ ID NO: 38          moltype = AA   length = 726
FEATURE                Location/Qualifiers
source                 1..726
                       mol_type = protein
                       organism = Bacillus infantis NRRL B-14911
SEQUENCE: 38
```
MANYRKIGNL QVDEALHQFL QKEALPGTGL EEKAFWNGFE KLIEVLTPEN KRLLAKREEL    60
QRELDRYHSE KRDDFSFEAY KQFLLDLGYL LPEPGEFKIR TENVDDEIAL QAGPQLVVPV   120
NNSRYSINAA NARWGSLYDA LYGTDAISEE GGAERSIEYN RVRGNKVIEF AKGFLDQAAA   180
LDGASHKEAV RYSAKEGSLV ITLKDGSSSK LKDQEAFAGY RGDKDHPEAV LLKHHGLHFE   240
IQIDRASDIG KSDPAGIKDI LLEAAVTVIM DCEDSVAAVD AEDKVLVYRN WLGLMKGELS   300
ADFSKGGKII SRKLNGVRHY RDPEGNLFSL PGRSLLFVRN VGHLMTNPAV LDKEGNEVYE   360
GILDAVFTSL AGMHSLLNTE EPANSRKGSI YIVKPKMHGP EEVAYAGELF DKTEDLLGLD   420
RNTLKIGLMD EERRTSLNLK SCIKEVKDRI VFINTGFLDR TGDEIHSSME AGPMVRKGEM   480
KKSNWLQAYE TSNVSTGLSA GFSGKAQIGK GMWAMPDKMK EMLEQKGAQL KTGANTAWVP   540
SPSAAVLHAL HYHQINVKGI QEKECQNPSL YRDEMLSIPV ETCGSWSSEE IQVEIENNAQ   600
GILGYVVRWV EQGIGCSKVP DIHDVGLMED RATLRISSQH LANWIHHKIV SREQVMNALK   660
KMAKIVDAQN ENEPGYKRMS DDFSTSVAFQ AACELIFEGR NQPNGYTEPI LHKRRLEAKS   720
KMAVRQ                                                             726
```

SEQ ID NO: 39          moltype = DNA   length = 855
FEATURE                Location/Qualifiers
misc_feature           1..855
                       note = Codon-adapted nucleotide sequence
source                 1..855
                       mol_type = other DNA
                       organism = synthetic construct
SEQUENCE: 39
```
atgtatttag tagataaaga agtaattcat gaaacatttg caaaggttc agtagtaaat     60
tataatgata attatattaa gattgacttt gaatcaggcg caaagaatt tgtatttcct    120
gacgtatttg ggaaatatat gactcttgta gatcaggaag cagtaaactt agttaatatg    180
aaaatacaga aagagaaga agaaaagaaa aaagaggaac ttaagttaat taaagaaaa     240
gatcttgaa gagaaagaca gcatatactg gagcaaaaa aaactatgca atccaggaaa     300
attcatccaa acaacaggt agtattctg tgtgaaaccg gagaggaaga taaatatt      360
actgagggta ggatatttat aggtaaggta aagagtggag aaaataaggg tcagccgaag   420
agattagcaa gaatgacctg gaaatcaggc tgcttactaa caaggcgtga accaggtatg   480
cctgaaaaag acagaaggat attaggagta tttatggctg aagaaggttt caatggtcaa   540
acctgtaagg atggctatat tccagcccat cctgaataca aacttagact tagtgaacaa   600
gaatcagata aaatgttatt ttggaattat tatataaata agaacttccc tactagaatg   660
acttggaatt caggcagaca gagatatttt aacaatattt ggatggcaca aatacttcaa   720
gatattgtaa gctaaaaaaa taaacctgaa gaaagggaaa atgcacagag attctttgaa   780
cacttctgta agttaaccca tataaatgaa gataaacttc ctaaggcaaa tggtgccttg   840
atgcaaattc aataa                                                   855
```

-continued

```
SEQ ID NO: 40           moltype = AA  length = 284
FEATURE                 Location/Qualifiers
source                  1..284
                        mol_type = protein
                        organism = Clostridium cochlearium
SEQUENCE: 40
MYLVDKEVIH ETFGKGSVVN YNDNYIKIDF ESGAKKFVFP DVFGKYMTLV DQEAVNLVNM  60
KIQKREEEKK KEELKLIKEK DLERERQHIL EQKKTMQSRK IHPKQQVVFW CETGEEDKIF  120
TEGRIFIGKV KSGENKGQPK RLARMTWKSG CLLTRREPGM PEKDRRILGV FMAEEGFNGQ  180
TCKDGYIPAH PEYKLRLSEQ ESDKMLFWNY YINKNFPTRM TWNSGRQRYF NNIWMAQILQ  240
DIVSLKNKPE ERENAQRFFE HFCKVNHINE DKLPKANGAL MQIQ                   284

SEQ ID NO: 41           moltype = DNA  length = 2178
FEATURE                 Location/Qualifiers
misc_feature            1..2178
                        note = Codon-adapted nucleotide sequence
source                  1..2178
                        mol_type = other DNA
                        organism = synthetic construct
SEQUENCE: 41
atgactaact ataaacaagt aggcaattta aaagtagcac cagtactata tcaattcata  60
aatgaagaag cattaccggg cagtggactt tccacggaaa acttttggtc tgattttgag  120
gctttagtaa ctgagcttac tcctgttaat aaaagactcc ttgaaaaaag ggatcagctt  180
caggcacaaa taaatgcatg gcatcaagaa aatccagatg gtgatttctc tgaatacaag  240
agtttcctaa ctcgtattgg atatcttgag gataaaacag aggatttttt aattggaacg  300
gaaggtgttg acagtgaaat tgcttatcag gctggtcctc aattagtggt tccggtgaat  360
aacgcaaggt atgcaataaa tgctgctaat gcaagatggg gaagtttgta tgatgcttta  420
tatggcactg atgctatttc agaagaaaat ggtgcgtcaa gaactagttc ctacaatcct  480
attaggggag aaaaagttat agcttttgca aaaaatttcc ttgatgaagt tgtaccttta  540
gtccagagct ctcatgcaga ggttgttcaa tacagtttgg aaaatgaaaa attagtagca  600
caattaaatg atggtagctt aacagaactt caagaagaag aaaaattcgt tggatatcag  660
ggagaagaag aatcaccaga tgccttgtta ttcaaaaaca atggacttca ttttgaagtt  720
caaatagata gaacagattc cataggaaaa acagacgatg caggagttaa agatatactt  780
atggaagcag cacttacaac tataatggat tgcgaagatt ctgtagctgc tgttgatgca  840
gaagacaagg ttgacgtgta tagaaactgg ttaggtctta tgaaaggaga tttaactagt  900
acatttaaga agggatctca aaatatgaca agaagattaa atccggatag aacttatata  960
agtccagata agaaaaagat attattgtcg ggaagatcac ttatgtttgt aagaaatgtt  1020
ggacatctta tgactaattc tgctgtatta gatagaaatg gtaacgaaat atacgagggt  1080
attttggatt ctgttattac atctttaatt gcaaaacata ccttattaaa gaatggtact  1140
tatcaaaatt ctaagaaatc aagtatatac attgttaaac caaaaatgca tggatcaaaa  1200
gaagttgctt ttgccaacac attatttaac tctatagaag atatgttagg gttagagcgt  1260
catactataa aaattggagt tatggatgag gaaagaagaa caactttaaa tcttaaagcc  1320
tgtataaagg aagtaaagga cagagtagct tttataaata ctggttttct tgacagaact  1380
ggagatgaaa tacacacatc aatggaagcc ggagcagtta taagaaaaaa cgatatgaag  1440
gcttcaaaat ggcttcaagg atatgaacaa tcaaatgtaa atgtaggatt agctagtgga  1500
tttcaaggaa gggcacaaat aggtaaggga atgtgggcta tgccggatat gatggcagaa  1560
atgcttaaac aaaaagtagg tcatcttaaa gcaggagcca atacggcatg ggttcctagt  1620
cctacagcag caacccttca tgccctacat tatcatcaaa ttgatgttag agatgtacaa  1680
aacgagttac ttacacaatc cacagatctt caggatgata tattacaaat tccagttgct  1740
gaaaagccta attggtctaa agatgaaata cagcaagaat tagataataa tgcacaagga  1800
atacttggat atgtagttag atgggtagat cagggtgtag gttgttcaaa agttccagat  1860
ataaataatg taggacttat ggaagatcgg gctacactgc gcatctcaag tcagcatgta  1920
gcaaattggt tgcatcatgg tatttgtact aaagaacaag ttactgaaac attaaaaaga  1980
atggcgaaag ttgtagatca gcaaaatgaa aatgatccat tatatcagcc tatgagttca  2040
aattacagtg catcaatagc atttcaggct gcgtgcgatc ttgtattcca gggatacgac  2100
caacctaatg gatacacaga accaatattg catagaagaa ggattgaagc aaaggctaaa  2160
gcagcaataa aacaataa                                                2178

SEQ ID NO: 42           moltype = AA  length = 725
FEATURE                 Location/Qualifiers
source                  1..725
                        mol_type = protein
                        organism = Bacillus megaterium
SEQUENCE: 42
MTNYKQVGNL KVAPVLYQFI NEEALPGSGL STENFWSDFE ALVTELTPVN KRLLEKRDQL  60
QAQINAWHQE NPDGDFSEYK SFLTRIGYLE DKTEDFLIGT EGVDSEIAYQ AGPQLVVPVN  120
NARYAINAAN ARWGSLYDAL YGTDAISEEN GASRTSSYNP IRGEKVIAFA KNFLDEVVPL  180
VQSSHAEVVQ YSLENEKLVA QLNDGSLTEL QEEEKFVGYQ GEEESPDALL FKNNGLHFEV  240
QIDRTDSIGK TDDAGVKDIL MEAALTTIMD CEDSVAAVDA EDKVDVYRNW LGLMKGDLTS  300
TFKKGSQNMT RRLNPDRTYI SPDKKKILLS GRSLMFVRNV GHLMTNSAVL DRNGNEIYEG  360
ILDSVITSLI AKHTLLKNGT YQNSKKSSIY IVKPKMHGSK EVAFANTLFN SIEDMLGLER  420
HTIKIGVMDE ERRTTLNLKA CIKEVKDRVA FINTGFLDRT GDEIHTSMEA GAVIRKNDMK  480
ASKWLQGYEQ SNVNVGLASG FQGRAQIGKG MWAMPDMMAE MLKQKVGHLK AGANTAWVPS  540
PTAATLHALH YHQIDVRDVQ NELLTQSTDL QDDILQIPVA EKPNWSKDEI QQELDNNAQG  600
ILGYVVRWVD QGVGCSKVPD INNVGLMEDR ATLRISSQHV ANWLHHGICT KEQVTETLKR  660
MAKVVDQQNE NDPLYQPMSS NYSASIAFQA ACDLVFQGYD QPNGYTEPIL HRRRIEAKAK  720
AAIKQ                                                              725
```

| SEQ ID NO: 43 | moltype = DNA length = 1581 |
| --- | --- |
| FEATURE | Location/Qualifiers |
| misc_feature | 1..1581 |
| | note = Codon-adapted nucleotide sequence |
| source | 1..1581 |
| | mol_type = other DNA |
| | organism = synthetic construct |

SEQUENCE: 43

```
atgtcaagac cagcagcagg acttgcagta ttaggaccac cactttcgtc agcagcacaa    60
gaattattag gtaaacgcgc attagcattc gttcaattac tagaacagca atttggacat   120
agaagaagag aattacttca ggctagcaga cacagacaac agagatttga cggcggcgaa   180
aagcctgatt ttagatctga tactcttgca gttaggacgg gagaatggag tgtagctcca   240
gctccagcag aattacgcga caggagagtt gaaattactg gtcctgctgg agatagaaag   300
atggtttataa atgctttaaa ttccggagca agagtatca tgtgtgatct tgaagacgct   360
aattcaccaa cttgggctaa cactatgaat ggtcagttaa atataagaga tgctgaggca   420
ggaactatag cttatgaatc accagaagga aaggcttata gacttgctcc agatcatgca   480
gtaattaaaa taagaccaag aggatggcat cttgaagaat ctcatgtagc atgggaagga   540
caaagtgttt ctgcagcttt atttgacttt ggaatggctg cattcataa tgcaagagaa   600
aaagcaagaa gaggatctgg cttgtacttc tatttaccta gttagaatc tatggaagaa   660
gcagaactat gggaagacgt attcacattt gcagaaagag agcttggtct tgaaagaggt   720
atgtttaggc tacagttttt aatagaaacc ctaccagctg cctttgaaat ggaagaaata   780
cttttttgttc ttagagatca tgccgacgga ttgaattgta gaagatggga ttacatattt   840
agttatatta aaagttaag agcacaccca gaggctatat taccagatag aagtttggtt   900
actatggata gcccttttat ggcagcttat gctagacttg cagtacagac ttgtcataga   960
agaggcgcat tctgcatagg cggcatggct gcacagattc caatcaagaa tgattctgct  1020
gccaacgaac aagcactgga taaggtaaga cttgacaaat aagagaggt tagattaggg  1080
catgatggta cttgggttgc tcatcctgga cttgtagcag ttgctgaaaa agtatttaat  1140
gaacacatgc caggagataa tcaacttttc ttccatcctg atggttctgt tggtgctgaa  1200
caattgcttg aggctcctag aggaccaatt actgaggctg gagttagatt aaatttgtca  1260
gtttcacttc aatacattga ggcatggttg agaggtgcag tgccagttcc aataaacagc  1320
cttatggaag atgcagcaac tgctgaaatt tcaagagcac agttatggca gtggatacgg  1380
catccacaag gcatattaga agatggaaga aaaatgagtg cagatttata cagaaaatta  1440
ttagaagaag agcttggaaa attaccagca gcagcatcag gtgcttatgg acgggcagaa  1500
gaacttctta cagcaatgac tcttgccgat acttttgctg agttccttac gtagacgct  1560
tatagatatc ttcaagatta g                                            1581
```

| SEQ ID NO: 44 | moltype = AA length = 526 |
| --- | --- |
| FEATURE | Location/Qualifiers |
| source | 1..526 |
| | mol_type = protein |
| | organism = Paenibacillus sp. RU4X |

SEQUENCE: 44

```
MSRPAAGLAV LGPPLSSAAQ ELLGKRALAF VQLLEQQFGH RRRELLQARQ HRQQRFDGGE    60
KPDFRSDTLA VRTGEWSVAP APAELRDRRV EITGPAGDRK MVINALNSGA RVFMCDLEDA   120
NSPTWANTMN GQLNIRDAEA GTIAYESPEG KAYRLAPDHA VIKIRPRGWH LEESHVAWEG   180
QSVSAALFDF GMAAFHNARE KARRGSGLYF YLPKLESMEE AELWEDVFTF AERELGLERG   240
MFRATVLIET LPAAFEMEEI LFVLRDHADG LNCGRWDYIF SYIKKLRAHP EAILPDRSLV   300
TMDSPFMAAY ARLAVQTCHR RGAFCIGGMA AQIPIKNDSA ANEQALDKVR LDKLREVRLG   360
HDGTWVAHPG LVAVAEKVFN EHMPGDNQLF FHPDGSVGAE QLLEAPRGPI TEAGVRLNLS   420
VSLQYIEAWL RGTGAVPINS LMEDAATAEI SRAQLWQWIR HPQGILEDGR KMSADLYRKL   480
LEEELGKLPA AASGAYGRAE ELLTAMTLAD TFAEFLTVDA YRYLQD                 526
```

| SEQ ID NO: 45 | moltype = DNA length = 1599 |
| --- | --- |
| FEATURE | Location/Qualifiers |
| misc_feature | 1..1599 |
| | note = Codon-adapted nucleotide sequence |
| source | 1..1599 |
| | mol_type = other DNA |
| | organism = synthetic construct |

SEQUENCE: 45

```
atgaaacaag caacaacagg aaaacttaaa atagttggag aacaaaatga gcatacaaac    60
gaaatactta ccccagaggc tttagaattt gttttagcac ttcatgaaaa atttgatgca   120
agaagaaagg aattattaaa tgcaagacaa aagagacaga agagattaga tgctggtgaa   180
aagctagatt tccttccaga gacaaaacat attagagaag tgactggtc tatagctcct   240
cttccacaag atcttcagga tagacgtgtg gaaataactg gaccagtaga tagaaagatg   300
gtaataaatg cctaaaattc aggcgcaaag atgtttatgg catgttttga agatgcttca   360
agcccaactt gggaaaatat gataggcggc caaataaata tgagagatgc tataaataag   420
acaattgaat ttactcaggc ttcaaacggt aagcatacca agtccaatgc ggaaactgct   480
gtattattag ttaggcctag aggattacat cttttagaaa agcacgtttg agttcatgaa   540
gaacctatat caggctcatt ttttgacttt ggattatatt tatttcataa tgccaaaaat   600
gcactagcta aaggaacagg tccttatttt tatttaccaa aacttgaatc acatctcgaa   660
gcaagacttt ggaatgatgt atttgtattt gcccaggatt ataggcat accacaagga   720
actataaagg ctactgtact cattgaaact atccttgctg catttgaaat ggatgaaatc   780
ctatatgaat tgagagaaca ttcagctgga cttaactgtg gaagatggga ttatatattc   840
agctatataa aaagacttag aaatcaggca gatgtaatac ttcctgatag ggacaagtt   900
actatgacag tgccttttat gaaggcttat acatcacttt gtattcaaac ctgtcacaaa   960
aggaatgctc ctgctatggg cggcatggct gcacaaatac tataaaaaa cgatgatgaa  1020
gcgaatgctg tggcatttgc aaaggttgct gaggataaaa ggagagaggc tacagaagga  1080
catgatggta catgggttgc ccatccagga atggttcaa ctgcaatgga acaatttgat  1140
```

```
gctattatga ctactcctaa tcaaatacat aaaagagag aagatgtaca agttactgca    1200
gatgacctag ttgcagttcc agaaggtact ataactcttg aaggacttag agtaaattgt    1260
tcggttggag tacagtatat tgcaagttgg cttaggggaa atggggctgc ccctataaat    1320
aatcttatgg aagatgcagc aacagcagaa atttcaagaa ctcaagtatg gcaatgggtg    1380
agacacccaa aaggaatatt agatgatggc agaggaataa ctttagcttt tgttcttgaa    1440
atattggaag aagaattagt taaaattaaa gaggctgttg gtgaacaggc ttataattct    1500
ggaagatttg aagaggctgc tgaattattc aaatccctca tagaacaaga tgaatttgca    1560
gagttcctta cactaccagg atacgaaaaa ttggcataa                            1599

SEQ ID NO: 46              moltype = AA   length = 532
FEATURE                    Location/Qualifiers
source                     1..532
                           mol_type = protein
                           organism = Lysinibacillus sp. A1
SEQUENCE: 46
MKQATTGKLK IVGEQNEHTN EILTPEALEF VLALHEKFDA RRKELLNARQ KRQKRLDAGE    60
KLDFLPETKH IREGDWSIAP LPQDLQDRRV EITGPVDRKM VINALNSGAK MFMACFEDAS    120
SPTWENMIGG QINMRDAINK TIEFTQASNG KTYKLNAETA VLLVRPRGLH LLEKHVLVHD    180
EPISGSFFDF GLYLFHNAKN ALAKGTGPYF YLPKLESHLE ARLWNDVFVF AQDYIGIPQG    240
TIKATVLIET ILAAFEMDEI LYELREHSAG LNCGRWDYIF SYIKRLRNQA DVILPDRGQV    300
TMTVPFMKAY TSLCIQTCHK RNAPAMGGMA AQIPIKNDDE ANAVAFAKVA EDKRREATEG    360
HDGTWVAHPG MVATAMEQFD AIMTTPNQIH KKREDVQVTA DDLVAVPEGT ITLEGLRVNC    420
SVGVQYIASW LRGNGAAPIN NLMEDAATAE ISRTQVWQWV RHPKGILDDG RGITLAFVLE    480
ILEEELVKIK EAVGEQAYNS GRFEEAAELF KSLIEQDEFA EFLTLPGYEK LA            532

SEQ ID NO: 47              moltype = DNA   length = 1590
FEATURE                    Location/Qualifiers
misc_feature               1..1590
                           note = Codon-adapted nucleotide sequence
source                     1..1590
                           mol_type = other DNA
                           organism = synthetic construct
SEQUENCE: 47
atgtcaacaa gaacatcaag agttacatta cctggagaaa tgttaccagc ttataacgaa    60
atacttaccc cagaagtttt atcattcctt aaagaattac atgaaaattt taatgaaaga    120
cgaacggaat tacttcaaaa aagggttgaa aaacaaaaaa ggattgatgc gggtgaattt    180
ccaaaatttt tagaagaaac aaagcacatc agagaggctg attggacaat cgccaatctt    240
cctaagacc ttgaagacag aagagtagaa ataacaggtc ctgtagatcg taaaatggtt    300
attaatgcat tgaattcagg agcacacttg tttatggctg attttgaaga ttccaattca    360
ccaacttggg aaaatactat agaaggacaa ataaattgaa gagatgcagt aaaagggaca    420
ataagtcata aaaatgataa gggaaaagaa tataggttaa atgacaaaac agcagttttt    480
atagttaggc ctagaggatg gcacttagaa gaaaagcaca tgcaggttga tggaaagaat    540
atgtcggat ctcttgtaga ttttggatta tatttttttc ataatgcaaa ggctctatta    600
gaaaaaggtt caggaccata cttctattta cctaaaatgg aatcttatct tgaagcaaga    660
ctttgaacg atgtatttgt atttgctcaa agtatatag ataccaaa tggaactatc    720
aaggcaactg tattattgga aactatccat gcatcatttg aaatggatga aattcttttat    780
gaattaaaag atcattcagc aggattaaat tgtggacgct gggattatat tttttctttc    840
ctaaaaggat ttagaaacca caatgaattt cttttaccag atagggctca agtaactatg    900
actgctcctt ttatgagggc ttattctctc aaggtaatcc aaacttgtca tagaagaaat    960
gcaccagcta taggcggcat ggctgcacaa attcctataa aaaataatcc agaggctaat    1020
gaagcagcat ttgaaaaagt aagagcagat aaagaaagag aagcattaga tggtcatgac    1080
ggtacttggg tagcacatcc tggcttagtt cccgttgcta tggaagtatt taatcatatc    1140
atgaaaactc ctaatcagat atttcgcaaa agagaagaga taagagttac ggaaaaggat    1200
ttacttgaag ttcctgtagg tacaatcact gaagaagggt taagaactaa catatctgtt    1260
ggaatacagt acatagcatc atggttatca ggaagagggc ctgccctat atataatctc    1320
atggaagatg cagctactgc agaaatttcc agggctcaaa tttggcaatg gataagacat    1380
gaaggcggca aactaaacga tggtagaaat attacattgg aattaatgga agaatggaaa    1440
gaagaagaat tggtaaagat agaacgggaa ataggaaaag aggcattcaa aaaaggcaga    1500
tttcaagagg ctactacatt atttacaaat ttgataagaa atgatgaatt tgtcccattc    1560
cttacttttac ctggatacga gatattataa                                     1590

SEQ ID NO: 48              moltype = AA   length = 529
FEATURE                    Location/Qualifiers
source                     1..529
                           mol_type = protein
                           organism = Bacillus cereus
SEQUENCE: 48
MSTRTSRVTL PGEMLPAYNE ILTPEVLSFL KELHENFNER RTELLQKRVE KQKRIDAGEF    60
PKFLEETKHI READWTIANL PKDLEDRRVE ITGPVDRKMV INALNSGAHL FMADFEDSNS    120
PTWENTIEGQ INLRDAVKGT ISHKNDKGKE YRLNDKTAVL IVRPRGWHLE EKHMQVDGKN    180
MSGSLVDFGL YFFHNAKALL EKGSGPYFYL PKMESYLEAR LWNDVFVFAQ KYIGIPNGTI    240
KATVLLETIH ASFEMDEILY ELKDHSAGLN CGRWDYIFSF LKGFRNHNEF LLPDRAQVTM    300
TAPFMRAYSL KVIQTCHRRN APAIGGMAAQ IPIKNNPEAN EAAFEKVRAD KEREALDGHD    360
GTWVAHPGLV PVAMEVFNHI MKTPNQIFRK REEIRVTEKD LLEVPVGTIT EEGLRTNISV    420
GIQYIASWLS GRGAAPIYNL MEDAATAEIS RAQIWQWIRH EGGKLNDGRN ITELMEEWK    480
EEELVKIERE IGKEAFKKGR FQEATTLLFTN LIRNDEFVPF LTLPGYEIL               529
```

| SEQ ID NO: 49 | moltype = DNA length = 1425 |
|---|---|
| FEATURE | Location/Qualifiers |
| misc_feature | 1..1425 |
| | note = Codon-adapted nucleotide sequence |
| source | 1..1425 |
| | mol_type = other DNA |
| | organism = synthetic construct |

SEQUENCE: 49

```
atgcagcaca aattattaat taacggagaa cttgtaagtg gagaaggaga aaaacaacca    60
gtatataacc cagcaactgg agatgtatta ttagaaatag cagaggcatc agcagaacag   120
gtagatgctg cagttagggc agcagacgca gcatttgcag agtggggaca aactactcct   180
aaagtgcgtg cagaatgtct tctaaaactt gcagacgtta tagaggaaaa tggacaagta   240
tttgctgaat tggagtcgag aaactgcggt aaacctttac attcagcatt taatgatgaa   300
ataccagcaa tagtagatgt attcagattt tttgctggtg cagctaggtg tcttaacgga   360
ctagcagctg gagagtatct tgaaggacat acatcaatga taagaagaga tccattaggt   420
gtagttgcca gtatagctcc ttggaactat ccttttgatg tggcagcatg gaaacttgcc   480
cccgcccttg cagcaggaaa ttgtgttgta ttgaaaccaa gtgaaataac ccctcttaca   540
gcattaaaat tagctgaatt agcaaaggac atcttcccag ctggtgttat aaatatacta   600
tttggaagag gcaaaacagt tggtgatcct ttgacaggac atcctaaggt aaggatggtt   660
agccttacag gctcaatagc aacaggcgaa catattatat cacacacggc atcttctata   720
aaacgcacgc acatggaatt gggcggcaaa gccccgttta ttgtatttga tgatgcagat   780
atagaggcag tagtagaagg agttagaact tttggatatt ataatgctgg ccaagattgt   840
actgctgctt gtaggattta tgctcaaaaa ggtatttatg atacacttgt tgaaaagcta   900
ggtgctgcag ttgcaaccct taagtctggt gcaccagatg atgaatctac agaattggga   960
cctttatctt ctttagcaca ccttgaaaga gttagcaaag cagttgaaga ggctaaggct  1020
actgcagcaa taaaggtaat aacaggcggc gaaaagagaa agggaaatgg atattattat  1080
gctcctacgc ttttagctgg tgcccttcag gatgatgcta tagtacagaa agaagtatat  1140
ggaccagtag taagtgtaac tccttttgat aatgaagaac aggtagttaa ctgggccaat  1200
gatagccagt acgattagc gtcttctgta tggacaaagg atgtaggcag agcacatagg  1260
gtatcagcaa gacttcaata tggatgtact tgggtaataa ctcacttat gttagtaagt  1320
gagatgccac atggcggcca aaagttgtca ggatatggaa aagatgag cttatacggt  1380
ttggaagact atacagtagt aagacacgta atggtaaaac attag              1425
```

| SEQ ID NO: 50 | moltype = AA length = 474 |
|---|---|
| FEATURE | Location/Qualifiers |
| source | 1..474 |
| | mol_type = protein |
| | organism = Escherichia coli |

SEQUENCE: 50

```
MQHKLLINGE LVSGEGEKQP VYNPATGDVL LEIAEASAEQ VDAAVRAADA AFAEWGQTTP    60
KVRAECLLKL ADVIEENGQV FAELESRNCG KPLHSAFNDE IPAIVDVFRF FAGAARCLNG   120
LAAGEYLEGH TSMIRRDPLG VVASIAPWNY PLMMAAWKLA PALAAGNCVV LKPSEITPLT   180
ALKLAELAKD IFPAGVINIL FGRGKTVGDP LTGHPKVRMV SLTGSIATGE HIISHTASSI   240
KRTHMELGGK APVIVFDDAD IEAVVEGVRT FGYYNAGQDC TAACRIYAQK GIYDTLVEKL   300
GAAVATLKSG APDDESTELG PLSSLAHLER VSKAVEEAKA TAAIKVITGG EKRKGNGYYY   360
APTLLAGALQ DDAIVQKEVY GPVVSVTPFD NEEQVVNWAN DSQYGLASSV WTKDVGRAHR   420
VSARLQYGCT WVNTHFMLVS EMPHGGQKLS GYGKDMSLYG LEDYTVVRHV MVKH         474
```

| SEQ ID NO: 51 | moltype = DNA length = 1440 |
|---|---|
| FEATURE | Location/Qualifiers |
| misc_feature | 1..1440 |
| | note = Codon-adapted nucleotide sequence |
| source | 1..1440 |
| | mol_type = other DNA |
| | organism = synthetic construct |

SEQUENCE: 51

```
atgtcagttc cggttcagca cccaatgtat attgatggac aatttgtaac ttggcgagga    60
gatgcatgga tagatgttgt gaatccagcg actgaggcag ttatctctag gattcctgat   120
ggtcaggcag aggatgccag aaaagcaata gatgctgcag aaagggctca accagaatgg   180
gaagcgttac ctgctattga aagggcttcc tggttacgaa aatttcagc aggaataaga   240
gaaagagcat cagaaatatc agcactaata gttgaagaag gcggcaaaat tcaacaactt   300
gcagaggttg aagtagcatt tacagcggat tatattgatt acatggctga atgggcagga   360
agatacgaaa gagagattat tcaatctgat agaccaggag aaaatatctt attattcaaa   420
agagcattag gtgttacaac aggcattctt ccttggaatt ttccattctt cctaattgca   480
agaaagatgg ccccagcact acttacagga aatactattg taataaaacc ttcagaattt   540
actcctaata atgctatagc tttttgctaaa attgtagatg aaataggact tccaagaggt   600
gtatttaatc tagtactagg acgtggtgga actgtaggac aagaattagc tggaaatccg   660
aaggtagcaa tggttttctat gactggatca gtttccgctg gtgaaaaaat aatggcgact   720
gcagctaaaa acattacaaa agtatgcttg gagcttggcg gcaaagcacc agcaattgta   780
atggatgatg cagatttaga acttgcagta aaggctattg tagattcaag tgtaataaac   840
agtggtcagg tatgcaattg tgctgaacgt atttatgtac aaaaaggtat atatgatcaa   900
tttgtaaatc gattgggtga agcaatgcaa gcagtacaat ttggaaaccc agctgaacgg   960
aacatatatg cgatgggacc tttaataaat gcagcagcac ttgtaaagat tgaacaaaaa  1020
gtagctaggg ctgtggaaga aggagcaaga gttgcattgg gcgcaagc agttgaaggt  1080
aaaggatatt attatcctcc tacactttta ctagatgttc ttcaagaaat gagtataatg  1140
catgaagaaa cttttggacc tgtattacca gttgtagctt tgatactttt agaagaggct  1200
atatcaatgc aaatgattc tgactatggc ttaactagca gcatatacac tcaaaatcta  1260
aacgtagcta tgaaggctat taagggtta aaatttggtg agacttatat aaatagagaa  1320
```

```
aactttgagg ctatgcaagg ttttcatgct ggatggagaa aaagtggtat tgcggcgct  1380
gacggaaagc atggacttca tgaatattta cagactcagg ttgtttatct tcaatcttaa 1440

SEQ ID NO: 52          moltype = AA   length = 479
FEATURE                Location/Qualifiers
source                 1..479
                       mol_type = protein
                       organism = Escherichia coli
SEQUENCE: 52
MSVPVQHPMY IDGQFVTWRG DAWIDVVNPA TEAVISRIPD GQAEDARKAI DAAERAQPEW  60
EALPAIERAS WLRKISAGIR ERASEISALI VEEGGKIQQL AEVEVAFTAD YIDYMAEWAR  120
RYEGEIIQSD RPGENILLFK RALGVTTGIL PWNFPFFLIA RKMAPALLTG NTIVIKPSEF  180
TPNNAIAFAK IVDEIGLPRG VFNLVLGRGE TVGQELAGNP KVAMVSMTGS VSAGEKIMAT  240
AAKNITKVCL ELGGKAPAIV MDDADLELAV KAIVDSRVIN SGQVCNCAER IYVQKGIYDQ  300
FVNRLGEAMQ AVQFGNPAER NDIAMGPLIN AAALERVEQK VARAVEEGAR VALGGKAVEG  360
KGYYYPPTLL LDVLQEMSIM HEETFGPVLP VVAFDTLEEA ISMANDSDYG LTSSIYTQNL  420
NVAMKAIKGL KFGETYINRE NFEAMQGFHA GWRKSGIGGA DGKHGLHEYL QTQVVYLQS   479

SEQ ID NO: 53          moltype = DNA   length = 1449
FEATURE                Location/Qualifiers
misc_feature           1..1449
                       note = Codon-adapted nucleotide sequence
source                 1..1449
                       mol_type = other DNA
                       organism = synthetic construct
SEQUENCE: 53
atgaaattaa atgattcaaa acttttaga caacaagcct taataaatgg agaatggtta  60
gatgcaaata acggagaagt aatagatgtt actaatccag caaatggtga taaacttggt  120
tctgttccaa agatgggagc agatgaaacc agggctgcta tagatgcagc aaatagagca  180
cttccagcat ggagagcact tacagcaaaa gaacggcaaa atatacttag aaattggttt  240
aatcttttaa tggaacatca ggatgatcta gcaaggctta tgacgcttga acaggggaaa  300
cctcttgctg aggctaaagg agagatcagt tatgcagcgt catttatcga atggtttgct  360
gaagaaggaa aaaggattta tggagatact ataccaggac atcaggcaga caaaagactt  420
atagttatta acaacctata aggtgtaact gctgctataa ctccttggaa atcccagca  480
gctatgataa ctagaaaagc aggaccagct cttgctgctg gttgcactat ggttttaaaa  540
cctgcttccc agactccttt tagtgccctt gcacttgctg aattagctat tcgtgctggt  600
attccagcgg gtgtattcaa tgtagttact ggatctgctg gtgcggttgg aaatgagctt  660
acatcaaatc cgcttgtaag aaaactttca tttacggaa gtacagaaat aggtaggcaa  720
ttaatggaac aatgtgctaa agatattaag aaagtttcac tggagttagg cggcaatgcc  780
ccttttattg tatttgatga tgcagactta gataaagcag ttgaaggtgc tttaagttct  840
aaatttagga tgctggaca aacttgtgta tgtgcgaata gattatacgt ccaagacgga  900
gtttacgata gatttgcaga aaaacttcaa caggctgtat ctaaattaca cattggagat  960
gggttagaa aaggcgttac aattggccca ttgatagatg aaaaagcagt agctaaagtt  1020
gaggaacaca ttgctgatgc acttgaaaaa ggtgctagag ttgtttgcgg cggcaaggct  1080
gatgaaagag cggcaacttt tttccagcct actatacttg tagacgttcc agctaatgca  1140
aaggtatcaa aagaggaaac ctttggtcca cttgctcctt tatttagatt taaggatgag  1200
gcagatgtta tagcacaggc aaatgatacc gaatttgaac ttgcagctta tttctatgct  1260
agggatttat ccagggtttt tagagttggt gaggctttag agtacggcat tgttggaata  1320
aatactggaa taatatcaaa tgaagttgca ccatttggcg gcataaaggc tagtggatta  1380
gggagagaag ctcaaaaata tggaatagaa gactattggg aaataaaata tatgtgcatt  1440
ggcttataa                                                         1449

SEQ ID NO: 54          moltype = AA   length = 482
FEATURE                Location/Qualifiers
source                 1..482
                       mol_type = protein
                       organism = Escherichia coli
SEQUENCE: 54
MKLNDSKLFR QQALINGEWL DANNGEVIDV TNPANGDKLG SVPKMGADET RAAIDAANRA  60
LPAWRALTAK ERANILRNWF NLLMEHQDDL ARLMTLEQGK PLAEAKGEIS YAASFIEWFA  120
EEGKRIYGDT IPGHQADKRL IVIKQPIGVT AAITPWNFPA AMITRKAGPA LAAGCTMVLK  180
PASQTPFSAL ALAELAIRAG IPAGVFNVVT GSAGAVGNEL TSNPLVRKLS FTGSTEIGRQ  240
LMEQCAKDIK KVSLELGGNA PFIVFDDADL DKAVEGALSS KFRNAGQTCV CANRLYVQDG  300
VYDRFAEKLQ QAVSKLHIGD GLEKGVTIGP LIDEKAVAKV EEHIADALEK GARVVCGGKA  360
DERGGNFFQP TILVDVPANA KVSKEETFGP LAPLFRFKDE ADVIAQANDT EFGLAAYFYA  420
RDLSRVFRVG EALEYGIVGI NTGIISNEVA PFGGIKASGL GREGSKYGIE DYLEIKYMCI  480
GL                                                                482

SEQ ID NO: 55          moltype = DNA   length = 1443
FEATURE                Location/Qualifiers
misc_feature           1..1443
                       note = Codon-adapted nucleotide sequence
source                 1..1443
                       mol_type = other DNA
                       organism = synthetic construct
SEQUENCE: 55
atgactgaaa aaataatttt attcataaat ggatcttggg ttgctcctaa aggcggcgaa  60
tggattaaag ttgaaaaccc agctacaaag gcagtagtgg cagaagtagc aaagggcggc  120
caggctgacg tagatgctgc tgtatcagca gctaagtcag catttattgg atggtcaaga  180
```

```
aggatggcaa ctgagagagc agattatata catgcattaa aagatcttgt gaaaagggat    240
aaagaaaaat tagcagctat tataactagt gaaatgggga aaccattgaa agaggctaga    300
atagaagtag attttgcaat tggattactt agatttgcag cagaaaatgt tttaagactt    360
cagggagaaa taataccagg atcttctcca gaagaaaaga tattaattga tagggtacct    420
ttgggagtaa taggtgctat aacagcatgg aattttcctc ttgcactttg tgcaagaaag    480
attggacctg ctgtggcagc gggaaatact atagttgtaa aaccacatga attaacgcca    540
ttagcttgtc tacatcttgc taaattagtt gaagaggcaa agatcccaca tggagtttata   600
aatgttgtaa caggtgatgg caaagatgta ggagtacctc tagtagcaca taagatatt    660
aaattaataa ctatgacagg ttccacgcct gctggaaaaa aaattatggc agcagctagt    720
gagacactta aagaagttag gttagaactt ggcggcaaag caccatttat ggttatggaa    780
gatgctgata ttgacagggc agcagatgct gccgttacag caagatttaa taatgcggga    840
caggtatgta cttgtaatga agaacctac attcatgaag cagtttacga caaatttgtt    900
caaaaagtta gagaaaaaat agaagcatta aaagtaggac tgccaacaga tccatctaca    960
gatatgggac ctaaagtatc tgaggacgaa cttaataaag ttcatgagat ggttgaacat   1020
gctgtaagac aaggagcaag attagctata ggcggcaaaa ggttaactgg ggcgtttat   1080
gataagggat acttctatgc accaacactg ttgacagatg taactcaaga tatggacata   1140
gttcacaatg aggtatttgg tcctgtaatg tcattgatta gagttaaaga tttgatcag    1200
gctataacat gggcaaatga ttgtagatac gggctaagtg cttatctttt cactaatgat   1260
cttcaagga tacttaggat gacaagagat cttgaatttg gagaagtata cgtgaaccgt    1320
ccgggcggcg aagcgccaca aggatttcat catggataca aagaatctgg acttggcggc    1380
gaggacggac agcacggaat ggaagcatac gtacagacaa aaacaatata tctaaatgca    1440
taa                                                                 1443

SEQ ID NO: 56          moltype = AA  length = 480
FEATURE                Location/Qualifiers
source                 1..480
                       mol_type = protein
                       organism = Gluconobacter oxydans
SEQUENCE: 56
MTEKNNLFIN GSWVAPKGGE WIKVENPATK AVVAEVAKGG QADVDAAVSA AKSAFIGWSR     60
RMATERADYI HALKDLVKRD KEKLAAIITS EMGKPLKEAR IEVDFAIGLL RFAAENVLRL    120
QGEIIPGSSP EEKILIDRVP LGVIGAITAW NFPLALCARK IGPAVAAGNT IVVKPHELTP    180
LACLHLAKLV EEAKIPHGVI NVVTGDGKDV GVPLVAHKDI KLITMTGSTP AGKKIMAAAS    240
ETLKEVRLEL GGKAPFMVME DADIDRAADA AVTARFNNAG QVCTCNERTY IHEAVYDKFV    300
QKVREKIEAL KVGLPTDPST DMGPKVSEDE LNKVHEMVEH AVRQGARLAI GGKRLTGGVY    360
DKGYFYAPTL LTDVTQDMDI VHNEVFGPVM SLIRVKDFDQ AIAWANDCRY GLSAYLFTND    420
LSRILRMTRD LEFGEVYVNR PGGEAPQGFH HGYKESGLGG EDGQHGMEAY VQTKTIYLNA    480

SEQ ID NO: 57          moltype = DNA  length = 1434
FEATURE                Location/Qualifiers
misc_feature           1..1434
                       note = Codon-adapted nucleotide sequence
source                 1..1434
                       mol_type = other DNA
                       organism = synthetic construct
SEQUENCE: 57
atgtcttcag tgcctgtatt ccagaacttt ataaatggac aatttacgca tagtgaagcc     60
catcttgatg tttataatcc cgccacagga gcacttttat caagggtacc agcaagtact    120
tgtgcagatg tagatcaggc tcttgctggt gcaagagcag ctcaaaaagc atggtcagca    180
aaaccagcaa tagaaagggc aggataccttt agacgtattg cttcaaaact tagagaaaat    240
gttgctcatc ttgcaagaac tataactcta gaacaaggaa aaatatcagc attagcagaa    300
gttgaagtaa acttcacagc tgactacctt gattatatgg cagaatgggc tagaagaata    360
gaaggcgaaa taataacttc agatcgcccc ggggaaaaca tattccttttt cgtaaaccct    420
ttaggagtag tggcaggaat acttccttgg aattttccctt tcttcttaat cgcaagaaaa    480
atggccaccag cattgcttac aggcaataca atttgttataa aaccaagtga agagcaccag    540
aataattgtt ttgaatttgc tagacttgta gctgagactg atttacctcc aggagttttt    600
aatgttgtat gtggagatgg aagagtagga gcagcattaa gtgggcataa aggagtagat    660
atgataagct ttacaggctc agttgacaca ggatcacgaa taatgactgc agcagcgact    720
aatattacaa aattaaaattt ggaacttggc ggcaaggcac cagtcgatt ttggcagat    780
gcagatcttg cattggcagt aaaagcaata agagattcaa gaataataaa tactggacaa    840
gtatgtaatt gtgctgaaag agtatatgtt gagagaaaag tagctgatca atttatagaa    900
agaataagtc ctgcaatgtc agctacaaga tacgagatc cattagctga accggatgta    960
gagatgggac cattaataaa caggcaagga cttgattctg tagaaagaaa agtacgtatt   1020
gctcttcaac agggtgcttc tcttattagt ggcggccgga tagcgcgtag acctgatgga   1080
ttccattttg agccaactgt attagcagga tgtaatgctt caatggatat tatgagagaa   1140
gaaatatttg ggccagttt accaatccaa atagtagatg atttagtga agcaatcgct   1200
ttagctaacg actgcgatta tggattaact tcatctgtat atacaaggga ccttggacgt   1260
gctatgcatg ctataagagg attagttttt ggtgaaactt atgttaatag ggaaaatttt   1320
gaggctatgc agggattcca tgctggtgta agaaagtcag gagtaggcgg cgcagatggc   1380
aagcatggat tatatgaata tactctcact catgcagtat atctccagtc ttaa          1434

SEQ ID NO: 58          moltype = AA  length = 477
FEATURE                Location/Qualifiers
source                 1..477
                       mol_type = protein
                       organism = Pseudomonas fluorescens
SEQUENCE: 58
MSSVPVFQNF INGQFTHSEA HLDVYNPATG ALLSRVPAST CADVDQALAG ARAAQKAWSA     60
KPAIERAGYL RRIASKLREN VAHLARTITL EQGKISALAE VEVNFTADYL DYMAEWARRI    120
```

```
EGEIITSDRP GENIFLFRKP LGVVAGILPW NFPFFLIARK MAPALLTGNT IVIKPSEETP  180
NNCFEFARLV AETDLPPGVF NVVCGDGRVG AALSGHKGVD MISFTGSVDT GSRIMTAAAT  240
NITKLNLELG GKAPAIVLAD ADLALAVKAI RDSRIINTGQ VCNCAERVYV ERKVADQFIE  300
RISAAMSATR YGDPLAEPDV EMGPLINRQG LDSVERKVRI ALQQGASLIS GGRVADRPDG  360
FHFEPTVLAG CNASMDIMRE EIFGPVLPIQ IVDDLDEAIA LANDCDYGLT SSVYTRDLGR  420
AMHAIRGLDF GETYVNRENF EAMQGFHAGV RKSGVGGADG KHGLYEYTHT HAVYLQS    477

SEQ ID NO: 59           moltype = DNA   length = 1434
FEATURE                 Location/Qualifiers
misc_feature            1..1434
                        note = Codon-adapted nucleotide sequence
source                  1..1434
                        mol_type = other DNA
                        organism = synthetic construct
SEQUENCE: 59
atgtctcatg ctatatatca gaactatata gctaatgcat ttgtagcatc agatgaacac   60
ttagaggtac acaatccagc gaatggacaa ttgcttgctc atgtacctca gggttcttct  120
gctgaagttg aaagggctat agctgctgca agacaagccc aaaaagcatg ggctgctaga  180
ccagcaatag aaagggctgg atatttaaga aaatagcat caaaaataag agaacacgga   240
gaaagattag cccgtataat aacagcagaa cagggaaaag ttttagaact ggcaagagtt  300
gaagtaaatt ttacagctga ttatttagac tacatggctg agtgggcaag aagattggaa  360
ggagagttct tgagttcaga tagaccagga gaatctatat tttgttaag aaaacctctt   420
ggagttgtcg ctggaatact tccttggaat tttccttct tccttatagc tagaaaaatg    480
gctccagcac tgcttacagg aaatactata gttataaagc cttctgaaga gactcctata   540
aattgttttg aatttgcaag actggtagca gagacagatc ttccagcggg agtatttaat   600
gttgtatgtg gaactggagc gactgtagga aatgcttaa ctagtcatcc tggaatagat     660
ttgataagct ttacaggctc agttggaaca ggaagtagaa taatggcagc agcagcacca   720
aatataacaa aattgaatct gaacttggg gcaaggcac cagccattgt actagctgat      780
gctgatcttg atcttgcagt tagagcaata actgcatcaa gggtaatcaa tacaggtcag   840
gtatgtaact gtgctgaaag agtatacgtg gagagaaagt tgcagatgc atttattgaa     900
aggattgctg cagcaatggc aggaactaga tatggtgatc cattagcaga aaatgggttg   960
gatatgggtc cacttataaa tagggctgcg ttggacaaag ttgcacaaat ggtaagaact   1020
gcaagtggtc agggtgccca ggttataaca ggcggcgcag ttgccgactt aggacaagga   1080
ttccactacc aacctacagt attagctggc tgctctgcag atatggaaat tatgagaaag  1140
gaaatatttg gtcctgtact tcctatacaa atagtagatg acttagatga ggctattgca   1200
ttatcaaatg attccgaata tggattaaca agctccatat ataccgccag cttaagtgca   1260
gctatgcagg ctacaagaag ccttgattt ggagaaacct acataaatcg tgaaaacttt     1320
gaagcaatgc aaggttttca tgctggtaca agaaagtctg gcataggcgg cgctgacgga   1380
aagcacgggt tatatgaata tacgcatacc catgtagttt atatccaagc ataa         1434

SEQ ID NO: 60           moltype = AA   length = 477
FEATURE                 Location/Qualifiers
source                  1..477
                        mol_type = protein
                        organism = Pseudomonas fluorescens
SEQUENCE: 60
MSHAIYQNYI ANAFVASDEH LEVHNPANGQ LLAHVPQGSS AEVERAIAAA RQAQKAWAAR   60
PAIERAGYLR KIASKIREHG ERLARIITAE QGKVLELARV EVNFTADYLD YMAEWARRLE  120
GEVLSSDRPG ESIFLLRKPL GVVAGILPWN FPFFLIARKM APALLTGNTI VIKPSEETPI  180
NCFEFARLVA ETDLPAGVFN VVCGTGATVG NALTSHPGID LISFTGSVGT GSRIMAAAAP  240
NITKLNLELG GKAPAIVLAD ADLDLAVRAI TASRVINTGQ VCNCAERVYV ERKVADFIER  300
RIAAAMAGTR YGDPLAENGL DMGPLINRAA LDKVAQMVRT ASGQGAQVIT GGAVADLGQG  360
FHYQPTVLAG CSADMEIMRK EIFGPVLPIQ IVDDLDEAIA LSNDSEYGLT SSIYTASLSA  420
AMQATRSLDF GETYINRENF EAMQGFHAGT RKSGIGGADG KHGLYEYTHT HVVYIQA    477

SEQ ID NO: 61           moltype = DNA   length = 1155
FEATURE                 Location/Qualifiers
misc_feature            1..1155
                        note = Codon-adapted nucleotide sequence
source                  1..1155
                        mol_type = other DNA
                        organism = synthetic construct
SEQUENCE: 61
atggccaaca gaatgatctt aaatgaaaca gttatattg gagcaggagc aatagaaaat      60
atagtggcag aggctaaggt tagaggttat aaaaaggctc ttgcagttac tgatagggac  120
cttattaaat taatgtagc aaccaaagtt acagatcttt taaagcaaa caatcttgct     180
tttgaaatat ttgatgaagt aaaagcaaat cccactatta tgttgtttt agctggtatt    240
gaaaaattta aggcagcagg agcagattac ttattagcta taggcggcgg ctcgagtatc   300
gatacggcaa aagcaatagg tattatagta aagaaccctg aatttagtga tgttagatcc    360
cttgaaggag ttgccgatac aaaaaataaa tgtgttgata ttatagctgt acctactact   420
gctggcacag cagctgaggt aactataaac tatgtaataa cagatgaaga aaaaaagaga   480
aaatttgtct gtgttgatcc tcatgatata cctgtaatag ccgtagtaga ttcagaaatg   540
atgtcaagta tgccaaaagg actaacagca gcaacaggaa tggatgcact acgcatgct    600
ataggagat atataacaaa aggagcctgg gaacttacag catgcactca tcttaaggct    660
atagaaataa ttggaagatc ccttagatca gcagttaata tgaaccaaa aggaagagaa   720
gatatggctt aggacaata cgtggcagga atgggattta gcaatgttgg tttgggaata   780
gtccatggta tggctcatcc tcttgggca ttctatgata ctcctcatgg tatagcaaat     840
gcagtactcc ttccttatgt tatggagtat aatgcagagg caacaggata caatatcaga    900
gaaattgccc gtgcaatggg tgttcaaggt gtagactcaa tgagccagga tgaatacaga   960
```

```
aaagcggcta ttgatgctgt aaagaaatta agtgaagatg ttggtattcc taaggtatta   1020
aatgagattg gagtaaagga agaagattta caggctcttt ctgaatcagc atttgcagat   1080
gcttgtactc caggaaatcc tagagatact tctgttgaag aaatacttgc catatataag   1140
aaggcattca aataa                                                    1155

SEQ ID NO: 62            moltype = AA   length = 384
FEATURE                  Location/Qualifiers
source                   1..384
                         mol_type = protein
                         organism = Clostridium saccharoperbutylacetonicum
SEQUENCE: 62
MANRMILNET SYIGAGAIEN IVAEAKVRGY KKALAVTDRD LIKFNVATKV TDLLKANNLA    60
FEIFDEVKAN PTINVVLAGI EKFKAAGADY LLAIGGGSSI DTAKAIGIIV KNPEFSDVRS   120
LEGVADTKNK CVDIIAVPTT AGTAAEVTIN YVITDEEKKR KFVCVDPHDI PVIAVVDSEM   180
MSSMPKGLTA ATGMDALTHA IEGYITKGAW ELTDALHLKA IEIIGRSLRS AVNNEPKGRE   240
DMALGQYVAG MGFSNVGLGI VHGMAHPLGA FYDTPHGIAN AVLLPYVMEY NAEATGYKYR   300
EIARAMGVQG VDSMSQDEYR KAAIDAVKKL SEDVGIPKVL NEIGVKEEDL QALSESAFAD   360
ACTPGNPRDT SVEEILAIYK KAFK                                          384

SEQ ID NO: 63            moltype = DNA   length = 504
FEATURE                  Location/Qualifiers
misc_feature             1..504
                         note = Codon-adapted nucleotide sequence
source                   1..504
                         mol_type = other DNA
                         organism = synthetic construct
SEQUENCE: 63
atggtatcaa gtggagtttt ttctcttcat ctcaaactta taaacagaat attatcagct    60
ttagccgtat gtaaacaaat ttcccagata ttttgatttag ctatagtggc tttagctgta   120
tgtgatggcg gcataatggc tggatctcat agaataaatg gaatggaaca tcctgtaagt   180
gatttatatg atgcagttca tggtaaggga ttggctgctt taactcctat aatagttgaa   240
aaatcctgga aaagtgatat agaaaaatat gatgatatca gcaaattgat tggatgttca   300
tcagcaaaaa attgtgcaga tgctatacgg tcattccttg aaaagataaa tctaaacgta   360
acccttggtg aattaggtgt taagaaaaaa gatgtagaat ggatgtcaga aaattgcatg   420
aaagtgtcaa aaccttccat aattaatcac ccaagggaat ttactctaga gaaaattaag   480
aacatttatt atgaagaatt ataa                                          504

SEQ ID NO: 64            moltype = AA   length = 167
FEATURE                  Location/Qualifiers
source                   1..167
                         mol_type = protein
                         organism = Clostridium ljungdahlii
SEQUENCE: 64
MVSSGVFSLH LKLINRILSA LAVCKQISQI FDLAIVALAV CDGGIMAGSH RINGMEHPVS    60
DLYDAVHGKG LAALTPIIVE KSWKSDIEKY DDISKLIGCS SAKNCADAIR SFLEKINLNV   120
TLGELGVKEK DVEWMSENCM KVSKPSIINH PREFTLEEIK NIYYEEL                167

SEQ ID NO: 65            moltype = DNA   length = 1149
FEATURE                  Location/Qualifiers
misc_feature             1..1149
                         note = Codon-adapted nucleotide sequence
source                   1..1149
                         mol_type = other DNA
                         organism = synthetic construct
SEQUENCE: 65
atggcaaata gaatgatatt aaatgaaaca gcatggtttg gaagaggggc tgtaggtgca    60
ctaacagatg aagtaaagag aagaggatat cagaaggctt taatagtaac tgataagacg   120
cttgtacaat gtggtgtagt tgctaaagta acagataaaa tggatgctgc aggacttgca   180
tgggctattt atgatggtgt agtccctaat cctactactga ctgtagtaaa agagggcctt   240
ggagtatttc aaaattcagg tgcagattat ttgatagcta taggcggcgg ctctcctcaa   300
gatacttgta aagccattgg aataattagc aacaatcctg aatttgccga cgttagatca   360
cttgaaggat tatctcctac aaataaacca agcgtaccta tacttgcaat acctactaca   420
gcgggtactg cagctgaagt tacaataaac tatgtaatta cagacgaaga aaagagaaga   480
aaatttgtat gtgtagaccc tcatgacata cctcaagtag catttattga tgcagacatg   540
atggatggaa tgccccctgc tttaaaagca gcaactggtg tagatgcatt gacccatgct   600
atagaaggat atattactcg cggggcatgg gctttaaccg atgcactgca tataaaggct   660
atagaaataa tagctgggc attgagaggt tctgtagctg tgacaaaga tgctggtgaa   720
gagatggcgt taggtcagta tgtagcggga atgggatttt caaatgtagg gttaggatta   780
gttcacggta tggctcatcc tttaggtgca ttctataata caccacatgg agtagctaat   840
gctatactac taccacatgt tatgagatat aatgcagatt ttaccggaga aaaatataga   900
gatatagcac gagttatggg tgtaaaagta aaggaatga gctagaagaa ggctagaaat   960
gcagcagtag aagcagtatt tgctttaaat agagatgtag gaataccacc acatttaaga  1020
gatgttggtg taagaaaaga ggatattcca gcactggcac aggcagcatt ggatgatgta  1080
tgtacaggcg gcaatccaag agaggctaca cttgaagata tagtagagct ttatcatact  1140
gcatggtaa                                                          1149
```

| SEQ ID NO: 66 | moltype = AA   length = 382 |
| --- | --- |
| FEATURE | Location/Qualifiers |
| source | 1..382 |
|  | mol_type = protein |
|  | organism = Escherichia coli |

SEQUENCE: 66
```
MANRMILNET AWFGRGAVGA LTDEVKRRGY QKALIVTDKT LVQCGVVAKV TDKMDAAGLA   60
WAIYDGVVPN PTITVVKEGL GVFQNSGADY LIAIGGGSPQ DTCKAIGIIS NNPEFADVRS  120
LEGLSPTNKP SVPILAIPTT AGTAAEVTIN YVITDEEKRR KFVCVDPHDI PQVAFIDADM  180
MDGMPPALKA ATGVDALTHA IEGYITRGAW ALTDALHIKA IEIIAGALRG SVAGDKDAGE  240
EMALGQYVAG MGFSNVGLGL VHGMAHPLGA FYNTPHGVAN AILLPHVMRY NADFTGEKYR  300
DIARVMGVKV EGMSLEEARN AAVEAVFALN RDVGIPPHLR DVGVRKEDIP ALAQAALDDV  360
CTGGNPREAT LEDIVELYHT AW                                          382
```

| SEQ ID NO: 67 | moltype = DNA   length = 1155 |
| --- | --- |
| FEATURE | Location/Qualifiers |
| misc_feature | 1..1155 |
|  | note = Codon-adapted nucleotide sequence |
| source | 1..1155 |
|  | mol_type = other DNA |
|  | organism = synthetic construct |

SEQUENCE: 67
```
atgacaaata gaatgatatt aaatgaaact agttatatag gtgctggagc aatagaaaac    60
atagtaacag aggcaaaaac acgaggttat aaaaaggcac ttgttgtaac agataaagaa   120
ttaattaaat ttaatgttgc cagcaaagta accaatttgt aaaataaaaa tgatctaata   180
tttgagattt ttgatgaagt aaaagcaaat ccaactataa atgtagtatt agctggtata   240
gaaagattta aggcttcagg agcagattat cttatagcta taggcggcgg ctcttcaata   300
gatactgcta aagcaattgg tataataata ataatccag aatttagtga tgttagatca   360
cttgaaggtg ctgtagaaac aaaaaataaa tgtgtaagta taatagcagt tccaactaca   420
gcaggcactg ctgctgaagt aactataaat tatgttataa cagatgaaga agaaaagaga   480
aaatttgtat gtgttgatcc tcatgatatt ccagttattg cagtagtaga tagtgagatg   540
atgtcaagca tgcctaaggg attaacagct gcaactggaa tggatgcttt aactcatgct   600
atagaaggat atattacaaa aggagcatgg aactaacag atactctaca tttaaaggct   660
attgaaataa taggaagaag cttaaggtca gctgtaaata atgaacctaa aggaagagaa   720
gatatggcat taggacaata tatagcagga atgggttttt ccaatgttgg attgggaata   780
gttcattcta tggcgcaccc attgggtgct ttttatgata ctcttcacgg aatagcaaat   840
gctgtacttt tacctatgt aatggagtat aatgcagagg ctactgatga aaagtacagg   900
gaaatagcga gagtaatggg tgtagaaggt gtagataaca tgtctcaaaa agaatacaga   960
aaggctgcaa ttgatgctgt taaaaagctc tccgaagatg taggtatacc aaaggtactt  1020
aatgaaatcg gagtaaaaga agaggatctt caatctttag cagaatcagc ttttgtagat  1080
gcatgcacgc ctggtaaccc aagggatact tcagttgtag aaatactgga atatataaa   1140
aaggcattca aataa                                                   1155
```

| SEQ ID NO: 68 | moltype = AA   length = 384 |
| --- | --- |
| FEATURE | Location/Qualifiers |
| source | 1..384 |
|  | mol_type = protein |
|  | organism = Clostridium beijerinckii |

SEQUENCE: 68
```
MTNRMILNET SYIGAGAIEN IVTEAKTRGY KKALVVTDKE LIKFNVASKV TNLLNKNDLI   60
FEIFDEVKAN PTINVVLAGI ERFKASGADY LIAIGGGSSI DTAKAIGIII NNPEFSDVRS  120
LEGAVETKNK CVDIIAVPTT AGTAAEVTIN YVITDEERKR KFVCVDPHDI PVIAVVDSEM  180
MSSMPKGLTA ATGMDALTHA IEGYITKGAW ELTDTLHLKA IEIIGRSLRS AVNNEPKGRE  240
DMALGQYIAG MGFSNVGLGI VHSMAHPLGA FYDTLHGIAN AVLLPYVMEY NAEATDEKYR  300
EIARVMGVEG VDNMSQKEYR KAAIDAVKKL SEDVGIPKVL NEIGVKEEDL QSLAESAFVD  360
ACTPGNPRDT SVVEILEIYK KAFK                                        384
```

| SEQ ID NO: 69 | moltype = DNA   length = 37 |
| --- | --- |
| FEATURE | Location/Qualifiers |
| misc_feature | 1..37 |
|  | note = Synthetic oligo |
| source | 1..37 |
|  | mol_type = other DNA |
|  | organism = synthetic construct |

SEQUENCE: 69
```
cacaccaggt ctcaaaccat ggagatctcg aggcctg                             37
```

| SEQ ID NO: 70 | moltype = DNA   length = 37 |
| --- | --- |
| FEATURE | Location/Qualifiers |
| misc_feature | 1..37 |
|  | note = Synthetic oligo |
| source | 1..37 |
|  | mol_type = other DNA |
|  | organism = synthetic construct |

SEQUENCE: 70
```
cacaccaggt ctcacatatg ataagaagac tcttggc                             37
```

```
SEQ ID NO: 71            moltype = DNA   length = 36
FEATURE                  Location/Qualifiers
misc_feature             1..36
                         note = Synthetic oligo
source                   1..36
                         mol_type = other DNA
                         organism = synthetic construct
SEQUENCE: 71
cacaccaggt ctcacatatg acagcaacaa ggggcc                              36

SEQ ID NO: 72            moltype = DNA   length = 69
FEATURE                  Location/Qualifiers
misc_feature             1..69
                         note = Synthetic oligo
source                   1..69
                         mol_type = other DNA
                         organism = synthetic construct
SEQUENCE: 72
cacaccaggt ctcaattgta acacctcctt aattagttat gctctttctt ctataggtac    60
aaattttg                                                             69

SEQ ID NO: 73            moltype = DNA   length = 41
FEATURE                  Location/Qualifiers
misc_feature             1..41
                         note = Synthetic oligo
source                   1..41
                         mol_type = other DNA
                         organism = synthetic construct
SEQUENCE: 73
cacaccaggt ctcacaatga aaacaagaac tcaacaaata g                        41

SEQ ID NO: 74            moltype = DNA   length = 62
FEATURE                  Location/Qualifiers
misc_feature             1..62
                         note = Synthetic oligo
source                   1..62
                         mol_type = other DNA
                         organism = synthetic construct
SEQUENCE: 74
cacaccaggt ctcagtgttc ctcctatgtg ttcttaaaat tgagattctt cagttgaacc    60
tg                                                                   62

SEQ ID NO: 75            moltype = DNA   length = 62
FEATURE                  Location/Qualifiers
misc_feature             1..62
                         note = Synthetic oligo
source                   1..62
                         mol_type = other DNA
                         organism = synthetic construct
SEQUENCE: 75
cacaccaggt ctcagtgttc ctcctatgtg ttcttaaaat tgagattctt cagttgaacc    60
tg                                                                   62

SEQ ID NO: 76            moltype = DNA   length = 50
FEATURE                  Location/Qualifiers
misc_feature             1..50
                         note = Synthetic oligo
source                   1..50
                         mol_type = other DNA
                         organism = synthetic construct
SEQUENCE: 76
cacaccaggt ctcaggttat gcatttagat atattgtttt tgtctgtacg               50

SEQ ID NO: 77            moltype = DNA   length = 44
FEATURE                  Location/Qualifiers
misc_feature             1..44
                         note = Synthetic oligo
source                   1..44
                         mol_type = other DNA
                         organism = synthetic construct
SEQUENCE: 77
cacaccaggt ctcacatatg caatttaggc cttttaatcc acca                     44
```

```
SEQ ID NO: 78            moltype = DNA  length = 53
FEATURE                  Location/Qualifiers
misc_feature             1..53
                         note = Synthetic oligo
source                   1..53
                         mol_type = other DNA
                         organism = synthetic construct
SEQUENCE: 78
cacaccaggt ctcagtgttc ctcctatgtg ttcttatgct tgcgcaagtg cct          53

SEQ ID NO: 79            moltype = DNA  length = 44
FEATURE                  Location/Qualifiers
misc_feature             1..44
                         note = Synthetic oligo
source                   1..44
                         mol_type = other DNA
                         organism = synthetic construct
SEQUENCE: 79
cacaccaggt ctcaacacat atgtcttcag tgcctgtatt ccag                     44

SEQ ID NO: 80            moltype = DNA  length = 42
FEATURE                  Location/Qualifiers
misc_feature             1..42
                         note = Synthetic oligo
source                   1..42
                         mol_type = other DNA
                         organism = synthetic construct
SEQUENCE: 80
cacaccaggt ctcaggttaa gactggagat atactgcatg ag                       42

SEQ ID NO: 81            moltype = DNA  length = 40
FEATURE                  Location/Qualifiers
misc_feature             1..40
                         note = Synthetic oligo
source                   1..40
                         mol_type = other DNA
                         organism = synthetic construct
SEQUENCE: 81
cacaccaggt ctcacatatg agaactccat ttattatgac                          40

SEQ ID NO: 82            moltype = DNA  length = 52
FEATURE                  Location/Qualifiers
misc_feature             1..52
                         note = Synthetic oligo
source                   1..52
                         mol_type = other DNA
                         organism = synthetic construct
SEQUENCE: 82
cacaccaggt ctcagtgttc ctcctatgtg ttcctaatct acaaagtgct tg            52
```

MICROORGANISMS AND METHODS FOR IMPROVED BIOLOGICAL PRODUCTION OF ETHYLENE GLYCOL

CROSS REFERENCE TO RELATED APPLICATIONS

This application claims the benefit of U.S. Provisional Patent Application Nos. 63/260,054 filed on Aug. 6, 2021, and 63/261,185 filed on Sep. 14, 2021, the entirety of which is incorporated herein by reference.

REFERENCE TO A SEQUENCE LISTING

The application contains a Sequence Listing which has been submitted electronically in ST.26 Sequence listing XML format and is hereby incorporated by reference in its entirety. Said ST.26 Sequence listing XML, created on Jul. 21, 2022, is named LT199US1-Sequences.xml and is 156,945 bytes in size.

FIELD

The present disclosure relates to genetically engineered microorganisms and methods for the production of ethylene glycol and ethylene glycol precursors by microbial fermentation, particularly by microbial fermentation of a gaseous substrate.

BACKGROUND

Ethylene glycol, also known as monoethylene glycol (MEG), has a current market value of over $33 billion USD and is an important component of a huge variety of industrial, medical, and consumer products. Ethylene glycol is currently produced using chemical catalysis processes that require large amounts of energy and water, generate a number of undesirable by-products, and rely on petrochemical feedstocks. Demand for sustainable materials has led to some technological advancements, such as the catalytic production of ethylene glycol from sugar-cane derived ethanol.

Ethylene glycol precursors are also commercially valuable. For example, glycolate is used in skin care, personal care, dyeing, tanning, and as a cleaning agent. Glyoxylate is an intermediate for vanillin, agricultural chemicals, antibiotics, allantoin, and complexing agents.

However, no microorganisms are known to be capable of biologically producing ethylene glycol, and no fully biological route to the production of ethylene glycol has been well-established. Some biological routes to ethylene glycol have been described in the literature from sugars. For example, Alkim et al., *Microb Cell Fact*, 14: 127, 2015 demonstrated ethylene glycol production from (D)-xylose in *E. coli* but noted that aerobic conditions were required to achieve high yields. Similarly, Pereira et al., *Metab Eng*, 34: 80-87, 2016 achieved ethylene glycol production from pentoses in *E. coli*. A few studies on ethylene glycol production from pentoses have also been conducted in *S. cerevisiae* but have shown inconsistent results. See, e.g., Uranukul et al., *Metab Eng*, 51: 20-31, 2018.

Gas fermentation offers a route to use a wide range of readily available, low cost C1 feedstocks such as industrial waste gases, syngas, or reformed methane into chemicals and fuels. Since gas fermentation metabolism is significantly different from sugar-fermenting metabolism, use of the above-mentioned routes is not practical, as these routes would require production of sugar precursors from gas via gluconeogenesis, an energy negative process. To date, no route to produce ethylene glycol from gaseous substrates is available.

In an explorative exercise, Islam et al., *Metab Eng*, 41: 173-181, 2017 predicted hundreds of hypothetical pathways for producing ethylene glycol from syngas in *M. thermoacetica* using cheminformatics tools. However, it is not possible even for a skilled person in the art to incorporate these pathways in a gas fermenting organism, as many of the pathways are infeasible either due to thermodynamic or other constraints. For example, nearly 2,000 oxygen or oxygen radical-dependent reactions were included in Islam et al., which would not be feasible in a strictly anaerobic system. The only identified hypothetical pathways by Islam et al. that have known reactions require gluconeogenesis or ethanol as an intermediate. Therefore, there remains a need for validated, energetically favorable recombinant production systems that can produce high yields of ethylene glycol and ethylene glycol precursors from gaseous substrates.

SUMMARY

It is against the above background that the present disclosure provides certain advantages and advancements over the prior art.

Although this disclosure disclosed herein is not limited to specific advantages or functionalities, the disclosure provides a genetically engineered microorganism capable of producing ethylene glycol or a precursor of ethylene glycol from a gaseous substrate.

In some aspects of the microorganism disclosed herein, the microorganism produces ethylene glycol or the precursor of ethylene glycol through one or more intermediates comprising a disruptive mutation in a gene encoding diol dehydratase.

In some aspects of the microorganism disclosed herein, the microorganism produces ethylene glycol or the precursor of ethylene glycol through one or more intermediates selected from the group consisting of 5,10-methylenetetrahydrofolate, oxaloacetate, citrate, malate, and glycine.

In some aspects of the microorganism disclosed herein, the microorganism comprises one or more of a heterologous enzyme capable of converting oxaloacetate to citrate, a heterologous enzyme capable of converting glycine to glyoxylate, a heterologous enzyme capable of converting iso-citrate to glyoxylate, and a heterologous enzyme capable of converting glycolate to glycolaldehyde.

In some aspects of the microorganism disclosed herein, the heterologous enzyme capable of converting oxaloacetate to citrate is a citrate [Si]-synthase [2.3.3.1], an ATP citrate synthase [2.3.3.8]; or a citrate (Re)-synthase [2.3.3.3]; the heterologous enzyme capable of converting glycine to glyoxylate is an alanine-glyoxylate transaminase [2.6.1.44], a serine-glyoxylate transaminase [2.6.1.45], a serine-pyruvate transaminase [2.6.1.51], a glycine-oxaloacetate transaminase [2.6.1.35], a glycine transaminase [2.6.1.4], a glycine dehydrogenase [1.4.1.10], an alanine dehydrogenase [1.4.1.1], or a glycine dehydrogenase [1.4.2.1]; the heterologous enzyme capable of converting iso-citrate to glyoxylate is an isocitrate lyase [4.1.3.1]; and/or the heterologous enzyme capable of converting glycolate to glycolaldehyde is a glycolaldehyde dehydrogenase [1.2.1.21], a lactaldehyde dehydrogenase [1.2.1.22], a succinate-semialdehyde dehydrogenase [1.2.1.24], a 2,5-dioxovalerate dehydrogenase [1.2.1.26], an aldehyde dehydrogenase [1.2.1.3/4/5], a betaine-aldehyde dehydrogenase [1.2.1.8], or an aldehyde ferredoxin oxidoreductase [1.2.7.5].

In some aspects of the microorganism disclosed herein, the heterologous enzymes are derived from a genus selected from the group consisting of *Bacillus, Clostridium, Escherichia, Gluconobacter, Hyphomicrobium, Lysinibacillus, Paenibacillus, Pseudomonas, Sedimenticola, Sporosarcina, Streptomyces, Thermithiobacillus, Thermotoga,* and *Zea.*

In some aspects of the microorganism disclosed herein, one or more of the heterologous enzymes are codon-optimized for expression in the microorganism.

In some aspects of the microorganism disclosed herein, the microorganism further comprises one or more of an enzymes capable of converting acetyl-CoA to pyruvate; an enzyme capable of converting pyruvate to oxaloacetate; an enzyme capable of converting pyruvate to malate; an enzyme capable of converting pyruvate to phosphoenolpyruvate; an enzyme capable of converting oxaloacetate to citryl-CoA; an enzyme capable of converting citryl-CoA to citrate; an enzyme capable of converting citrate to aconitate and aconitate to iso-citrate; an enzyme capable of converting phosphoenolpyruvate to oxaloacetate; an enzyme capable of converting phosphoenolpyruvate to 2-phospho-D-glycerate; an enzyme capable of converting 2-phospho-D-glycerate to 3-phospho-D-glycerate; an enzyme capable of converting 3-phospho-D-glycerate to 3-phosphonooxypyruvate; an enzyme capable of converting 3-phosphonooxypyruvate to 3-phospho-L-serine; an enzyme capable of converting 3-phospho-L-serine to serine; an enzyme capable of converting serine to glycine; an enzyme capable of converting 5,10-methylenetetrahydrofolate to glycine; an enzyme capable of converting serine to hydroxypyruvate; an enzyme capable of converting D-glycerate to hydroxypyruvate; an enzyme capable of converting malate to glyoxylate; an enzyme capable of converting glyoxylate to glycolate; an enzyme capable of converting hydroxypyruvate to glycolaldehyde; and/or an enzyme capable of converting glycolaldehyde to ethylene glycol.

In some aspects of the microorganism disclosed herein, the microorganism overexpresses the heterologous enzyme capable of converting oxaloacetate to citrate, the heterologous enzyme capable of converting glycine to glyoxylate, and/or the heterologous enzyme capable of converting glycolate to glycolaldehyde.

In some aspects of the microorganism disclosed herein, the microorganism overexpresses the enzyme capable of converting pyruvate to oxaloacetate, the enzyme capable of converting citrate to aconitate and aconitate to iso-citrate, the enzyme capable of converting phosphoenolpyruvate to oxaloacetate, the enzyme capable of converting serine to glycine, the enzyme capable of converting 5,10-methylenetetrahydrofolate to glycine, the enzyme capable of converting glyoxylate to glycolate; and/or the enzyme capable of converting glycolaldehyde to ethylene glycol.

In some aspects of the microorganism disclosed herein, the microorganism comprises a disruptive mutation in one or more enzymes selected from the group consisting of isocitrate dehydrogenase, glycerate dehydrogenase, glycolate dehydrogenase, glycerate dehydrogenase, glycolate dehydrogenase, aldehyde ferredoxin oxidoreductase, and aldehyde dehydrogenase In some aspects of the microorganism disclosed herein, the microorganism is a member of a genus selected from the group consisting of *Acetobacterium, Alkalibaculum, Blautia, Butyribacterium, Clostridium, Cupriavidus, Eubacterium, Moorella, Oxobacter, Sporomusa,* and *Thermoanaerobacter.*

In some aspects of the microorganism disclosed herein, the microorganism is derived from a parental microorganism selected from the group consisting of *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Cupriavidus necator, Eubacterium limosum, Moorella thermautotrophica, Moorella thermoacetica, Oxobacter pfennigii, Sporomusa ovata, Sporomusa silvacetica, Sporomusa sphaeroides,* and *Thermoanaerobacter kiuvi.*

In some aspects of the microorganism disclosed herein, the microorganism is derived from a parental bacterium selected from the group consisting of *Clostridium autoethanogenum, Clostridium ljungdahlii,* and *Clostridium ragsdalei.*

In some aspects of the microorganism disclosed herein, the microorganism comprises a native or heterologous Wood-Ljungdahl pathway.

In some aspects of the microorganism disclosed herein, the microorganism produces glyoxylate or glycolate as a precursor of ethylene glycol.

The disclosure further provides a method of producing ethylene glycol or a precursor of ethylene glycol comprising culturing the microorganism disclosed herein in a nutrient medium and in the presence of a substrate, whereby the microorganism produces ethylene glycol or the precursor of ethylene glycol.

In some aspects of the method disclosed herein, the substrate comprises one or more of CO, $CO_2$, and $H_2$.

In some aspects of the method disclosed herein, at least a portion of the substrate is industrial waste gas, industrial off gas, or syngas.

In some aspects of the method disclosed herein, the microorganism produces glyoxylate or glycolate as precursors of ethylene glycol.

In some aspects of the method disclosed herein, the method further comprises separating the ethylene glycol or the ethylene glycol precursor from the nutrient medium.

In some aspects of the method disclosed herein, the microorganism further produces one or more of ethanol, 2,3-butanediol, and succinate.

The disclosure further provides a composition comprising ethylene glycol produced by the method described herein. In some aspects, the composition is an antifreeze, a preservative, a dehydrating agent, or a drilling fluid.

The disclosure further provides a polymer comprising ethylene glycol produced by the method described herein. In some aspects, the polymer is a homopolymer or a copolymer. In some aspects, the polymer is polyethylene glycol (PEG) or polyethylene terephthalate (PET).

The disclosure further provides a method of producing a polyethylene terephthalate (PET) product from a gaseous substrate comprising 1) forming at least one PET component, wherein the at least one PET component is selected from monoethylene glycol, a terephthalic acid (PTA), or any combinations thereof; 2) processing the at least one PET component into PET; 3) polymerizing the PET to form a PET resin; and 4) processing the PET resin into a PET product. The disclosure provides that the PTA may be derived from fossil sources, or either directly or indirectly from gas fermentation. Examples of PET products may be those disclosed in US 2020/0048665A1, hereby incorporated by reference in its entirety.

The disclosure provides a method for producing a PET polymer from a gaseous substrate comprising 1) providing at least one diacid compound, comprising a terephthalate compound; 2) providing at least one diol compound, comprising monoethylene glycol, 3) copolymerizing a mixture of the diacid compound and the diol compound to obtain a PET polymer comprising diacid components and diol components.

The disclosure further provides a composition comprising the polymer described herein. In some aspects, the composition is a fiber, a resin, a film, or a plastic.

These and other features and advantages of the present disclosure will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which:

FIG. 2A is a map of expression shuttle vector, pIPL12, as described in Example 1. FIG. 2B is a map of plasmid pMEG042, which comprises *B. subtilis* citrate synthase, *E. coli* isocitrate lyase, and *G. oxydans* glycolaldehyde dehydrogenase, as described in Example 1. FIG. 2C is a map of plasmid pMEG058, which comprises *S. thiotaurini* alanine-glyoxylate aminotransferase and *P. fluorescens* aldehyde dehydrogenase, as described in Example 2. FIG. 2D is a map of plasmid pMEG059, which comprises *S. thiotaurini* alanine-glyoxylate aminotransferase and *G. oxydans* aldehyde dehydrogenase, as described in Example 3. FIG. 2E is a map of plasmid pMEG061, which comprises *C. acidurici* class V aminotransferase and *P. fluorescens* aldehyde dehydrogenase, as described in Example 4.

DETAILED DESCRIPTION

Figure 1:
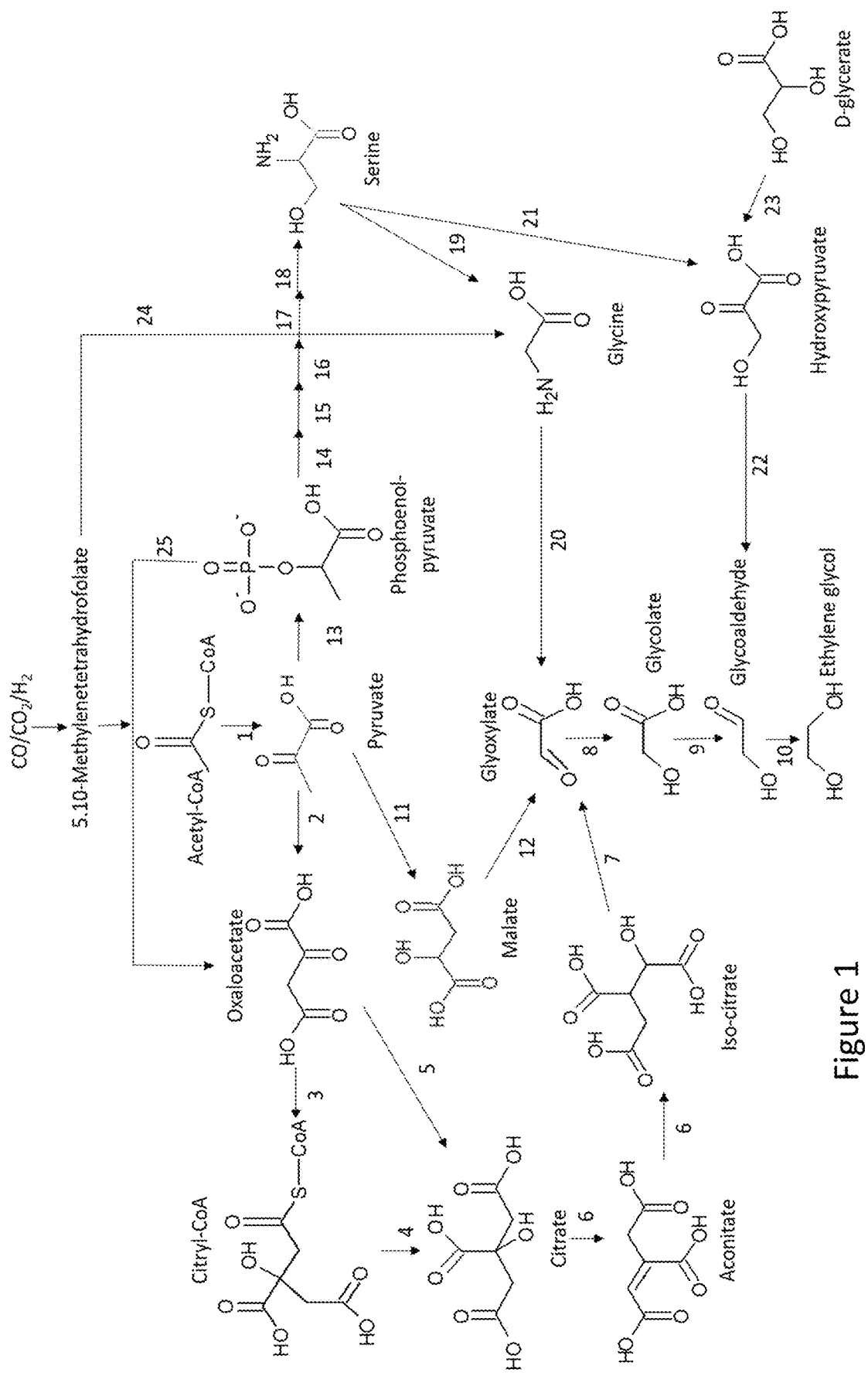
FIG. 1 is a schematic showing pathways for the production of ethylene glycol, glycolate, and glyoxylate from a gaseous substrate comprising CO, $CO_2$, and/or $H_2$.

The following description of embodiments is given in general terms. The disclosure is further elucidated from the disclosure given under the heading "Examples" herein below, which provides experimental data supporting the disclosure, specific examples of various aspects of the disclosure, and means of performing the disclosure.

The inventors have surprisingly been able to engineer a carboxydotrophic acetogenic microorganism to produce ethylene glycol or a precursor of ethylene glycol by fermentation of a substrate comprising CO and/or $CO_2$ comprising a disruptive mutation in a gene encoding diol dehydratase.

Unless otherwise defined, the following terms as used throughout this specification are defined as follows:

The disclosure provides microorganisms for the biological production of ethylene glycol. A "microorganism" is a microscopic organism, especially a bacterium, archaeon, virus, or fungus. In a preferred embodiment, the microorganism of the disclosure is a bacterium.

The term "non-naturally occurring" when used in reference to a microorganism is intended to mean that the microorganism has at least one genetic modification not found in a naturally occurring strain of the referenced species, including wild-type strains of the referenced species. Non-naturally occurring microorganisms are typically developed in a laboratory or research facility. The microorganisms of the disclosure are non-naturally occurring.

The terms "genetic modification," "genetic alteration," or "genetic engineering" broadly refer to manipulation of the genome or nucleic acids of a microorganism by the hand of man. Likewise, the terms "genetically modified," "genetically altered," or "genetically engineered" refers to a microorganism containing such a genetic modification, genetic alteration, or genetic engineering. These terms may be used to differentiate a lab-generated microorganism from a naturally-occurring microorganism. Methods of genetic modification of include, for example, heterologous gene expression, gene or promoter insertion or deletion, nucleic acid mutation, altered gene expression or inactivation, enzyme engineering, directed evolution, knowledge-based design, random mutagenesis methods, gene shuffling, and codon optimization. The microorganisms of the disclosure are genetically engineered.

"Recombinant" indicates that a nucleic acid, protein, or microorganism is the product of genetic modification, engineering, or recombination. Generally, the term "recombinant" refers to a nucleic acid, protein, or microorganism that contains or is encoded by genetic material derived from multiple sources, such as two or more different strains or species of microorganisms. The microorganisms of the disclosure are generally recombinant.

"Wild type" refers to the typical form of an organism, strain, gene, or characteristic as it occurs in nature, as distinguished from mutant or variant forms.

"Endogenous" refers to a nucleic acid or protein that is present or expressed in the wild-type or parental microorganism from which the microorganism of the disclosure is derived. For example, an endogenous gene is a gene that is natively present in the wild-type or parental microorganism from which the microorganism of the disclosure is derived. In one embodiment, the expression of an endogenous gene may be controlled by an exogenous regulatory element, such as an exogenous promoter.

"Exogenous" refers to a nucleic acid or protein that originates outside the microorganism of the disclosure. For example, an exogenous gene or enzyme may be artificially or recombinantly created and introduced to or expressed in the microorganism of the disclosure. An exogenous gene or enzyme may also be isolated from a heterologous microorganism and introduced to or expressed in the microorganism of the disclosure. Exogenous nucleic acids may be adapted to integrate into the genome of the microorganism of the disclosure or to remain in an extra-chromosomal state in the microorganism of the disclosure, for example, in a plasmid.

"Heterologous" refers to a nucleic acid or protein that is not present in the wild-type or parental microorganism from which the microorganism of the disclosure is derived. For example, a heterologous gene or enzyme may be derived from a different strain or species and introduced to or expressed in the microorganism of the disclosure. The heterologous gene or enzyme may be introduced to or expressed in the microorganism of the disclosure in the form in which it occurs in the different strain or species. Alternatively, the heterologous gene or enzyme may be modified in some way, e.g., by codon-optimizing it for expression in the microorganism of the disclosure or by engineering it to alter function, such as to reverse the direction of enzyme activity or to alter substrate specificity.

In particular, a heterologous nucleic acid or protein expressed in the microorganism described herein may be derived from *Bacillus, Clostridium, Cupriavidus, Escherichia, Gluconobacter, Hyphomicrobium, Lysinibacillus, Paenibacillus, Pseudomonas, Sedimenticola, Sporosarcina, Streptomyces, Thermithiobacillus, Thermotoga, Zea, Klebsiella, Mycobacterium, Salmonella, Mycobacteroides, Staphylococcus, Burkholderia, Listeria, Acinetobacter, Shigella, Neisseria, Bordetella, Streptococcus, Enterobacter, Vibrio, Legionella, Xanthomonas, Serratia, Cronobacter, Cupriavidus, Helicobacter, Yersinia, Cutibacterium, Francisella, Pectobacterium, Arcobacter, Lactobacillus, Shewanella, Erwinia, Sulfurospirillum,* Peptococcaceae, *Thermococcus, Saccharomyces, Pyrococcus, Glycine, Homo, Ralstonia, Brevibacterium, Methylobacterium, Geobacillus, bos, gallus, Anaerococcus, Xenopus, Amblyrhynchus, rattus, mus, sus, Rhodococcus, Rhizobium, Megasphaera, Mesorhizobium, Peptococcus, Agrobacterium, Campylobacter, Acetobacterium, Alkalibaculum, Blautia, Butyribacterium, Eubacterium, Moorella, Oxobacter, Sporomusa, Thermoanaerobacter, Schizosaccharomyces, Paenibacillus, Fictibacillus, Lysinibacillus, Ornithinibacillus, Halobacillus, Kurthia, Lentibacillus, Anoxybacillus, Solibacillus, Virgibacillus, Alicyclobacillus,* Sporosarcina, Salimicrobium, Sporosarcina, *Planococcus, Corynebacterium, Thermaerobacter, Sulfobacillus,* or *Symbiobacterium.*

The terms "polynucleotide," "nucleotide," "nucleotide sequence," "nucleic acid," and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides or nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene products."

The terms "polypeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, by disulfide bond formation, glycosylation, lipidation, acetylation, phosphorylation, or any other manipulation, such as conjugation with a labeling component. As used herein, the term "amino acid" includes natural and/or unnatural or synthetic amino acids, including glycine and both the D or L optical isomers, and amino acid analogs and peptidomimetics.

"Enzyme activity," or simply "activity," refers broadly to enzymatic activity, including, but not limited to, the activity of an enzyme, the amount of an enzyme, or the availability of an enzyme to catalyze a reaction. Accordingly, "increasing" enzyme activity includes increasing the activity of an enzyme, increasing the amount of an enzyme, or increasing the availability of an enzyme to catalyze a reaction. Similarly, "decreasing" enzyme activity includes decreasing the activity of an enzyme, decreasing the amount of an enzyme, or decreasing the availability of an enzyme to catalyze a reaction.

"Mutated" refers to a nucleic acid or protein that has been modified in the microorganism of the disclosure compared to the wild-type or parental microorganism from which the microorganism of the disclosure is derived. In one embodiment, the mutation may be a deletion, insertion, or substitution in a gene encoding an enzyme. In another embodiment, the mutation may be a deletion, insertion, or substitution of one or more amino acids in an enzyme.

"Disrupted gene" refers to a gene that has been modified in some way to reduce or eliminate expression of the gene, regulatory activity of the gene, or activity of an encoded protein or enzyme. The disruption may partially inactivate, fully inactivate, or delete the gene or enzyme. The disruption may be a knockout (KO) mutation that fully eliminates the expression or activity of a gene, protein, or enzyme. The disruption may also be a knock-down that reduces, but does not entirely eliminate, the expression or activity of a gene, protein, or enzyme. The disruption may be anything that reduces, prevents, or blocks the biosynthesis of a product produced by an enzyme. The disruption may include, for example, a mutation in a gene encoding a protein or enzyme, a mutation in a genetic regulatory element involved in the expression of a gene encoding an enzyme, the introduction of a nucleic acid which produces a protein that reduces or inhibits the activity of an enzyme, or the introduction of a nucleic acid (e.g., antisense RNA, RNAi, TALEN, siRNA, CRISPR, or CRISPRi) or protein which inhibits the expression of a protein or enzyme. The disruption may be introduced using any method known in the art. For the purposes of the present disclosure, disruptions are laboratory-generated, not naturally occurring.

A "parental microorganism" is a microorganism used to generate a microorganism of the disclosure. The parental microorganism may be a naturally-occurring microorganism (i.e., a wild-type microorganism) or a microorganism that has been previously modified (i.e., a mutant or recombinant microorganism). The microorganism of the disclosure may be modified to express or overexpress one or more enzymes that were not expressed or overexpressed in the parental microorganism. Similarly, the microorganism of the disclosure may be modified to contain one or more genes that were not contained by the parental microorganism. The microorganism of the disclosure may also be modified to not express or to express lower amounts of one or more enzymes that were expressed in the parental microorganism.

The microorganism of the disclosure may be derived from essentially any parental microorganism. In one embodiment, the microorganism of the disclosure may be derived from a parental microorganism selected from the group consisting of *Clostridium acetobutylicum*, *Clostridium beijerinckii*, *Escherichia coli*, and *Saccharomyces cerevisiae*. In other embodiments, the microorganism is derived from a parental microorganism selected from the group consisting of *Acetobacterium woodii*, *Alkalibaculum bacchii*, *Blautia product*, *Butyribacterium methylotrophicum*, *Clostridium aceticum*, *Clostridium autoethanogenum*, *Clostridium carboxidivorans*, *Clostridium coskatii*, *Clostridium drakei*, *Clostridium formicoaceticum*, *Clostridium ljungdahlii*, *Clostridium magnum*, *Clostridium ragsdalei*, *Clostridium scatologenes*, *Eubacterium limosum*, *Moorella thermoautotrophica*, *Moorella thermoacetica*, *Oxobacter pfennigii*, *Sporomusa ovata*, *Sporomusa silvacetica*, *Sporomusa sphaeroides*, and *Thermoanaerobacter kivui*. In a preferred embodiment, the parental microorganism is *Clostridium autoethanogenum*, *Clostridium ljungdahlii*, or *Clostridium ragsdalei*. In an especially preferred embodiment, the parental microorganism is *Clostridium autoethanogenum* LZ1561, which was deposited on Jun. 7, 2010 with Deutsche Sammlung von Mikroorganismen und Zellkulturen GmbH (DSMZ) located at Inhoffenstraße 7B, D-38124 Braunschweig, Germany on Jun. 7, 2010 under the terms of the Budapest Treaty and accorded accession number DSM23693. This strain is described in International Patent Application No. PCT/NZ2011/000144, which published as WO 2012/015317.

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the disclosure is derived from a parental microorganism. In one embodiment, the microorganism of the disclosure is derived from *Clostridium autoethanogenum*, *Clostridium ljungdahlii*, or *Clostridium ragsdalei*. In a preferred embodiment, the microorganism of the disclosure is derived from *Clostridium autoethanogenum* LZ1561, which is deposited under DSMZ accession number DSM23693.

The microorganism of the disclosure may be further classified based on functional characteristics. For example, the microorganism of the disclosure may be or may be derived from a C1-fixing microorganism, an anaerobe, an acetogen, an ethanologen, a carboxydotroph, and/or a methanotroph.

Table 1 provides a representative list of microorganisms and identifies their functional characteristics.

TABLE 1

| | Wood-Ljungdahl | C1-fixing | Anaerobe | Acetogen | Ethanologen | Autotroph | Carboxydotroph |
|---|---|---|---|---|---|---|---|
| *Acetobacterium woodii* | + | + | + | + | +/– [1] | + | – |
| *Alkalibaculum bacchii* | + | + | + | + | + | + | + |
| *Blautia producta* | + | + | + | + | – | + | + |
| *Butyribacterium methylotrophicum* | + | + | + | + | + | + | + |
| *Clostridium aceticum* | + | + | + | + | – | + | + |
| *Clostridium autoethanogenum* | + | + | + | + | + | + | + |
| *Clostridium carboxidivorans* | + | + | + | + | + | + | + |
| *Clostridium coskatii* | + | + | + | + | + | + | + |
| *Clostridium drakei* | + | + | + | + | – | + | + |
| *Clostridium formicoaceticum* | + | + | + | + | – | + | + |
| *Clostridium ljungdahlii* | + | + | + | + | + | + | + |
| *Clostridium magnum* | + | + | + | + | – | + | +/– [2] |
| *Clostridium ragsdalei* | + | + | + | + | + | + | + |
| *Clostridium scatologenes* | + | + | + | + | – | + | + |
| *Eubacterium limosum* | + | + | + | + | – | + | + |

TABLE 1-continued

| | Wood-Ljungdahl | C1-fixing | Anaerobe | Acetogen | Ethanologen | Autotroph | Carboxydotroph |
|---|---|---|---|---|---|---|---|
| *Moorella thermautotrophica* | + | + | + | + | + | + | + |
| *Moorella thermoacetica* (formerly *Clostridium thermoaceticum*) | + | + | + | + | −[3] | + | + |
| *Oxobacter pfennigii* | + | + | + | + | − | + | + |
| *Sporomusa ovata* | + | + | + | + | − | + | +/−[4] |
| *Sporomusa silvacetica* | + | + | + | + | − | + | +/−[5] |
| *Sporomusa sphaeroides* | + | + | + | + | − | + | +/−[6] |
| *Thermoanaerobacter kivui* | + | + | + | + | − | + | − |

[1] *Acetobacterium woodii* can produce ethanol from fructose, but not from gas.
[2] It has not been investigated whether *Clostridium magnum* can grow on CO.
[3] One strain of *Moorella thermoacetica*, *Moorella* sp. HUC22-1, has been reported to produce ethanol from gas.
[4] It has not been investigated whether *Sporomusa ovata* can grow on CO.
[5] It has not been investigated whether *Sporomusa silvacetica* can grow on CO.
[6] It has not been investigated whether *Sporomusa sphaeroides* can grow on CO.

"Wood-Ljungdahl" refers to the Wood-Ljungdahl pathway of carbon fixation as described, e.g., by Ragsdale, *Biochim Biophys Acta*, 1784: 1873-1898, 2008. "Wood-Ljungdahl microorganisms" refers, predictably, to microorganisms containing the Wood-Ljungdahl pathway. Often, the microorganism of the disclosure contains a native Wood-Ljungdahl pathway. Herein, a Wood-Ljungdahl pathway may be a native, unmodified Wood-Ljungdahl pathway or it may be a Wood-Ljungdahl pathway with some degree of genetic modification (e.g., overexpression, heterologous expression, knockout, etc.) so long as it still functions to convert CO, $CO_2$, and/or $H_2$ to acetyl-CoA.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the disclosure. For example, a C1-carbon source may comprise one or more of CO, $CO_2$, $CH_4$, $CH_3OH$, or $CH_2O_2$. Preferably, the C1-carbon source comprises one or both of CO and $CO_2$. A "C1-fixing microorganism" is a microorganism that has the ability to produce one or more products from a C1-carbon source. Often, the microorganism of the disclosure is a C1-fixing bacterium. In a preferred embodiment, the microorganism of the disclosure is derived from a C1-fixing microorganism identified in Table 1.

An "anaerobe" is a microorganism that does not require oxygen for growth. An anaerobe may react negatively or even die if oxygen is present above a certain threshold. However, some anaerobes are capable of tolerating low levels of oxygen (e.g., 0.000001-5% oxygen), sometimes referred to as "microoxic conditions." Often, the microorganism of the disclosure is an anaerobe. In a preferred embodiment, the microorganism of the disclosure is derived from an anaerobe identified in Table 1.

"Acetogens" are obligately anaerobic bacteria that use the Wood-Ljungdahl pathway as their main mechanism for energy conservation and for synthesis of acetyl-CoA and acetyl-CoA-derived products, such as acetate (Ragsdale, *Biochim Biophys Acta*, 1784: 1873-1898, 2008). In particular, acetogens use the Wood-Ljungdahl pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, 3$^{rd}$ edition, p. 354, New York, NY, 2006). All naturally occurring acetogens are C1-fixing, anaerobic, autotrophic, and non-methanotrophic. Often, the microorganism of the disclosure is an acetogen. In a preferred embodiment, the microorganism of the disclosure is derived from an acetogen identified in Table 1.

An "ethanologen" is a microorganism that produces or is capable of producing ethanol. Often, the microorganism of the disclosure is an ethanologen. In a preferred embodiment, the microorganism of the disclosure is derived from an ethanologen identified in Table 1.

An "autotroph" is a microorganism capable of growing in the absence of organic carbon. Instead, autotrophs use inorganic carbon sources, such as CO and/or $CO_2$. Often, the microorganism of the disclosure is an autotroph. In a preferred embodiment, the microorganism of the disclosure is derived from an autotroph identified in Table 1.

A "carboxydotroph" is a microorganism capable of utilizing CO as a sole source of carbon and energy. Often, the microorganism of the disclosure is a carboxydotroph. In a preferred embodiment, the microorganism of the disclosure is derived from a carboxydotroph identified in Table 1.

A "methanotroph" is a microorganism capable of utilizing methane as a sole source of carbon and energy. In certain embodiments, the microorganism of the disclosure is a methanotroph or is derived from a methanotroph. In other embodiments, the microorganism of the disclosure is not a methanotroph or is not derived from a methanotroph.

In a preferred embodiment, the microorganism of the disclosure is derived from the cluster of Clostridia comprising the species *Clostridium autoethanogenum*, *Clostridium ljungdahlii*, and *Clostridium ragsdalei*. These species were first reported and characterized by Abrini, *Arch Microbiol*, 161: 345-351, 1994 (*Clostridium autoethanogenum*), Tanner, *Int J System Bacteriol*, 43: 232-236, 1993 (*Clostridium ljungdahlii*), and Huhnke, WO 2008/028055 (*Clostridium ragsdalei*).

These three species have many similarities. In particular, these species are all C1-fixing, anaerobic, acetogenic, ethanologenic, and carboxydotrophic members of the genus *Clostridium*. These species have similar genotypes and phenotypes and modes of energy conservation and fermentative metabolism. Moreover, these species are clustered in clostridial rRNA homology group I with 16S rRNA DNA that is more than 99% identical, have a DNA G+C content of about 22-30 mol %, are gram-positive, have similar morphology and size (logarithmic growing cells between 0.5-0.7×3-5 μm), are mesophilic (grow optimally at 30-37° C.), have similar pH ranges of about 4-7.5 (with an optimal pH of about 5.5-6), lack cytochromes, and conserve energy via an Rnf complex. Also, reduction of carboxylic acids into their corresponding alcohols has been shown in these species (Perez, *Biotechnol Bioeng*, 110:1066-1077, 2012). Importantly, these species also all show strong autotrophic growth on CO-containing gases, produce ethanol and acetate (or acetic acid) as main fermentation products, and produce small amounts of 2,3-butanediol and lactic acid under certain conditions.

However, these three species also have a number of differences. These species were isolated from different sources: *Clostridium autoethanogenum* from rabbit gut, *Clostridium ljungdahlii* from chicken yard waste, and *Clostridium ragsdalei* from freshwater sediment. These species differ in utilization of various sugars (e.g., rhamnose, arabinose), acids (e.g., gluconate, citrate), amino acids (e.g., arginine, histidine), and other substrates (e.g., betaine, butanol). Moreover, these species differ in auxotrophy to certain vitamins (e.g., thiamine, biotin). These species have differences in nucleic and amino acid sequences of Wood-Ljungdahl pathway genes and proteins, although the general organization and number of these genes and proteins has been found to be the same in all species (Köpke, *Curr Opin Biotechnol*, 22: 320-325, 2011).

Thus, in summary, many of the characteristics of *Clostridium autoethanogenum, Clostridium ljungdahlii*, or *Clostridium ragsdalei* are not specific to that species, but are rather general characteristics for this cluster of C1-fixing, anaerobic, acetogenic, ethanologenic, and carboxydotrophic members of the genus *Clostridium*. However, since these species are, in fact, distinct, the genetic modification or manipulation of one of these species may not have an identical effect in another of these species. For instance, differences in growth, performance, or product production may be observed.

The microorganism of the disclosure may also be derived from an isolate or mutant of *Clostridium autoethanogenum, Clostridium ljungdahlii*, or *Clostridium ragsdalei*. Isolates and mutants of *Clostridium autoethanogenum* include JA1-1 (DSM10061) (Abrini, *Arch Microbiol*, 161: 345-351, 1994), LBS1560 (DSM19630) (WO 2009/064200), and LZ1561 (DSM23693) (WO 2012/015317). Isolates and mutants of *Clostridium ljungdahlii* include ATCC 49587 (Tanner, *Int J Syst Bacteriol*, 43: 232-236, 1993), PETCT (DSM13528, ATCC 55383), ERI-2 (ATCC 55380) (U.S. Pat. No. 5,593, 886), C-01 (ATCC 55988) (U.S. Pat. No. 6,368,819), O-52 (ATCC 55989) (U.S. Pat. No. 6,368,819), and OTA-1 (Tirado-Acevedo, Production of bioethanol from synthesis gas using *Clostridium ljungdahlii*, PhD thesis, North Carolina State University, 2010). Isolates and mutants of *Clostridium ragsdalei* include PI 1 (ATCC BAA-622, ATCC PTA-7826) (WO 2008/028055).

As described above, however, the microorganism of the disclosure may also be derived from essentially any parental microorganism, such as a parental microorganism selected from the group consisting of *Clostridium acetobutylicum, Clostridium beijerinckii, Escherichia coli*, and *Saccharomyces cerevisiae*.

The disclosure provides microorganisms capable of producing ethylene glycol, glyoxylate, and glycolate as well as methods of producing ethylene glycol, glyoxylate, and glycolate comprising culturing the microorganism of the disclosure in the presence of a substrate, whereby the microorganism produces ethylene glycol.

A microorganism of the disclosure may comprise an enzyme that converts acetyl-CoA, such as acetyl-CoA produced by the Wood-Ljungdahl pathway, to pyruvate (reaction 1 of FIG. 1). This enzyme may be a pyruvate synthase (PFOR) [1.2.7.1] or an ATP:pyruvate, orthophosphate phosphotransferase [1.2.7.1]. In some embodiments, the enzyme that converts acetyl-CoA to pyruvate is an endogenous enzyme.

A microorganism of the disclosure may comprise an enzyme that converts pyruvate to oxaloacetate (reaction 2 of FIG. 1). This enzyme may be a pyruvate:carbon-dioxide ligase [ADP-forming] [6.4.1.1]. In some embodiments, the enzyme that converts pyruvate to oxaloacetate is an endogenous enzyme. In some embodiments, the enzyme that converts pyruvate to oxaloacetate is overexpressed.

A microorganism of the disclosure may comprise an enzyme that converts oxaloacetate to citryl-CoA (reaction 3 of FIG. 1). This enzyme may be a citryl-CoA lyase [4.1.3.34]. In some embodiments, the enzyme that converts oxaloacetate to citryl-CoA is an endogenous enzyme.

A microorganism of the disclosure may comprise an enzyme that converts citryl-CoA to citrate (reaction 4 of FIG. 1). This enzyme may be a citrate-CoA transferase [2.8.3.10]. In some embodiments, the enzyme that converts citryl-CoA to citrate is an endogenous enzyme.

A microorganism of the disclosure may comprise an enzyme that converts oxaloacetate to citrate (reaction 5 of FIG. 1). This enzyme may be a citrate [Si]-synthase [2.3.3.1], an ATP citrate synthase [2.3.3.8], or a citrate (Re)-synthase [2.3.3.3]. In some embodiments, the enzyme that converts oxaloacetate to citrate is an endogenous enzyme. In other embodiments, the enzyme that converts oxaloacetate to citrate is a heterologous enzyme. For example, in some embodiments, a microorganism of the disclosure comprises citrate synthase 1 [EC 2.3.3.16] from *B. subtilis*, such that the microorganism comprises a nucleotide sequence set forth in SEQ ID NO: 1, which encodes the amino acid sequence set forth in SEQ ID NO: 2. In some embodiments, a microorganism of the disclosure comprises citrate (Re)-synthase from *C. kluyveri*, such that the microorganism comprises a nucleotide sequence set forth in SEQ ID NO: 3, which encodes the amino acid sequence set forth in SEQ ID NO: 4. In some embodiments, a microorganism of the disclosure comprises citrate (Si)-synthase from *Clostridium* sp., such that the microorganism comprises a nucleotide sequence set forth in SEQ ID NO: 5, which encodes the amino acid sequence set forth in SEQ ID NO: 6. In some embodiments, a microorganism of the disclosure comprises citrate synthase 2 from *B. subtilis*, such that the microorganism comprises a nucleotide sequence set forth in SEQ ID NO: 7, which encodes the amino acid sequence set forth in SEQ ID NO: 8. In some embodiments, the enzyme that converts oxaloacetate to citrate is overexpressed.

A microorganism of the disclosure may comprise an enzyme that converts citrate to aconitate and aconitate to iso-citrate (reactions 6 of FIG. 1). This enzyme may be an aconitate hydratase [4.2.1.3]. In some embodiments, the enzyme that converts citrate to aconitate and aconitate to iso-citrate is an endogenous enzyme. In some embodiments, the enzyme that converts citrate to aconitate and aconitate to iso-citrate is overexpressed.

A microorganism of the disclosure may comprise an enzyme that converts isocitrate to glyoxylate (reaction 7 of FIG. 1). This enzyme may be an isocitrate lyase [4.1.3.1]. In some embodiments, a microorganism of the disclosure comprises isocitrate lyase from *Z. mays*, such that the microorganism comprises a nucleotide sequence set forth in SEQ ID NO: 9, which encodes the amino acid sequence set forth in SEQ ID NO: 10. In some embodiments, a microorganism of the disclosure comprises isocitrate lyase from *E. coli*, such that the microorganism comprises a nucleotide sequence set forth in SEQ ID NO: 11, which encodes the amino acid sequence set forth in SEQ ID NO: 12. In some embodiments A microorganism of the disclosure may comprise an enzyme that converts glyoxylate to glycolate (reaction 8 of FIG. 1). This enzyme may be a glycerate dehydrogenase [1.1.1.29], a glyoxylate reductase [1.1.1.26/79], or a glycolate dehydrogenase [1.1.99.14]. In some embodiments, the enzyme that converts glyoxylate to glycolate is an endogenous enzyme. In some embodiments, the enzyme that converts glyoxylate to glycolate is overexpressed.

A microorganism of the disclosure may comprise an enzyme that converts glycolate to glycolaldehyde (reaction 9 of FIG. 1). This enzyme may be a glycolaldehyde dehydrogenase [1.2.1.21], a lactaldehyde dehydrogenase [1.2.1.22], a succinate-semialdehyde dehydrogenase [1.2.1.24], a 2,5-dioxovalerate dehydrogenase [1.2.1.26], an aldehyde dehydrogenase [1.2.1.3/4/5], a betaine-aldehyde dehydrogenase [1.2.1.8], or an aldehyde ferredoxin oxidoreductase [1.2.7.5]. In some embodiments, the enzyme that converts glycolate to glycolaldehyde is an endogenous enzyme. In other embodiments, the enzyme that converts glycolate to glycolaldehyde is a heterologous enzyme. For example, in some embodiments, a microorganism of the disclosure comprises a gamma-aminobutyraldehyde dehydrogenase from E. coli, such that the microorganism comprises a nucleotide sequence set forth in SEQ ID NO: 49, which encodes the amino acid sequence set forth in SEQ ID NO: 50. In some embodiments, a microorganism of the disclosure comprises an aldehyde dehydrogenase from E. coli, such that the microorganism comprises a nucleotide sequence set forth in SEQ ID NO: 51, which encodes the amino acid sequence set forth in SEQ ID NO: 52. In some embodiments, a microorganism of the disclosure comprises an NADP-dependent succinate-semialdehyde dehydrogenase I from E. coli, such that the microorganism comprises a nucleotide sequence set forth in SEQ ID NO: 53, which encodes the amino acid sequence set forth in SEQ ID NO: 54. In some embodiments, a microorganism of the disclosure comprises a lactaldehyde dehydrogenase/glycolaldehyde dehydrogenase from G. oxydans, such that the microorganism comprises a nucleotide sequence set forth in SEQ ID NO: 55, which encodes the amino acid sequence set forth in SEQ ID NO: 56. In some embodiments, a microorganism of the disclosure comprises an aldehyde dehydrogenase A from P. fluorescens, such that the microorganism comprises a nucleotide sequence set forth in SEQ ID NO: 57 or SEQ ID NO: 59, which encodes the amino acid sequence set forth in SEQ ID NO: 58 or SEQ ID NO: 60, respectively. Additional non-limiting examples of enzymes that convert glycolate to glycolaldehyde can be found in GenBank Accession Nos. WP_003202098, WP_003182567, ACT39044, ACT39074, WP_041112005, and ACT40170. In some embodiments, the enzyme that converts glycolate to glycolaldehyde is overexpressed.

A microorganism of the disclosure may comprise an enzyme that converts glycolaldehyde to ethylene glycol (reaction 10 of FIG. 1). This enzyme may be a lactaldehyde reductase [1.1.1.77], an alcohol dehydrogenase [1.1.1.1], an alcohol dehydrogenase (NADP+) [1.1.1.2], a glycerol dehydrogenase [1.1.1.72], a glycerol-3-phosphate dehydrogenase [1.1.1.8], or an aldehyde reductase [1.1.1.21]. In some embodiments, the enzyme that converts glycolaldehyde to ethylene glycol is an endogenous enzyme. In some embodiments, the endogenous enzyme that converts glycolaldehyde to ethylene glycol is overexpressed. In other embodiments, the enzyme that converts glycolaldehyde to ethylene glycol is a heterologous enzyme. In some embodiments, a microorganism of the disclosure comprises a lactaldehyde reductase from C. saccharoperbutylacetonicum, such that the microorganism comprises a nucleotide sequence set forth in SEQ ID NO: 61, which encodes the amino acid sequence set forth in SEQ ID NO: 62. In some embodiments, a microorganism of the disclosure comprises a lactaldehyde reductase from C. ljungdahlii, such that the microorganism comprises a nucleotide sequence set forth in SEQ ID NO: 63, which encodes the amino acid sequence set forth in SEQ ID NO: 64. In some embodiments, a microorganism of the disclosure comprises a lactaldehyde reductase from E. coli, such that the microorganism comprises a nucleotide sequence set forth in SEQ ID NO: 65, which encodes the amino acid sequence set forth in SEQ ID NO: 66. In some embodiments, a microorganism of the disclosure comprises a lactaldehyde reductase from C. beijerinckii, such that the microorganism comprises a nucleotide sequence set forth in SEQ ID NO: 67, which encodes the amino acid sequence set forth in SEQ ID NO: 68. In some embodiments, the heterologous enzyme that converts glycolaldehyde to ethylene glycol is overexpressed.

A microorganism of the disclosure may comprise an enzyme that converts pyruvate to malate (reaction 11 of FIG. 1). This enzyme may be a malate dehydrogenase [1.1.1.37], a malate dehydrogenase (oxaloacetate-decarboxylating) [1.1.1.38], a malate dehydrogenase (decarboxylating) [1.1.1.39], a malate dehydrogenase (oxaloacetate-decarboxylating) (NADP+) [1.1.1.40], a malate dehydrogenase (NADP+) [1.1.1.82], a D-malate dehydrogenase (decarboxylating) [1.1.1.83], a dimethylmalate dehydrogenase [1.1.1.84], a 3-isopropylmalate dehydrogenase [1.1.1.85], a malate dehydrogenase [NAD(P)+] [1.1.1.299], or a malate dehydrogenase (quinone) [1.1.5.4]. In some embodiments, the enzyme that converts pyruvate to malate is an endogenous enzyme. In other embodiments, the enzyme that converts pyruvate to malate is a heterologous enzyme. For example, in some embodiments, a microorganism of the disclosure comprises a malate dehydrogenase from C. autoethanogenum, such that the microorganism comprises a nucleotide sequence set forth in SEQ ID NO: 23, which encodes the amino acid sequence set forth in SEQ ID NO: 24. In some embodiments, a microorganism of the disclosure comprises an NAD-dependent malic enzyme from C. autoethanogenum, such that the microorganism comprises a nucleotide sequence set forth in SEQ ID NO: 25, which encodes the amino acid sequence set forth in SEQ ID NO: 26.

A microorganism of the disclosure may comprise an enzyme that converts malate to glyoxylate (reaction 12 of FIG. 1). This enzyme may be a malate synthase [2.3.3.9] or an isocitrate lyase [4.1.3.1]. In some embodiments, the enzyme that converts malate to glyoxylate is a heterologous enzyme. For example, in some embodiments, a microorganism of the disclosure comprises a malate synthase G from Sporosarcina sp., such that the microorganism comprises a nucleotide sequence set forth in SEQ ID NO: 27 or SEQ ID NO: 33, which encodes the amino acid sequence set forth in SEQ ID NO: 28 or SEQ ID NO: 34, respectively. In some embodiments, a microorganism of the disclosure comprises a malate synthase G from Bacillus sp., such that the microorganism comprises a nucleotide sequence set forth in SEQ ID NO: 29 or SEQ ID NO: 35, which encodes the amino acid sequence set forth in SEQ ID NO: 30 or SEQ ID NO: 36, respectively. In some embodiments, a microorganism of the disclosure comprises a malate synthase from S. coelicolor, such that the microorganism comprises a nucleotide sequence set forth in SEQ ID NO: 31, which encodes the amino acid sequence set forth in SEQ ID NO: 32. In some embodiments, a microorganism of the disclosure comprises a malate synthase G from *B. infantis*, such that the microorganism comprises a nucleotide sequence set forth in SEQ ID NO: 37, which encodes the amino acid sequence set forth in SEQ ID NO: 38. In some embodiments, a microorganism of the disclosure comprises a malate synthase from *C. cochlearium*, such that the microorganism comprises a nucleotide sequence set forth in SEQ ID NO: 39, which encodes the amino acid sequence set forth in SEQ ID NO: 40. In some embodiments, a microorganism of the disclosure comprises a malate synthase G from *B. megaterium*, such that the microorganism comprises a nucleotide sequence set forth in SEQ ID NO: 41, which encodes the amino acid sequence set forth in SEQ ID NO: 42. In some embodiments, a microorganism of the disclosure comprises a malate synthase from *Paenibacillus* sp., such that the microorganism comprises a nucleotide sequence set forth in SEQ ID NO: 43, which encodes the amino acid sequence set forth in SEQ ID NO: 44. In some embodiments, a microorganism of the disclosure comprises a malate synthase from *Lysinibacillus* sp., such that the microorganism comprises a nucleotide sequence set forth in SEQ ID NO: 45, which encodes the amino acid sequence set forth in SEQ ID NO: 46. In some embodiments, a microorganism of the disclosure comprises a malate synthase from *B. cereus*, such that the microorganism comprises a nucleotide sequence set forth in SEQ ID NO: 47, which encodes the amino acid sequence set forth in SEQ ID NO: 48.

A microorganism of the disclosure may comprise an enzyme that converts pyruvate to phosphoenolpyruvate (reaction 13 of FIG. 1). This enzyme may be a pyruvate kinase [2.7.1.40], a pyruvate, phosphate dikinase [2.7.9.1], or a pyruvate, water dikinase [2.7.9.2]. In some embodiments, the enzyme that converts pyruvate to phosphoenolpyruvate is an endogenous enzyme.

A microorganism of the disclosure may comprise an enzyme that converts phosphoenolpyruvate to 2-phospho-D-glycerate (reaction 14 of FIG. 1). This enzyme may be a phosphopyruvate hydratase [4.2.1.11]. In some embodiments, the enzyme that converts phosphoenolpyruvate to 2-phospho-D-glycerate is an endogenous enzyme.

A microorganism of the disclosure may comprise an enzyme that converts 2-phospho-D-glycerate to 3-phospho-D-glycerate (reaction 15 of FIG. 1). This enzyme may be a phosphoglycerate mutase [5.4.2.11/12]. In some embodiments, the enzyme that converts 2-phospho-D-glycerate to 3-phospho-D-glycerate is an endogenous enzyme.

A microorganism of the disclosure may comprise an enzyme that converts 3-phospho-D-glycerate to 3-phosphonooxypyruvate (reaction 16 of FIG. 1). This enzyme may be a phosphoglycerate dehydrogenase [1.1.1.95]. In some embodiments, the enzyme that converts 3-phospho-D-glycerate to 3-phosphonooxypyruvate is an endogenous enzyme.

A microorganism of the disclosure may comprise an enzyme that converts 3-phosphonooxypyruvate to 3-phospho-L-serine (reaction 17 of FIG. 1). This enzyme may be a phosphoserine transaminase [2.6.1.52]. In some embodiments, the enzyme that converts 3-phosphonooxypyruvate to 3-phospho-L-serine is an endogenous enzyme.

A microorganism of the disclosure may comprise an enzyme that converts 3-phospho-L-serine to serine (reaction 18 of FIG. 1). This enzyme may be a phosphoserine phosphatase [3.1.3.3]. In some embodiments, the enzyme that converts 3-phospho-L-serine to serine is an endogenous enzyme.

A microorganism of the disclosure may comprise an enzyme that converts serine to glycine (reaction 19 of FIG. 1). This enzyme may be a glycine hydroxymethyltransferase [2.1.2.1]. In some embodiments, the enzyme that converts serine to glycine is an endogenous enzyme. In some embodiments, the enzyme that converts serine to glycine is overexpressed.

A microorganism of the disclosure may comprise an enzyme that converts glycine to glyoxylate (reaction 20 of FIG. 1). This enzyme may be an alanine-glyoxylate aminotransferase/transaminase [2.6.1.44], a serine-glyoxylate aminotransferase/transaminase [2.6.1.45], a serine-pyruvate aminotransferase/transaminase [2.6.1.51], a glycine-oxaloacetate aminotransferase/transaminase [2.6.1.35], a glycine transaminase [2.6.1.4], a glycine dehydrogenase [1.4.1.10], an alanine dehydrogenase [1.4.1.1], or a glycine dehydrogenase [1.4.2.1]. In some embodiments, the enzyme that converts glycine to glyoxylate is an endogenous enzyme. In other embodiments, the enzyme that converts glycine to glyoxylate is a heterologous enzyme. For example, in some embodiments, a microorganism of the disclosure comprises serine-glyoxylate aminotransferase from *H. methylovorum*, such that the microorganism comprises a nucleotide sequence set forth in SEQ ID NO: 13, which encodes the amino acid sequence set forth in SEQ ID NO: 14. In some embodiments, a microorganism of the disclosure comprises alanine-glyoxylate aminotransferase from *S. thiotaurini*, such that the microorganism comprises a nucleotide sequence set forth in SEQ ID NO: 15, which encodes the amino acid sequence set forth in SEQ ID NO: 16. In some embodiments, a microorganism of the disclosure comprises alanine-glyoxylate aminotransferase from *T. tepidarius*, such that the microorganism comprises a nucleotide sequence set forth in SEQ ID NO: 17, which encodes the amino acid sequence set forth in SEQ ID NO: 18. In some embodiments, a microorganism of the disclosure comprises a Class V aminotransferase from *C. acidurici*, such that the microorganism comprises a nucleotide sequence set forth in SEQ ID NO: 19, which encodes the amino acid sequence set forth in SEQ ID NO: 20. In some embodiments, a microorganism of the disclosure comprises a serine-pyruvate aminotransferase from *T. maritima*, such that the microorganism comprises a nucleotide sequence set forth in SEQ ID NO: 21, which encodes the amino acid sequence set forth in SEQ ID NO: 22. In some embodiments, the enzyme that converts glycine to glyoxylate is overexpressed.

A microorganism of the disclosure may comprise an enzyme that converts serine to hydroxypyruvate (reaction 21 of FIG. 1). This enzyme may be a serine-pyruvate transaminase [2.6.1.51], a serine-glyoxylate transaminase [2.6.1.45], an alanine dehydrogenase [1.4.1.1], an L-amino-acid dehydrogenase [1.4.1.5], a serine 2-dehydrogenase [1.4.1.7], an alanine transaminase [2.6.1.2], a glutamine-pyruvate transaminase [2.6.1.15], a D-amino-acid transaminase [2.6.1.21], an alanine-glyoxylate transaminase [2.6.1.44], or a serine-pyruvate transaminase [2.6.1.51]. In some embodiments, the enzyme that converts serine to hydroxypyruvate is an endogenous enzyme. In other embodiments, the enzyme that converts serine to hydroxypyruvate is a heterologous enzyme. Non-limiting examples of enzymes capable of converting serine to hydroxypyruvate can be found in GenBank Accession Nos. WP_009989311 and NP_511062.1. In some embodiments, the enzyme that converts serine to hydroxypyruvate is overexpressed.

A microorganism of the disclosure may comprise an enzyme that converts hydroxypyruvate to glycolaldehyde (reaction 22 of FIG. 1). This enzyme may be a hydroxypyruvate decarboxylase [4.1.1.40] or a pyruvate decarboxylase [4.1.1.1]. This enzyme may also be any other decarboxylase [4.1.1.-]. In some embodiments, the enzyme that converts hydroxypyruvate to glycolaldehyde is a heterologous enzyme. Non-limiting examples of enzymes capable of converting hydroxypyruvate to glycolaldehyde can be found in GenBank Accession Nos. CCG28866, SVF98953, PA0096, CAA54522, KRU13460, and KLA26356.

A microorganism of the disclosure may comprise an enzyme that converts D-glycerate to hydroxypyruvate (reaction 23 of FIG. 1). This enzyme may be a glyoxylate reductase [EC 1.1.1.26], a glycerate dehydrogenase [EC 1.1.1.29], or a hydroxypyruvate reductase [EC 1.1.1.81]. In some embodiments, the enzyme that converts D-glycerate to hydroxypyruvate is a heterologous enzyme. Non-limiting examples of enzymes capable of converting D-glycerate to hydroxypyruvate can be found in GenBank Accession Nos. SUK16841, RPK22618, KPA02240, AGW90762, CAC11987, Q9CA90, and Q9UBQ7.

A microorganism of the disclosure may comprise a complex of enzymes that converts 5,10-methylenetetrahydrofolate to glycine (reaction 24 of FIG. 1). 5,10-methylenetetrahydrofolate is a cofactor in the reductive branch of the Wood-Ljungdahl pathway and acts as a scaffold in the production of acetyl-CoA. This complex may be a glycine cleavage system comprising a glycine dehydrogenase [1.4.4.2], a dihydrolipoyl dehydrogenase [1.8.1.4], and an aminomethyltransferase (glycine synthase) [2.1.2.10]. In some embodiments, the enzymes of the complex that converts 5,10-methylenetetrahydrofolate to glycine are endogenous enzymes. In some embodiments, the enzymes of the glycine cleavage system are overexpressed.

A microorganism of the disclosure may comprise an enzyme that converts phosphoenolpyruvate to oxaloacetate (reaction 25 of FIG. 1). This enzyme may be a phosphoenolpyruvate carboxykinase (ATP) [4.1.1.49] or (GTP) [4.1.1.32]. In some embodiments, the enzyme that converts phosphoenolpyruvate to oxaloacetate is an endogenous enzyme. In other embodiments, the enzyme that converts phosphoenolpyruvate to oxaloacetate is a heterologous enzyme. In some embodiments, the enzyme that converts phosphoenolpyruvate to oxaloacetate is overexpressed.

In some embodiments, a microorganism comprising an enzyme that converts acetyl-CoA to pyruvate (reaction 1 of FIG. 1), an enzyme that converts pyruvate to oxaloacetate (reaction 2 of FIG. 1), an enzyme that converts oxaloacetate to citrate (reaction 5 of FIG. 1), an enzyme that converts citrate to aconitate and aconitate to iso-citrate (reactions 6 of FIG. 1), an enzyme that converts isocitrate to glyoxylate (reaction 7 of FIG. 1), an enzyme that converts glyoxylate to glycolate (reaction 8 of FIG. 1), an enzyme that converts glycolate to glycolaldehyde (reaction 9 of FIG. 1), and an enzyme that converts glycolaldehyde to ethylene glycol (reaction 10 of FIG. 1) produces ethylene glycol. In a non-limiting example, the enzyme that converts oxaloacetate to citrate may be a citrate synthase from *B. subtilis* (SEQ ID NOs: 1-2). In a non-limiting example, the enzyme that converts iso-citrate to glyoxylate may be an isocitrate lyase from *E. coli* (SEQ ID NOs: 11-12). In a non-limiting example, the enzyme that converts glycolate to glycolaldehyde may be a glycolaldehyde dehydrogenase from *G. oxydans* (SEQ ID NOs: 55-56) or an aldehyde dehydrogenase from *P. fluorescens* (SEQ ID NOs: 57-58). One or more of the enzymes catalyzing reactions 2, 5, 6, 8, 9, and 10, as shown in FIG. 1, may be overexpressed. See, e.g., Example 1 and FIG. 3B.

In some embodiments, a microorganism comprising an enzyme that converts acetyl-CoA to pyruvate (reaction 1 of FIG. 1), an enzyme that converts pyruvate to phosphoenolpyruvate (reaction 13 of FIG. 1), an enzyme that converts phosphoenolpyruvate to 2-phospho-D-glycerate (reaction 14 of FIG. 1), an enzyme that converts 2-phospho-D-glycerate to 3-phospho-D-glycerate (reaction 15 of FIG. 1), an enzyme that converts 3-phospho-D-glycerate to 3-phosphonooxypyruvate (reaction 16 of FIG. 1), an enzyme that converts 3-phosphonooxypyruvate to 3-phospho-L-serine (reaction 17 of FIG. 1), an enzyme that converts 3-phospho-L-serine to serine (reaction 18 of FIG. 1), an enzyme that converts serine to glycine (reaction 19 of FIG. 1), an enzyme that converts glycine to glyoxylate (reaction 20 of FIG. 1), an enzyme that converts glyoxylate to glycolate (reaction 8 of FIG. 1), an enzyme that converts glycolate to glycolaldehyde (reaction 9 of FIG. 1), and an enzyme that converts glycolaldehyde to ethylene glycol (reaction 10 of FIG. 1) produces ethylene glycol. In a non-limiting example, the enzyme that converts glycine to glyoxylate may be an alanine-glyoxylate aminotransferase from *S. thiotaurini* (SEQ ID NOs: 15-16) or a class V aminotransferase from *C. acidurici* (SEQ ID NOs: 19-20). In a non-limiting example, the enzyme that converts glycolate to glycolaldehyde may be a glycolaldehyde dehydrogenase from *G. oxydans* (SEQ ID NOs: 55-56) or an aldehyde dehydrogenase from *P. fluorescens* (SEQ ID NOs: 57-58). One of more of the enzymes catalyzing the reactions of steps 19, 20, 8, 9, and 10, as shown in FIG. 1, may be overexpressed. See, e.g., Examples 2-4 and FIGS. 4B, 5B, and 6B.

In some embodiments, a microorganism comprising an enzyme that converts acetyl-CoA to pyruvate (reaction 1 of FIG. 1), an enzyme that converts pyruvate to oxaloacetate (reaction 2 of FIG. 1), an enzyme that converts oxaloacetate to citryl-CoA (reaction 3 of FIG. 1), an enzyme that converts citryl-CoA to citrate (reaction 4 of FIG. 1), an enzyme that converts citrate to aconitate and aconitate to iso-citrate (reactions 6 of FIG. 1), an enzyme that converts isocitrate to glyoxylate (reaction 7 of FIG. 1), an enzyme that converts glyoxylate to glycolate (reaction 8 of FIG. 1), an enzyme that converts glycolate to glycolaldehyde (reaction 9 of FIG. 1), and an enzyme that converts glycolaldehyde to ethylene glycol (reaction 10 of FIG. 1) produces ethylene glycol. In a non-limiting example, the enzyme that converts iso-citrate to glyoxylate may be an isocitrate lyase from *E. coli* (SEQ ID NOs: 11-12). In a non-limiting example, the enzyme that converts iso-citrate to glyoxylate may be an isocitrate lyase from *E. coli* (SEQ ID NOs: 11-12). In a non-limiting example, the enzyme that converts glycolate to glycolaldehyde may be a glycolaldehyde dehydrogenase from *G. oxydans* (SEQ ID NOs: 55-56) or an aldehyde dehydrogenase from *P. fluorescens* (SEQ ID NOs: 57-58). One or more of the enzymes catalyzing reactions 2, 6, 8, 9, and 10, as shown in FIG. 1, may be overexpressed.

In some embodiments, a microorganism comprising an enzyme that converts acetyl-CoA to pyruvate (reaction 1 of FIG. 1), an enzyme that converts pyruvate to malate (reaction 11 of FIG. 1), an enzyme that converts malate to glyoxylate (reaction 12 of FIG. 1), an enzyme that converts glyoxylate to glycolate (reaction 8 of FIG. 1), an enzyme that converts glycolate to glycolaldehyde (reaction 9 of FIG. 1), and an enzyme that converts glycolaldehyde to ethylene glycol (reaction 10 of FIG. 1) produces ethylene glycol. In a non-limiting example, the enzyme that converts glycolate to glycolaldehyde may be a glycolaldehyde dehydrogenase from *G. oxydans* (SEQ ID NOs: 55-56) or an aldehyde dehydrogenase from *P. fluorescens* (SEQ ID NOs: 57-58).

One of more of the enzymes catalyzing the reactions of steps 8, 9, and 10, as shown in FIG. 1, may be overexpressed.

In some embodiments, a microorganism comprising a complex of enzymes that converts 5,10-methylenetetrahydrofolate to glycine (reaction 24 of FIG. 1), an enzyme that converts glycine to glyoxylate (reaction 20 of FIG. 1), an enzyme that converts glyoxylate to glycolate (reaction 8 of FIG. 1), an enzyme that converts glycolate to glycolaldehyde (reaction 9 of FIG. 1), and an enzyme that converts glycolaldehyde to ethylene glycol (reaction 10 of FIG. 1) produces ethylene glycol. In a non-limiting example, the enzyme that converts glycine to glyoxylate may be an alanine-glyoxylate aminotransferase from S. thiotaurini (SEQ ID NOs: 15-16) or a class V aminotransferase from C. acidurici (SEQ ID NOs: 19-20). In a non-limiting example, the enzyme that converts glycolate to glycolaldehyde may be a glycolaldehyde dehydrogenase from G. oxydans (SEQ ID NOs: 55-56) or an aldehyde dehydrogenase from P. fluorescens (SEQ ID NOs: 57-58). One or more of the enzymes catalyzing the reactions of steps 8, 9, 10, 20, and 24 may be overexpressed.

In some embodiments, a microorganism comprising an enzyme that converts acetyl-CoA to pyruvate (reaction 1 of FIG. 1), an enzyme that converts pyruvate to phosphoenolpyruvate (reaction 13 of FIG. 1), an enzyme that converts phosphoenolpyruvate to oxaloacetate (reaction 25 of FIG. 1), an enzyme that converts oxaloacetate to citryl-CoA (reaction 3 of FIG. 1), an enzyme that converts citryl-CoA to citrate (reaction 4 of FIG. 1), an enzyme that converts citrate to aconitate and aconitate to iso-citrate (reactions 6 of FIG. 1), an enzyme that converts isocitrate to glyoxylate (reaction 7 of FIG. 1), an enzyme that converts glyoxylate to glycolate (reaction 8 of FIG. 1), an enzyme that converts glycolate to glycolaldehyde (reaction 9 of FIG. 1), and an enzyme that converts glycolaldehyde to ethylene glycol (reaction 10 of FIG. 1) produces ethylene glycol. In a non-limiting example, the enzyme that converts iso-citrate to glyoxylate may be an isocitrate lyase from E. coli (SEQ ID NOs: 11-12). In a non-limiting example, the enzyme that converts glycolate to glycolaldehyde may be a glycolaldehyde dehydrogenase from G. oxydans (SEQ ID NOs: 55-56) or an aldehyde dehydrogenase from P. fluorescens (SEQ ID NOs: 57-58). One or more of the enzymes catalyzing reactions 2, 6, 8, 9, 10, and 25, as shown in FIG. 1, may be overexpressed.

In some embodiments, a microorganism comprising an enzyme that converts acetyl-CoA to pyruvate (reaction 1 of FIG. 1), an enzyme that converts pyruvate to phosphoenolpyruvate (reaction 13 of FIG. 1), an enzyme that converts phosphoenolpyruvate to oxaloacetate (reaction 25 of FIG. 1), an enzyme that converts oxaloacetate to citrate (reaction 5 of FIG. 1), an enzyme that converts citrate to aconitate and aconitate to iso-citrate (reactions 6 of FIG. 1), an enzyme that converts isocitrate to glyoxylate (reaction 7 of FIG. 1), an enzyme that converts glyoxylate to glycolate (reaction 8 of FIG. 1), an enzyme that converts glycolate to glycolaldehyde (reaction 9 of FIG. 1), and an enzyme that converts glycolaldehyde to ethylene glycol (reaction 10 of FIG. 1) produces ethylene glycol. In a non-limiting example, the enzyme that converts oxaloacetate to citrate may be a citrate synthase from B. subtilis (SEQ ID NOs: 1-2). In a non-limiting example, the enzyme that converts iso-citrate to glyoxylate may be an isocitrate lyase from E. coli (SEQ ID NOs: 11-12). In a non-limiting example, the enzyme that converts glycolate to glycolaldehyde may be a glycolaldehyde dehydrogenase from G. oxydans (SEQ ID NOs: 55-56) or an aldehyde dehydrogenase from P. fluorescens (SEQ ID NOs: 57-58). One or more of the enzymes catalyzing reactions 5, 6, 8, 9, 10, and 25, as shown in FIG. 1, may be overexpressed.

In some embodiments, a microorganism comprising an enzyme that converts acetyl-CoA to pyruvate (reaction 1 of FIG. 1), an enzyme that converts pyruvate to phosphoenolpyruvate (reaction 13 of FIG. 1), an enzyme that converts phosphoenolpyruvate to 2-phospho-D-glycerate (reaction 14 of FIG. 1), an enzyme that converts 2-phospho-D-glycerate to 3-phospho-D-glycerate (reaction 15 of FIG. 1), an enzyme that converts 3-phospho-D-glycerate to 3-phosphonooxypyruvate (reaction 16 of FIG. 1), an enzyme that converts 3-phosphonooxypyruvate to 3-phospho-L-serine (reaction 17 of FIG. 1), an enzyme that converts 3-phospho-L-serine to serine (reaction 18 of FIG. 1), comprise an enzyme that converts serine to hydroxypyruvate (reaction 21 of FIG. 1), an enzyme that converts hydroxypyruvate to glycolaldehyde (reaction 22 of FIG. 1), and an enzyme that converts glycolaldehyde to ethylene glycol (reaction 10 of FIG. 1) produces ethylene glycol. The enzyme catalyzing the conversion of glycolaldehyde to ethylene glycol may be overexpressed.

In some embodiments, a microorganism comprising an enzyme that converts D-glycerate to hydroxypyruvate (reaction 23 of FIG. 1), an enzyme that converts hydroxypyruvate to glycolaldehyde (reaction 22 of FIG. 1), and an enzyme that converts glycolaldehyde to ethylene glycol (reaction 10 of FIG. 1) produces ethylene glycol. The enzyme catalyzing the conversion of glycolaldehyde to ethylene glycol may be overexpressed.

The enzymes of the disclosure may be codon optimized for expression in the microorganism of the disclosure. "Codon optimization" refers to the mutation of a nucleic acid, such as a gene, for optimized or improved translation of the nucleic acid in a particular strain or species. Codon optimization may result in faster translation rates or higher translation accuracy. In a preferred embodiment, the genes of the disclosure are codon optimized for expression in the microorganism of the disclosure. Although codon optimization refers to the underlying genetic sequence, codon optimization often results in improved translation and, thus, improved enzyme expression. Accordingly, the enzymes of the disclosure may also be described as being codon optimized.

One or more of the enzymes of the disclosure may be overexpressed. "Overexpressed" refers to an increase in expression of a nucleic acid or protein in the microorganism of the disclosure compared to the wild-type or parental microorganism from which the microorganism of the disclosure is derived. Overexpression may be achieved by any means known in the art, including modifying gene copy number, gene transcription rate, gene translation rate, or enzyme degradation rate. As described above, one or more of the enzymes catalyzing reactions 2, 5, 6, 8, 9, 10, 19, 20, 24, or 25 of FIG. 1 may be overexpressed.

The enzymes of the disclosure may comprise a disruptive mutation. A "disruptive mutation" refers to a mutation that reduces or eliminates (i.e., "disrupts") the expression or activity of a gene or enzyme. The disruptive mutation may partially inactivate, fully inactivate, or delete the gene or enzyme. The disruptive mutation may be a knockout (KO) mutation. The disruptive mutation may be any mutation that reduces, prevents, or blocks the biosynthesis of a product produced by an enzyme. The disruptive mutation may include, for example, a mutation in a gene encoding an enzyme, a mutation in a genetic regulatory element involved in the expression of a gene encoding an enzyme, the introduction of a nucleic acid which produces a protein that reduces or inhibits the activity of an enzyme, or the introduction of a nucleic acid (e.g., antisense RNA, siRNA, CRISPR) or protein which inhibits the expression of an enzyme. The disruptive mutation may be introduced using any method known in the art.

In one embodiment, the microorganism of the disclosure comprises a disruptive mutation in a gene encoding diol dehydratase.

In some embodiments, the microorganism of the disclosure comprises a disruptive mutation in isocitrate dehydrogenase [1.1.1.41]. Isocitrate dehydrogenase converts isocitrate to 2-oxoglutarate. Disruption of isocitrate dehydrogenase, such as by deleting isocitrate dehydrogenase, results in increased levels of iso-citrate.

In some embodiments, the microorganism of the disclosure comprises a disruptive mutation in glycerate dehydrogenase [1.1.1.29]. Glycerate dehydrogenase converts glyoxylate to glycolate. Disruption of glycerate dehydrogenase, such as by deleting isocitrate dehydrogenase, results in increased levels of glyoxylate.

In some embodiments, the microorganism of the disclosure comprises a disruptive mutation in glycolate dehydrogenase [1.1.99.14]. Glycolate dehydrogenase converts glyoxylate to glycolate. Disruption of glycolate dehydrogenase, such as by deleting glycolate dehydrogenase, results in increased levels of glyoxylate.

In some embodiments, the microorganism of the disclosure comprises a disruptive mutation in aldehyde ferredoxin oxidoreductase [1.2.7.5]. Aldehyde ferredoxin oxidoreductase converts glycolate to glycolaldehyde. Disruption of aldehyde ferredoxin oxidoreductase, such as by deleting aldehyde ferredoxin oxidoreductase, results in increased levels of glycolate.

In some embodiments, the microorganism of the disclosure comprises a disruptive mutation in aldehyde dehydrogenase [1.2.1.3/1.2.3.4/1.2.3.5]. Aldehyde dehydrogenase converts glycolate to glycolaldehyde. Disruption of aldehyde dehydrogenase, such as by deleting aldehyde dehydrogenase, results in increased levels of glycolate.

Introduction of a disruptive mutation results in a microorganism of the disclosure that produces no target product or substantially no target product or a reduced amount of target product compared to the parental microorganism from which the microorganism of the disclosure is derived. For example, the microorganism of the disclosure may produce no target product or at least about 1%, 3%, 5%, 10%, 20%, 30%, 40%, 50%, 60%, 70%, 80%, 90%, or 95% less target product than the parental microorganism. For example, the microorganism of the disclosure may produce less than about 0.001, 0.01, 0.10, 0.30, 0.50, or 1.0 g/L target product.

Although exemplary sequences and sources for enzymes are provided herein, the disclosure is by no means limited to these sequences and sources—it also encompasses variants. The term "variants" includes nucleic acids and proteins whose sequence varies from the sequence of a reference nucleic acid and protein, such as a sequence of a reference nucleic acid and protein disclosed in the prior art or exemplified herein. The disclosure may be practiced using variant nucleic acids or proteins that perform substantially the same function as the reference nucleic acid or protein. For example, a variant protein may perform substantially the same function or catalyze substantially the same reaction as a reference protein. A variant gene may encode the same or substantially the same protein as a reference gene. A variant promoter may have substantially the same ability to promote the expression of one or more genes as a reference promoter.

Such nucleic acids or proteins may be referred to herein as "functionally equivalent variants." By way of example, functionally equivalent variants of a nucleic acid may include allelic variants, fragments of a gene, mutated genes, polymorphisms, and the like. Homologous genes from other microorganisms are also examples of functionally equivalent variants. These include homologous genes in species such as *Clostridium acetobutylicum*, *Clostridium beijerinckii*, or *Clostridium ljungdahlii*, the details of which are publicly available on websites such as Genbank or NCBI. Functionally equivalent variants also include nucleic acids whose sequence varies as a result of codon optimization for a particular microorganism. A functionally equivalent variant of a nucleic acid will preferably have at least approximately 70%, approximately 80%, approximately 85%, approximately 90%, approximately 95%, approximately 98%, or greater nucleic acid sequence identity (percent homology) with the referenced nucleic acid. A functionally equivalent variant of a protein will preferably have at least approximately 70%, approximately 80%, approximately 85%, approximately 90%, approximately 95%, approximately 98%, or greater amino acid identity (percent homology) with the referenced protein. The functional equivalence of a variant nucleic acid or protein may be evaluated using any method known in the art.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

Nucleic acids may be delivered to a microorganism of the disclosure using any method known in the art. For example, nucleic acids may be delivered as naked nucleic acids or may be formulated with one or more agents, such as liposomes. The nucleic acids may be DNA, RNA, cDNA, or combinations thereof, as is appropriate. Restriction inhibitors may be used in certain embodiments. Additional vectors may include plasmids, viruses, bacteriophages, cosmids, and artificial chromosomes. In a preferred embodiment, nucleic acids are delivered to the microorganism of the disclosure using a plasmid. By way of example, transformation (including transduction or transfection) may be achieved by electroporation, ultrasonication, polyethylene glycol-mediated transformation, chemical or natural competence, protoplast transformation, prophage induction, or conjugation. In certain embodiments having active restriction enzyme systems, it may be necessary to methylate a nucleic acid before introduction of the nucleic acid into a microorganism.

Furthermore, nucleic acids may be designed to comprise a regulatory element, such as a promoter, to increase or otherwise control expression of a particular nucleic acid. The promoter may be a constitutive promoter or an inducible promoter. Ideally, the promoter is a Wood-Ljungdahl pathway promoter, a ferredoxin promoter, a pyruvate ferredoxin oxidoreductase promoter, an Rnf complex operon promoter, an ATP synthase operon promoter, or a phosphotransacetylase/acetate kinase operon promoter.

It should be appreciated that the disclosure may be practiced using nucleic acids whose sequence varies from the sequences specifically exemplified herein provided they perform substantially the same function. For nucleic acid sequences that encode a protein or peptide this means that the encoded protein or peptide has substantially the same function. For nucleic acid sequences that represent promoter sequences, the variant sequence will have the ability to promote expression of one or more genes. Such nucleic acids may be referred to herein as "functionally equivalent variants." By way of example, functionally equivalent variants of a nucleic acid include allelic variants, fragments of a gene, genes which include mutations (deletion, insertion, nucleotide substitutions and the like) and/or polymorphisms and the like. Homologous genes from other microorganisms may also be considered as examples of functionally equivalent variants of the sequences specifically exemplified herein.

These include homologous genes in species such as *Clostridium ljungdahlii, Chloroflexus aurantiacus, Metallosphaera* or *Sulfolobus* spp, details of which are publicly available on websites such as Genbank or NCBI. The phrase "functionally equivalent variants" should also be taken to include nucleic acids whose sequence varies as a result of codon optimisation for a particular organism. "Functionally equivalent variants" of a nucleic acid herein will preferably have at least approximately 70%, preferably approximately 80%, more preferably approximately 85%, preferably approximately 90%, preferably approximately 95% or greater nucleic acid sequence identity with the nucleic acid identified.

It should also be appreciated that the disclosure may be practiced using polypeptides whose sequence varies from the amino acid sequences specifically exemplified herein. These variants may be referred to herein as "functionally equivalent variants." A functionally equivalent variant of a protein or a peptide includes those proteins or peptides that share at least 40%, preferably 50%, preferably 60%, preferably 70%, preferably 75%, preferably 80%, preferably 85%, preferably 90%, preferably 95% or greater amino acid identity with the protein or peptide identified and has substantially the same function as the peptide or protein of interest. Such variants include within their scope fragments of a protein or peptide wherein the fragment comprises a truncated form of the polypeptide wherein deletions may be from 1 to 5, to 10, to 15, to 20, to 25 amino acids, and may extend from residue 1 through 25 at either terminus of the polypeptide, and wherein deletions may be of any length within the region; or may be at an internal location. Functionally equivalent variants of the specific polypeptides herein should also be taken to include polypeptides expressed by homologous genes in other species of bacteria, for example as exemplified in the previous paragraph.

The microorganisms of the disclosure may be prepared from a parental microorganism and one or more exogenous nucleic acids using any number of techniques known in the art for producing recombinant microorganisms. By way of example only, transformation (including transduction or transfection) may be achieved by electroporation, ultrasonication, polyethylene glycol-mediated transformation, chemical or natural competence, or conjugation. Suitable transformation techniques are described for example in, Sambrook J, Fritsch E F, Maniatis T: Molecular Cloning: A laboratory Manual, Cold Spring Harbour Laboratory Press, Cold Spring Harbour, 1989.

In certain embodiments, due to the restriction systems which are active in the microorganism to be transformed, it is necessary to methylate the nucleic acid to be introduced into the microorganism. This can be done using a variety of techniques, including those described below, and further exemplified in the Examples section herein after.

By way of example, in one embodiment, a recombinant microorganism of the disclosure is produced by a method comprises the following steps: introduction into a shuttle microorganism of (i) of an expression construct/vector as described herein and (ii) a methylation construct/vector comprising a methyltransferase gene; expression of the methyltransferase gene; isolation of one or more constructs/vectors from the shuttle microorganism; and, introduction of the one or more construct/vector into a destination microorganism.

In one embodiment, the methyltransferase gene of step B is expressed constitutively. In another embodiment, expression of the methyltransferase gene of step B is induced.

The shuttle microorganism is a microorganism, preferably a restriction negative microorganism that facilitates the methylation of the nucleic acid sequences that make up the expression construct/vector. In a particular embodiment, the shuttle microorganism is a restriction negative *E. coli, Bacillus subtilis,* or *Lactococcus lactis.*

The methylation construct/vector comprises a nucleic acid sequence encoding a methyltransferase.

Once the expression construct/vector and the methylation construct/vector are introduced into the shuttle microorganism, the methyltransferase gene present on the methylation construct/vector is induced. Induction may be by any suitable promoter system although in one particular embodiment of the disclosure, the methylation construct/vector comprises an inducible lac promoter and is induced by addition of lactose or an analogue thereof, more preferably isopropyl-β-D-thiogalactoside (IPTG). Other suitable promoters include the ara, tet, or T7 system. In a further embodiment of the disclosure, the methylation construct/vector promoter is a constitutive promoter.

In a particular embodiment, the methylation construct/vector has an origin of replication specific to the identity of the shuttle microorganism so that any genes present on the methylation construct/vector are expressed in the shuttle microorganism. Preferably, the expression construct/vector has an origin of replication specific to the identity of the destination microorganism so that any genes present on the expression construct/vector are expressed in the destination microorganism.

Expression of the methyltransferase enzyme results in methylation of the genes present on the expression construct/vector. The expression construct/vector may then be isolated from the shuttle microorganism according to any one of a number of known methods. By way of example only, the methodology described in the Examples section described hereinafter may be used to isolate the expression construct/vector.

In one particular embodiment, both construct/vector are concurrently isolated.

The expression construct/vector may be introduced into the destination microorganism using any number of known methods. However, by way of example, the methodology described in the Examples section hereinafter may be used. Since the expression construct/vector is methylated, the nucleic acid sequences present on the expression construct/vector are able to be incorporated into the destination microorganism and successfully expressed.

It is envisaged that a methyltransferase gene may be introduced into a shuttle microorganism and over-expressed. Thus, in one embodiment, the resulting methyltransferase enzyme may be collected using known methods and used in vitro to methylate an expression plasmid. The expression construct/vector may then be introduced into the destination microorganism for expression. In another embodiment, the methyltransferase gene is introduced into the genome of the shuttle microorganism followed by introduction of the expression construct/vector into the shuttle microorganism, isolation of one or more constructs/vectors from the shuttle microorganism and then introduction of the expression construct/vector into the destination microorganism.

It is envisaged that the expression construct/vector and the methylation construct/vector as defined above may be combined to provide a composition of matter. Such a composition has particular utility in circumventing restriction barrier mechanisms to produce the recombinant microorganisms of the disclosure.

In one particular embodiment, the expression construct/vector and/or the methylation construct/vector are plasmids.

Persons of ordinary skill in the art will appreciate a number of suitable methyltransferases of use in producing the microorganisms of the disclosure. However, by way of example the *Bacillus subtilis* phage ΦT1 methyltransferase and the methyltransferase described in the Examples herein after may be used. Nucleic acids encoding suitable methyltransferases will be readily appreciated having regard to the sequence of the desired methyltransferase and the genetic code.

Any number of constructs/vectors adapted to allow expression of a methyltransferase gene may be used to generate the methylation construct/vector.

In one embodiment, the substrate comprises CO. In one embodiment, the substrate comprises CO2 and CO. In another embodiment, the substrate comprises CO2 and H2. In another embodiment, the substrate comprises CO2 and CO and H2.

"Substrate" refers to a carbon and/or energy source for the microorganism of the disclosure. Often, the substrate is gaseous and comprises a C1-carbon source, for example, CO, $CO_2$, and/or $CH_4$. Preferably, the substrate comprises a C1-carbon source of CO or CO+$CO_2$. The substrate may further comprise other non-carbon components, such as $H_2$, $N_2$, or electrons. In other embodiments, however, the substrate may be a carbohydrate, such as sugar, starch, fiber, lignin, cellulose, or hemicellulose or a combination thereof. For example, the carbohydrate may be fructose, galactose, glucose, lactose, maltose, sucrose, xylose, or some combination thereof. In some embodiments, the substrate does not comprise (D)-xylose (Alkim, *Microb Cell Fact*, 14: 127, 2015). In some embodiments, the substrate does not comprise a pentose such as xylose (Pereira, *Metab Eng*, 34: 80-87, 2016). In some embodiments, the substrate may comprise both gaseous and carbohydrate substrates (mixotrophic fermentation). The substrate may further comprise other non-carbon components, such as $H_2$, $N_2$, or electrons.

The gaseous substrate generally comprises at least some amount of CO, such as about 1, 2, 5, 10, 20, 30, 40, 50, 60, 70, 80, 90, or 100 mol % CO. The gaseous substrate may comprise a range of CO, such as about 20-80, 30-70, or 40-60 mol % CO. Preferably, the gaseous substrate comprises about 40-70 mol % CO (e.g., steel mill or blast furnace gas), about 20-30 mol % CO (e.g., basic oxygen furnace gas), or about 15-45 mol % CO (e.g., syngas). In some embodiments, the gaseous substrate may comprise a relatively low amount of CO, such as about 1-10 or 1-20 mol % CO. The microorganism of the disclosure typically converts at least a portion of the CO in the gaseous substrate to a product. In some embodiments, the gaseous substrate comprises no or substantially no (<1 mol %) CO.

The gaseous substrate may comprise some amount of $H_2$. For example, the gaseous substrate may comprise about 1, 2, 5, 10, 15, 20, or 30 mol % $H_2$. In some embodiments, the gaseous substrate may comprise a relatively high amount of $H_2$, such as about 60, 70, 80, or 90 mol % $H_2$. In further embodiments, the gaseous substrate comprises no or substantially no (<1 mol %) $H_2$.

The gaseous substrate may comprise some amount of $CO_2$. For example, the gaseous substrate may comprise about 1-80 or 1-30 mol % $CO_2$. In some embodiments, the gaseous substrate may comprise less than about 20, 15, 10, or 5 mol % $CO_2$. In another embodiment, the gaseous substrate comprises no or substantially no (<1 mol %) $CO_2$.

The gaseous substrate may also be provided in alternative forms. For example, the gaseous substrate may be dissolved in a liquid or adsorbed onto a solid support.

The gaseous substrate and/or C1-carbon source may be a waste gas or an off gas obtained as a byproduct of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining, coal gasification, electric power production, carbon black production, ammonia production, methanol production, and coke manufacturing. In these embodiments, the gaseous substrate and/or C1-carbon source may be captured from the industrial process before it is emitted into the atmosphere, using any convenient method.

The gaseous substrate and/or C1-carbon source may be syngas, such as syngas obtained by gasification of coal or refinery residues, gasification of biomass or lignocellulosic material, or reforming of natural gas. In another embodiment, the syngas may be obtained from the gasification of municipal solid waste or industrial solid waste.

The substrate and/or C1-carbon source may be a waste gas obtained as a byproduct of an industrial process or from another source, such as automobile exhaust fumes, biogas, landfill gas, direct air capture, or from electrolysis. The substrate and/or C1-carbon source may be syngas generated by pyrolysis, torrefaction, or gasification. In other words, carbon in waste material may be recycled by pyrolysis, torrefaction, or gasification to generate syngas which is used as the substrate and/or C1-carbon source. The substrate and/or C1-carbon source may be a gas comprising methane.

In certain embodiments, the industrial process is selected from ferrous metal products manufacturing, such as a steel manufacturing, non-ferrous products manufacturing, petroleum refining, electric power production, carbon black production, paper and pulp manufacturing, ammonia production, methanol production, coke manufacturing, petrochemical production, carbohydrate fermentation, cement making, aerobic digestion, anaerobic digestion, catalytic processes, natural gas extraction, cellulosic fermentation, oil extraction, geological reservoirs, gas from fossil resources such as natural gas coal and oil, or any combination thereof. Examples of specific processing steps within an industrial process include catalyst regeneration, fluid catalyst cracking, and catalyst regeneration. Air separation and direct air capture are other suitable industrial processes. Specific examples in steel and ferroalloy manufacturing include blast furnace gas, basic oxygen furnace gas, coke oven gas, direct reduction of iron furnace top-gas, and residual gas from smelting iron. In these embodiments, the substrate and/or C1-carbon source may be captured from the industrial process before it is emitted into the atmosphere, using any known method.

The substrate and/or C1-carbon source may be synthesis gas known as syngas, which may be obtained from reforming, partial oxidation, or gasification processes. Examples of gasification processes include gasification of coal, gasification of refinery residues, gasification of petroleum coke, gasification of biomass, gasification of lignocellulosic material, gasification of waste wood, gasification of black liquor, gasification of municipal solid waste, gasification of municipal liquid waste, gasification of industrial solid waste, gasification of industrial liquid waste, gasification of refuse derived fuel, gasification of sewerage, gasification of sewerage sludge, gasification of sludge from wastewater treatment, gasification of biogas. Examples of reforming processes include, steam methane reforming, steam naphtha reforming, reforming of natural gas, reforming of biogas, reforming of landfill gas, naphtha reforming, and dry methane reforming. Examples of partial oxidation processes include thermal and catalytic partial oxidation processes, catalytic partial oxidation of natural gas, partial oxidation of hydrocarbons. Examples of municipal solid waste include tires, plastics, fibers, such as in shoes, apparel, and textiles. Municipal solid waste may be simply landfill-type waste. The municipal solid waste may be sorted or unsorted. Examples of biomass may include lignocellulosic material and may also include microbial biomass. Lignocellulosic material may include agriculture waste and forest waste.

The substrate and/or C1-carbon source may be a gas stream comprising methane. Such a methane containing gas may be obtained from fossil methane emission such as during fracking, wastewater treatment, livestock, agriculture, and municipal solid waste landfills. It is also envisioned that the methane may be burned to produce electricity or heat, and the C1 byproducts may be used as the substrate or carbon source.

The composition of the gaseous substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

In certain embodiments, the fermentation is performed in the absence of carbohydrate substrates, such as sugar, starch, fiber, lignin, cellulose, or hemicellulose.

In some embodiments, the overall energetics of CO and $H_2$ to ethylene glycol (MEG) are preferable to those from glucose to ethylene glycol, as shown below, wherein the more negative Gibbs free energy, ΔrG'm, values for CO and $H_2$ indicate a larger driving force towards ethylene glycol. Calculations of overall reaction delta G for the comparison of glucose vs CO as a substrate were performed using equilibrator (http://equilibrator.weizmann ac.il/), which is a standard method for evaluating the overall feasibility of a pathway or individual steps in pathways in biological systems (Flamholz, E. Noor, A. Bar-Even, R. Milo (2012) eQuilibrator—the biochemical thermodynamics calculator Nucleic Acids Res 40:D770-5; Noor, A. Bar-Even, A. Flamholz, Y. Lubling, D. Davidi, R. Milo (2012) An integrated open framework for thermodynamics of reactions that combines accuracy and coverageBioinformatics 28:2037-2044; Noor, H. S. Haraldsdottir, R. Milo, R. M. T. Fleming (2013) Consistent Estimation of Gibbs Energy Using Component Contributions PLoS Comput Biol 9(7): e1003098; Noor, A. Bar-Even, A. Flamholz, E. Reznik, W. Liebermeister, R. Milo (2014) Pathway Thermodynamics Highlights Kinetic Obstacles in Central Metabolism PLoS Comput Biol 10(2): e1003483). The calculations are as follows:

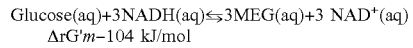
ΔrG'm−104 kJ/mol

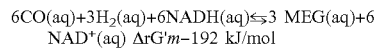
NAD⁺(aq) ΔrG'm−192 kJ/mol

Physiological Conditions:

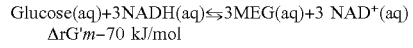
ΔrG'm−70 kJ/mol

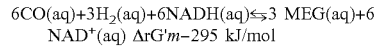
NAD⁺(aq) ΔrG'm−295 kJ/mol

In addition to ethylene glycol, glyoxylate, and/or glycolate, the microorganism of the disclosure may be cultured to produce one or more co-products products. For instance, the microorganism of the disclosure may produce or may be engineered to produce ethanol (WO 2007/117157), acetate (WO 2007/117157), 1-butanol (WO 2008/115080, WO 2012/053905, and WO 2017/066498), butyrate (WO 2008/115080), 2,3-butanediol (WO 2009/151342 and WO 2016/094334), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), terpenes, including isoprene (WO 2013/180584), fatty acids (WO 2013/191567), 2-butanol (WO 2013/185123), 1,2-propanediol (WO 2014/036152), 1-propanol (WO 2017/066498), 1-hexanol (WO 2017/066498), 1-octanol (WO 2017/066498), chorismate-derived products (WO 2016/191625), 3-hydroxybutyrate (WO 2017/066498), 1,3-butanediol (WO 2017/066498), 2-hydroxyisobutyrate or 2-hydroxyisobutyric acid (WO 2017/066498), isobutylene (WO 2017/066498), adipic acid (WO 2017/066498), 1,3-hexanediol (WO 2017/066498), 3-methyl-2-butanol (WO 2017/066498), 2-buten-1-ol (WO 2017/066498), isovalerate (WO 2017/066498), isoamyl alcohol (WO 2017/066498), and/or monoethylene glycol (WO 2019/126400) in addition to 2-phenylethanol. In some embodiments, in addition to ethylene glycol, the microorganism of the disclosure also produces ethanol, 2,3-butanediol, and/or succinate. In certain embodiments, microbial biomass itself may be considered a product. These products may be further converted to produce at least one component of diesel, jet fuel, and/or gasoline. In certain embodiments, 2-phenylethanol may be used as an ingredient in fragrances, essential oils, flavors, and soaps. Additionally, the microbial biomass may be further processed to produce a single cell protein (SCP) by any method or combination of methods known in the art. In addition to one or more target products, the microorganism of the disclosure may also produce ethanol, acetate, and/or 2,3-butanediol.

A "native product" is a product produced by a genetically unmodified microorganism. For example, ethanol, acetate, and 2,3-butanediol are native products of *Clostridium autoethanogenum, Clostridium ljungdahlii*, and *Clostridium ragsdalei*. A "non-native product" is a product that is produced by a genetically modified microorganism but is not produced by a genetically unmodified microorganism from which the genetically modified microorganism is derived. Ethylene glycol is not known to be produced by any naturally-occurring microorganism, such that it is a non-native product of all microorganisms.

"Selectivity" refers to the ratio of the production of a target product to the production of all fermentation products produced by a microorganism. The microorganism of the disclosure may be engineered to produce products at a certain selectivity or at a minimum selectivity. In one embodiment, a target product, such as ethylene glycol, accounts for at least about 5%, 10%, 15%, 20%, 30%, 50%, or 75% of all fermentation products produced by the microorganism of the disclosure. In one embodiment, ethylene glycol accounts for at least 10% of all fermentation products produced by the microorganism of the disclosure, such that the microorganism of the disclosure has a selectivity for ethylene glycol of at least 10%. In another embodiment, ethylene glycol accounts for at least 30% of all fermentation products produced by the microorganism of the disclosure, such that the microorganism of the disclosure has a selectivity for ethylene glycol of at least 30%.

At least one of the one or more fermentation products may be biomass produced by the culture. At least a portion of the microbial biomass may be converted to a single cell protein (SCP). At least a portion of the single cell protein may be utilized as a component of animal feed.

In one embodiment, the disclosure provides an animal feed comprising microbial biomass and at least one excipient, wherein the microbial biomass comprises a microorganism grown on a gaseous substrate comprising one or more of CO, CO2, and H2.

A "single cell protein" (SCP) refers to a microbial biomass that may be used in protein-rich human and/or animal feeds, often replacing conventional sources of protein supplementation such as soymeal or fishmeal. To produce a single cell protein, or other product, the process may comprise additional separation, processing, or treatments steps. For example, the method may comprise sterilizing the microbial biomass, centrifuging the microbial biomass, and/or drying the microbial biomass. In certain embodiments, the microbial biomass is dried using spray drying or paddle drying. The method may also comprise reducing the nucleic acid content of the microbial biomass using any method known in the art, since intake of a diet high in nucleic acid content may result in the accumulation of nucleic acid degradation products and/or gastrointestinal distress. The single cell protein may be suitable for feeding to animals, such as livestock or pets. In particular, the animal feed may be suitable for feeding to one or more beef cattle, dairy cattle, pigs, sheep, goats, horses, mules, donkeys, deer, buffalo/bison, llamas, alpacas, reindeer, camels, bantengs, gayals, yaks, chickens, turkeys, ducks, geese, quail, guinea fowl, squabs/pigeons, fish, shrimp, crustaceans, cats, dogs, and rodents. The composition of the animal feed may be tailored to the nutritional requirements of different animals. Furthermore, the process may comprise blending or combining the microbial biomass with one or more excipients.

"Microbial biomass" refers biological material comprising microorganism cells. For example, microbial biomass may comprise or consist of a pure or substantially pure culture of a bacterium, archaea, virus, or fungus. When initially separated from a fermentation broth, microbial biomass generally contains a large amount of water. This water may be removed or reduced by drying or processing the microbial biomass.

An "excipient" may refer to any substance that may be added to the microbial biomass to enhance or alter the form, properties, or nutritional content of the animal feed. For example, the excipient may comprise one or more of a carbohydrate, fiber, fat, protein, vitamin, mineral, water, flavour, sweetener, antioxidant, enzyme, preservative, probiotic, or antibiotic. In some embodiments, the excipient may be hay, straw, silage, grains, oils or fats, or other plant material. The excipient may be any feed ingredient identified in Chiba, Section 18: Diet Formulation and Common Feed Ingredients, Animal Nutrition Handbook, 3rd revision, pages 575-633, 2014.

A "biopolymer" refers to natural polymers produced by the cells of living organisms. In certain embodiments, the biopolymer is PHA. In certain embodiments, the biopolymer is PHB.

A "bioplastic" refers to plastic materials produced from renewable biomass sources. A bioplastic may be produced from renewable sources, such as vegetable fats and oils, corn starch, straw, woodchips, sawdust, or recycled food waste.

Herein, reference to an acid (e.g., acetic acid or 2-hydroxyisobutyric acid) should be taken to also include the corresponding salt (e.g., acetate or 2-hydroxyisobutyrate).

Typically, the culture is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and product biosynthesis phase of the culture/fermentation process.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium. Suitable media are well known in the art.

The culture/fermentation should desirably be carried out under appropriate conditions for production of ethylene glycol. If necessary, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting.

Operating a bioreactor at elevated pressures allows for an increased rate of gas mass transfer from the gas phase to the liquid phase. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure. Also, since a given gas conversion rate is in part a function of substrate retention time and achieving a desired retention time in turn dictates the required volume of a bioreactor, the use of pressurized systems can greatly reduce the volume of the bioreactor required, and consequently the capital cost of the fermentation equipment.

In certain embodiments, the fermentation is performed in the absence of light or in the presence of an amount of light insufficient to meet the energetic requirements of photosynthetic microorganisms. In certain embodiments, the microorganism of the disclosure is a non-photosynthetic microorganism.

Target products may be separated or purified from a fermentation broth using any method or combination of methods known in the art, including, for example, fractional distillation, evaporation, pervaporation, gas stripping, phase separation, and extractive fermentation, including for example, liquid-liquid extraction. In certain embodiments, target products are recovered from the fermentation broth by continuously removing a portion of the broth from the bioreactor, separating microbial cells from the broth (conveniently by filtration), and recovering one or more target products from the broth. Alcohols and/or acetone may be recovered, for example, by distillation. Acids may be recovered, for example, by adsorption on activated charcoal. Separated microbial cells are preferably returned to the bioreactor. The cell-free permeate remaining after target products have been removed is also preferably returned to the bioreactor. Additional nutrients (such as B vitamins) may be added to the cell-free permeate to replenish the medium before it is returned to the bioreactor. Purification techniques may include affinity tag purification (e.g. His, Twin-Strep, and FLAG), bead-based systems, a tip-based approach, and FPLC system for larger scale, automated purifications. Purification methods that do not rely on affinity tags (e.g. salting out, ion exchange, and size exclusion) are also disclosed.

The method of the disclosure may further comprise separating the ethylene glycol from the fermentation broth. Ethylene glycol may be separated or purified from a fermentation broth using any method or combination of methods known in the art, including, for example, distillation, simulated moving bed processes, membrane treatment, evaporation, pervaporation, gas stripping, phase separation, ion exchange, or extractive fermentation, including for example, liquid-liquid extraction. In one embodiment, ethylene glycol may be concentrated from the fermentation broth using reverse osmosis and/or pervaporation (U.S. Pat. No. 5,552,023). Water may be removed by distillation and the bottoms (containing a high proportion of ethylene glycol) may then be recovered using distillation or vacuum distillation to produce a high purity ethylene glycol stream. Alternatively, with or without concentration by reverse osmosis and/or pervaporation, ethylene glycol may be further purified by reactive distillation with an aldehyde (Atul, Chem Eng Sci, 59: 2881-2890, 2004) or azeotropic distillation using a hydrocarbon (U.S. Pat. No. 2,218,234). In another approach, ethylene glycol may be trapped on an activated carbon or polymer absorbent from aqueous solution (with or without reverse osmosis and/or pervaporation) and recovered using a low boiling organic solvent (Chinn, Recovery of Glycols, Sugars, and Related Multiple —OH Compounds from Dilute-Aqueous Solution by Regenerable Adsorption onto Activated Carbons, University of California Berkeley, 1999). Ethylene glycol can then be recovered from the organic solvent by distillation. In certain embodiments, ethylene glycol is recovered from the fermentation broth by continuously removing a portion of the broth from the bioreactor, separating microbial cells from the broth (conveniently by filtration), and recovering ethylene glycol from the broth. Co-products, such as alcohols or acids may also be separated or purified from the broth. Alcohols may be recovered, for example, by distillation. Acids may be recovered, for example, by adsorption on activated charcoal. Separated microbial cells may be returned to the bioreactor in certain embodiments. The cell-free permeate remaining after target products have been removed is also preferably returned to the bioreactor, in whole or in part. Additional nutrients (such as B vitamins) may be added to the cell-free permeate to replenish the medium before it is returned to the bioreactor.

Recovery of diols from aqueous media has been demonstrated a number of ways. Simulated moving bed (SMB) technology has been used to recover 2,3-butaendiol from an aqueous mixture of ethanol and associated oxygenates (U.S. Pat. No. 8,658,845). Reactive separation has also been demonstrated for effective diol recovery. In some embodiments, recovery of ethylene glycol is conducted by reaction of the diol-containing stream with aldehydes, fractionation and regeneration of the diol, final fractionation to recover a concentrated diol stream. See, e.g., U.S. Pat. No. 7,951,980.

The disclosure provides compositions comprising ethylene glycol produced by the microorganisms and according to the methods described herein. For example, the composition comprising ethylene glycol may be an antifreeze, preservative, dehydrating agent, or drilling fluid.

The disclosure also provides polymers comprising ethylene glycol produced by the microorganisms and according to the methods described herein. Such polymers may be, for example, homopolymers such as polyethylene glycol or copolymers such as polyethylene terephthalate. Methods for the synthesis of these polymers are well-known in the art. See, e.g., Herzberger et al., *Chem Rev.*, 116(4): 2170-2243 (2016) and Xiao et al., *Ind Eng Chem Res.* 54(22): 5862-5869 (2015).

The disclosure further provides compositions comprising polymers comprising ethylene glycol produced by the microorganisms and according to the methods described herein. For example, the composition may be a fiber, resin, film, or plastic.

One embodiment is directed to a genetically engineered microorganism capable of producing ethylene glycol or a precursor of ethylene glycol from a gaseous substrate comprising: a disruptive mutation in a gene encoding diol dehydratase.

The microorganism according to an embodiment, wherein the microorganism produces ethylene glycol or the precursor of ethylene glycol through one or more intermediates selected from the group consisting of 5,10-methylenetetrahydrofolate, oxaloacetate, citrate, malate, and glycine.

The microorganism according to an embodiment, wherein the microorganism comprises one or more of:
  a. a nucleic acid encoding a heterologous enzyme capable of converting oxaloacetate to citrate;
  b. a nucleic acid encoding a heterologous enzyme capable of converting glycine to glyoxylate;
  c. a nucleic acid encoding a heterologous enzyme capable of converting iso-citrate to glyoxylate; and
  d. a nucleic acid encoding a heterologous enzyme capable of converting glycolate to glycolaldehyde.

The microorganism according to an embodiment, wherein:
  a. the heterologous enzyme capable of converting oxaloacetate to citrate is a citrate [Si]-synthase having the EC number 2.3.3.1, an ATP citrate synthase having the EC number 2.3.3.8; or a citrate (Re)-synthase having the EC number 2.3.3.3;
  b. the heterologous enzyme capable of converting glycine to glyoxylate is an alanine-glyoxylate transaminase having the EC number 2.6.1.44, a serine-glyoxylate transaminase having the EC number 2.6.1.45, a serine-pyruvate transaminase having the EC number 2.6.1.51, a glycine-oxaloacetate transaminase having the EC number 2.6.1.35, a glycine transaminase having the EC number 2.6.1.4, a glycine dehydrogenase having the EC number 1.4.1.10, an alanine dehydrogenase having the EC number 1.4.1.1, or a glycine dehydrogenase having the EC number 1.4.2.1;
  c. the heterologous enzyme capable of converting iso-citrate to glyoxylate is an isocitrate lyase having the EC number 4.1.3.1; and/or
  d. the heterologous enzyme capable of converting glycolate to glycolaldehyde is a glycolaldehyde dehydrogenase having the EC number 1.2.1.21, a lactaldehyde dehydrogenase having the EC number 1.2.1.22, a succinate-semialdehyde dehydrogenase having the EC number 1.2.1.24, a 2,5-dioxovalerate dehydrogenase having the EC number 1.2.1.26, an aldehyde dehydrogenase having the EC number 1.2.1.3/4/5, a betaine-aldehyde dehydrogenase having he EC number 1.2.1.8, or an aldehyde ferredoxin oxidoreductase having the EC number 1.2.7.5.

The microorganism according to an embodiment, wherein one or more of the heterologous enzymes are derived from a genus selected from the group consisting of *Bacillus, Clostridium, Escherichia, Gluconobacter, Hyphomicrobium, Lysinibacillus, Paenibacillus, Pseudomonas, Sedimenticola, Sporosarcina, Streptomyces, Thermithiobacillus, Thermotoga, Cupriavidus*, and *Zea*.

The microorganism according to an embodiment, wherein one or more of the heterologous enzymes are codon-optimized for expression in the microorganism.

The microorganism according to an embodiment, wherein the microorganism further comprises one or more of an enzymes capable of converting acetyl-CoA to pyruvate; an enzyme capable of converting pyruvate to oxaloacetate; an enzyme capable of converting pyruvate to malate; an enzyme capable of converting pyruvate to phosphoenolpyruvate; an enzyme capable of converting oxaloacetate to citryl-CoA; an enzyme capable of converting citryl-CoA to citrate; an enzyme capable of converting citrate to aconitate and aconitate to iso-citrate; an enzyme capable of converting phosphoenolpyruvate to oxaloacetate; an enzyme capable of converting phosphoenolpyruvate to 2-phospho-D-glycerate; an enzyme capable of converting 2-phospho-D-glycerate to 3-phospho-D-glycerate; an enzyme capable of converting 3-phospho-D-glycerate to 3-phosphonooxypyruvate; an enzyme capable of converting 3-phosphonooxypyruvate to 3-phospho-L-serine; an enzyme capable of converting 3-phospho-L-serine to serine; an enzyme capable of converting serine to glycine; an enzyme capable of converting 5,10-methylenetetrahydrofolate to glycine; an enzyme capable of converting serine to hydroxypyruvate; an enzyme capable of converting D-glycerate to hydroxypyruvate; an enzyme capable of converting malate to glyoxylate; an enzyme capable of converting glyoxylate to glycolate; an enzyme capable of converting hydroxypyruvate to glycolaldehyde; and an enzyme capable of converting glycolaldehyde to ethylene glycol.

The microorganism according to an embodiment, wherein the microorganism overexpresses:
  a. the heterologous enzyme capable of converting oxaloacetate to citrate;
  b. the heterologous enzyme capable of converting glycine to glyoxylate; and/or
  c. the heterologous enzyme capable of converting glycolate to glycolaldehyde.

The microorganism according to an embodiment, wherein the microorganism overexpresses:
  a. the enzyme capable of converting pyruvate to oxaloacetate;
  b. the enzyme capable of converting citrate to aconitate and aconitate to iso-citrate;
  c. the enzyme capable of converting phosphoenolpyruvate to oxaloacetate;
  d. the enzyme capable of converting serine to glycine;
  e. the enzyme capable of converting 5,10-methylenetetrahydrofolate to glycine;
  f. the enzyme capable of converting glyoxylate to glycolate; and/or
  g. the enzyme capable of converting glycolaldehyde to ethylene glycol.

The microorganism according to an embodiment, wherein the microorganism further comprises a disruptive mutation in one or more of isocitrate dehydrogenase, glycerate dehydrogenase, glycolate dehydrogenase, glycerate dehydrogenase, glycolate dehydrogenase, aldehyde ferredoxin oxidoreductase, and aldehyde dehydrogenase.

The microorganism according to an embodiment, wherein the microorganism is a member of a genus selected from the group consisting of Acetobacterium, *Alkalibaculum, Blautia, Butyribacterium, Clostridium, Cupriavidus, Eubacterium, Moorella, Oxobacter, Sporomusa*, and *Thermoanaerobacter.*

The microorganism according to an embodiment, wherein the microorganism is derived from a parental microorganism selected from the group consisting of *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Cupriavidus necator, Eubacterium limosum, Moorella thermautotrophica, Moorella thermoacetica, Oxobacter pfennigii, Sporomusa ovata, Sporomusa silvacetica, Sporomusa sphaeroides*, and *Thermoanaerobacter kiuvi*.

The microorganism according to an embodiment, wherein the microorganism is derived from a parental bacterium selected from the group consisting of *Clostridium autoethanogenum*, *Clostridium ljungdahlii*, and *Clostridium ragsdalei*.

The microorganism according to an embodiment, wherein the microorganism comprises a native or heterologous Wood-Ljungdahl pathway.

The microorganism according to an embodiment, wherein the precursor of ethylene glycol is glyoxylate or glycolate.

Another embodiment is directed to a method of producing ethylene glycol or a precursor of ethylene glycol comprising culturing the microorganism of claim 1 in a nutrient medium in the presence of a gaseous substrate, whereby the microorganism produces ethylene glycol or the precursor of ethylene glycol.

The method of one embodiment, wherein the gaseous substrate comprises one or more of CO, $CO_2$, and $H_2$.

The method of one embodiment, wherein the precursor of ethylene glycol is glyoxylate or glycolate.

The method of one embodiment, further comprising separating ethylene glycol or the precursor of ethylene glycol from the nutrient medium.

The method of one embodiment, wherein the microorganism further produces one or more of ethanol, 2,3-butanediol, and succinate.

Another embodiment is directed to a method of producing a polyethylene terephthalate (PET) product from a gaseous substrate comprising 1) forming at least one PET component, wherein the at least one PET component is selected from monoethylene glycol (MEG), a terephthalic acid (PTA), or any combinations thereof; 2) processing the at least one PET component into PET; 3) polymerizing the PET to form a PET resin; and 4) processing the PET resin into a PET product.

EXAMPLES

The following examples further illustrate the disclosure but, of course, should not be construed to limit its scope in any way.

Example 1: Construction of Heterologous Expression Vector Comprising *B. subtilis* Citrate Synthase, *E. coli* Isocitrate Lyase, and *G. oxydans* Glycolaldehyde Dehydrogenase for Production of Ethylene Glycol from CO and/or $CO_2$ and $H_2$ in *C. autoethanogenum*

Figure 2A:
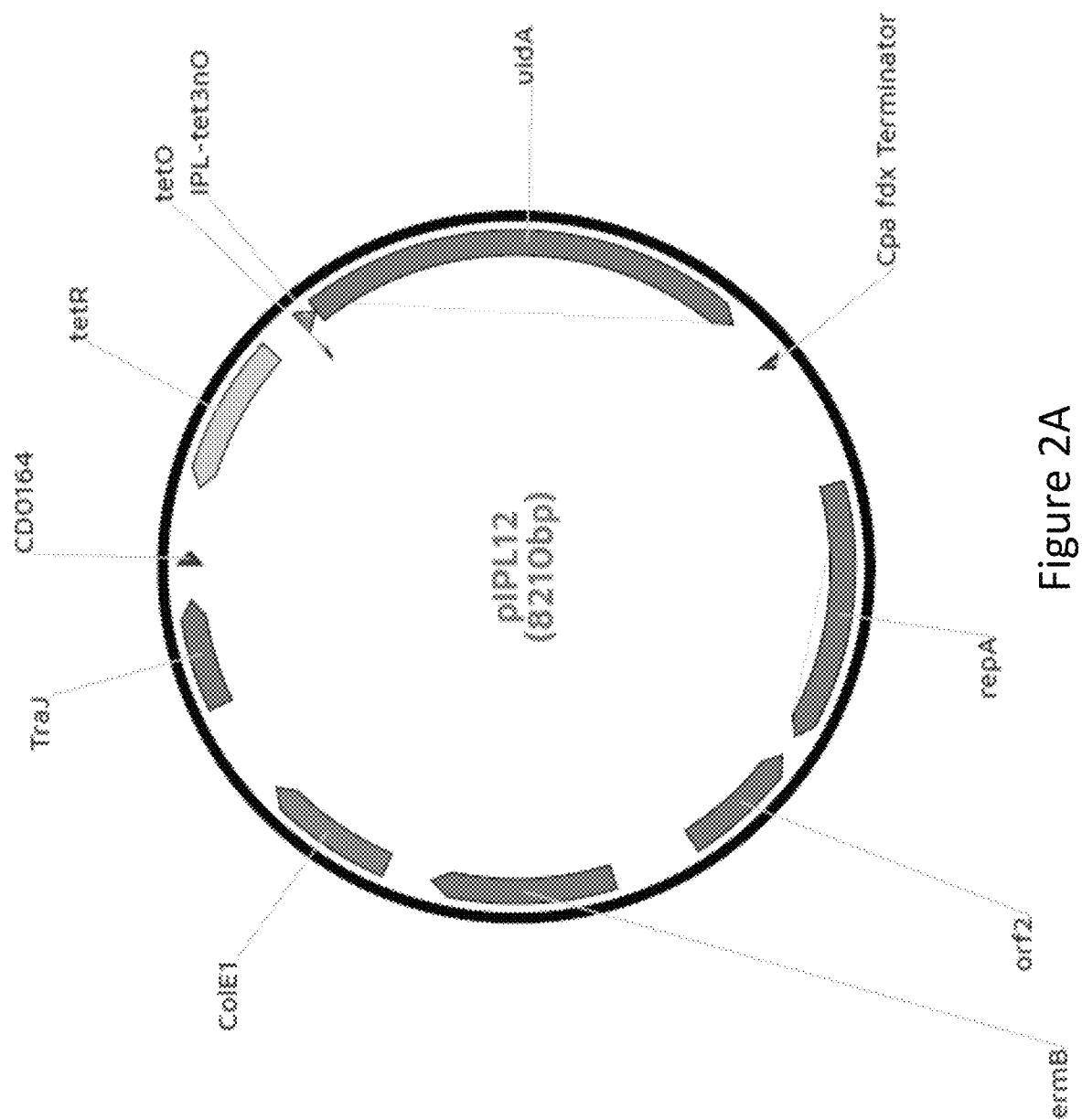
FIGS. 2A-2E are maps of plasmids used in Examples 1-4.
Figure 2B:
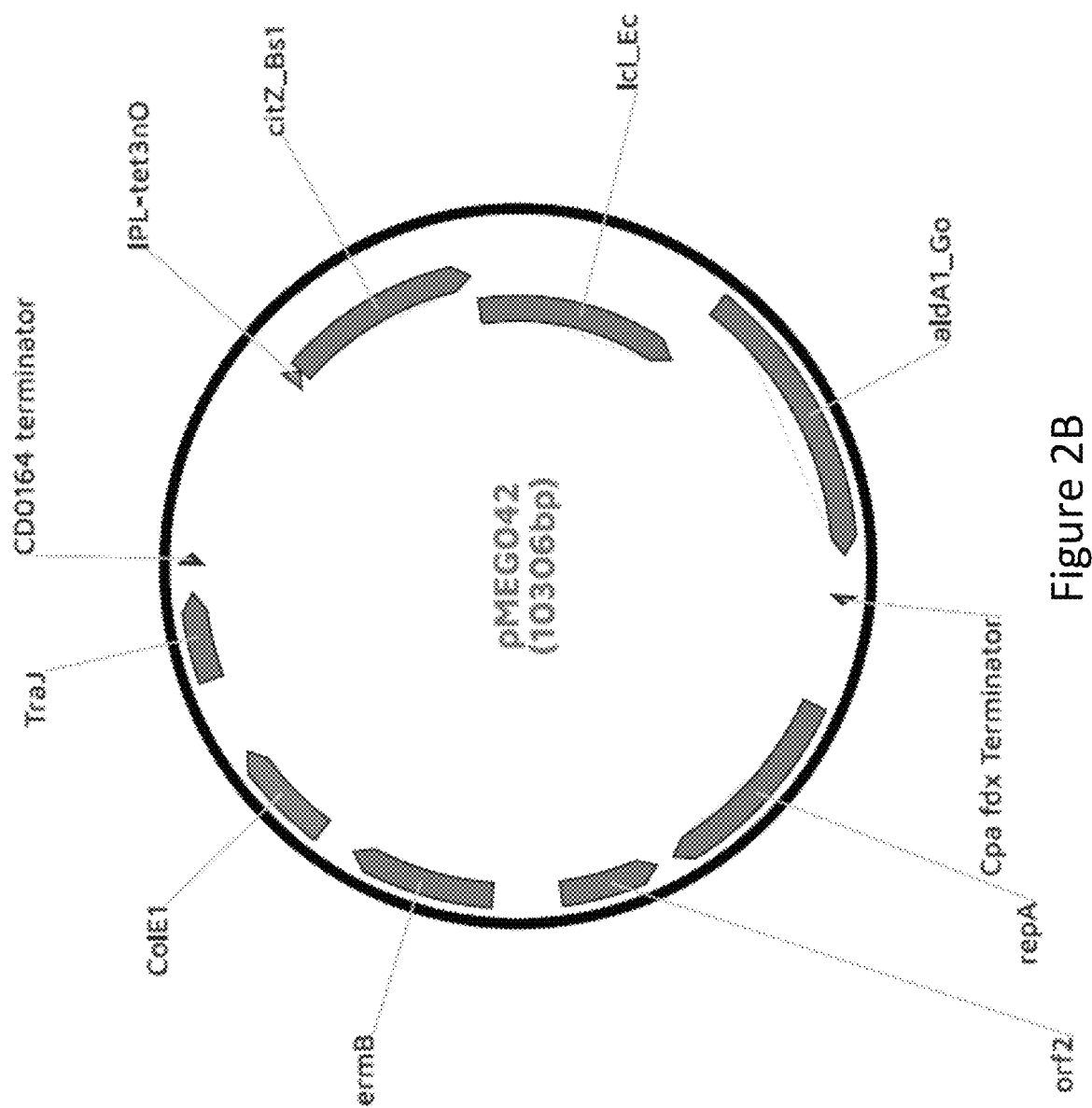

Genes coding for citrate synthase from *B. subtilis* (citZ; SEQ ID NOs: 1-2), isocitrate lyase from *E. coli* (icl; SEQ ID NOs: 11-12), and glycolaldehyde dehydrogenase from *G. oxydans* (aldA1; SEQ ID NOs: 55-56) were codon-adapted and synthesized for expression in *C. autoethanogenum*. The adapted genes were cloned into an expression shuttle vector, pIPL12, using a standard BsaI golden gate cloning kit (New England Biolabs, Ipswich, MA). pIPL12 comprises an origin of replication for both *E. coli* and *C. autoethanogenum*, enabling it to replicate and be maintained in both species; pIPL12 also functions in most Clostridia. pIPL12 further comprises 23S rRNA (adenine(2058)-N(6))-methyltransferase Erm(B) conferring erythromycin/clarithromycin resistance for positive selection, TraJ for conjugative transfer from *E. coli*, and a promoter for expression of heterologous genes. See FIG. 2A. The expression vector created upon cloning of citZ, icl, and aldA1 into pIPL12 is referred to as pMEG042 herein (FIG. 2B).

TABLE 2

Oligos used to construct pMEG042 expression vector.

| SEQ ID NO | Name | Sequence |
|---|---|---|
| 69 | pIPL12-bb-F | CACACCAGGTCTCAAACCATGGAGATCTCGAGG CCTG |
| 70 | pIPL12-bb-R | CACACCAGGTCTCACATATGATAAGAAGACTCT TGGC |
| 71 | citZ_Bsl-F | CACACCAGGTCTCACATATGACAGCAACAAGGG GCC |
| 72 | citZ_Bsl-R | CACACCAGGTCTCAATTGTAACACCTCCTTAAT TAGTTATGCTCTTTCTTCTATAGGTACAAATTT TTG |
| 73 | Icl_Ec-F | CACACCAGGTCTCACAATGAAAACAAGAACTCA ACAAATAG |
| 74 | Icl_Ec-R | CACACCAGGTCTCAGTGTTCCTCCTATGTGTTC TTAAAATTGAGATTCTTCAGTTGAACCTG |
| 75 | aldA1_Go-F | CACACCAGGTCTCAACACATATGACTGAAAAAA ATAATTTATTCATAAATGGATC |
| 76 | aldA1_Go-R | CACACCAGGTCTCAGGTTATGCATTTAGATATA TTGTTTTTGTCTGTACG |

The pMEG042 construct was transformed into *C. autoethanogenum* via conjugation. The expression vector was first introduced into the conjugative donor strain, *E. coli* HB101+R702 (CA434) (Williams et al. 1990) (the donor), using standard heat shock transformation. Donor cells were recovered in SOC media at 37° C. for 1 h before being plated onto LB media plates comprising 100 µg/mL spectinomycin and 500 µg/mL erythromycin and incubated at 37° C. overnight. The next day, 5 mL LB aliquots comprising 100 µg/mL spectinomycin and 500 µg/mL erythromycin were inoculated with several donor colonies and incubated at 37° C., shaking for approximately 4 h or until the culture was visibly dense but had not yet entered stationary phase. 1.5 mL of the donor culture was harvested by centrifugation at 4000 rpm and 20-25° C. for 2 min, and the supernatant was discarded. The donor cells were gently resuspended in 500 µL sterile PBS buffer and centrifuged at 4000 rpm for 2 min, and the PBS supernatant was discarded.

The pellet was introduced into an anaerobic chamber and gently resuspended in 200 µL during late exponential phase of a *C. autoethanogenum* culture (the recipient). *C. autoethanogenum* DSM10061 and DSM23693 (a derivate of DSM10061) were sourced from DSMZ (The German Collection of Microorganisms and Cell Cultures, Inhoffenstraße 7 B, 38124 Braunschweig, Germany). Strains were grown at 37° C. in PETC medium (See U.S. Pat. No. 9,738,875) at pH 5.6 using standard anaerobic techniques (Hungate 1969; Wolfe 1971).

The conjugation mixture (the mix of donor and recipient cells) was spotted onto PETC-MES+fructose agar plates and left to dry. When the spots were no longer visibly wet, the plates were introduced into a pressure jar, pressurized with syngas (50% CO, 10% $N_2$, 30% $CO_2$, 10% $H_2$) to 25-30 psi, and incubated at 37° C. for ~24 h. The conjugation mixture was then removed from the plates by gentle scraping using a 10 µL inoculation loop. The removed mixture was suspended in 200-300 µL PETC media. 100 µL aliquots of the conjugation mixture were plated onto PETC media agar plates supplemented 5 μg/mL clarithromycin to select for transformants bearing the plasmid.

Figure 3A:
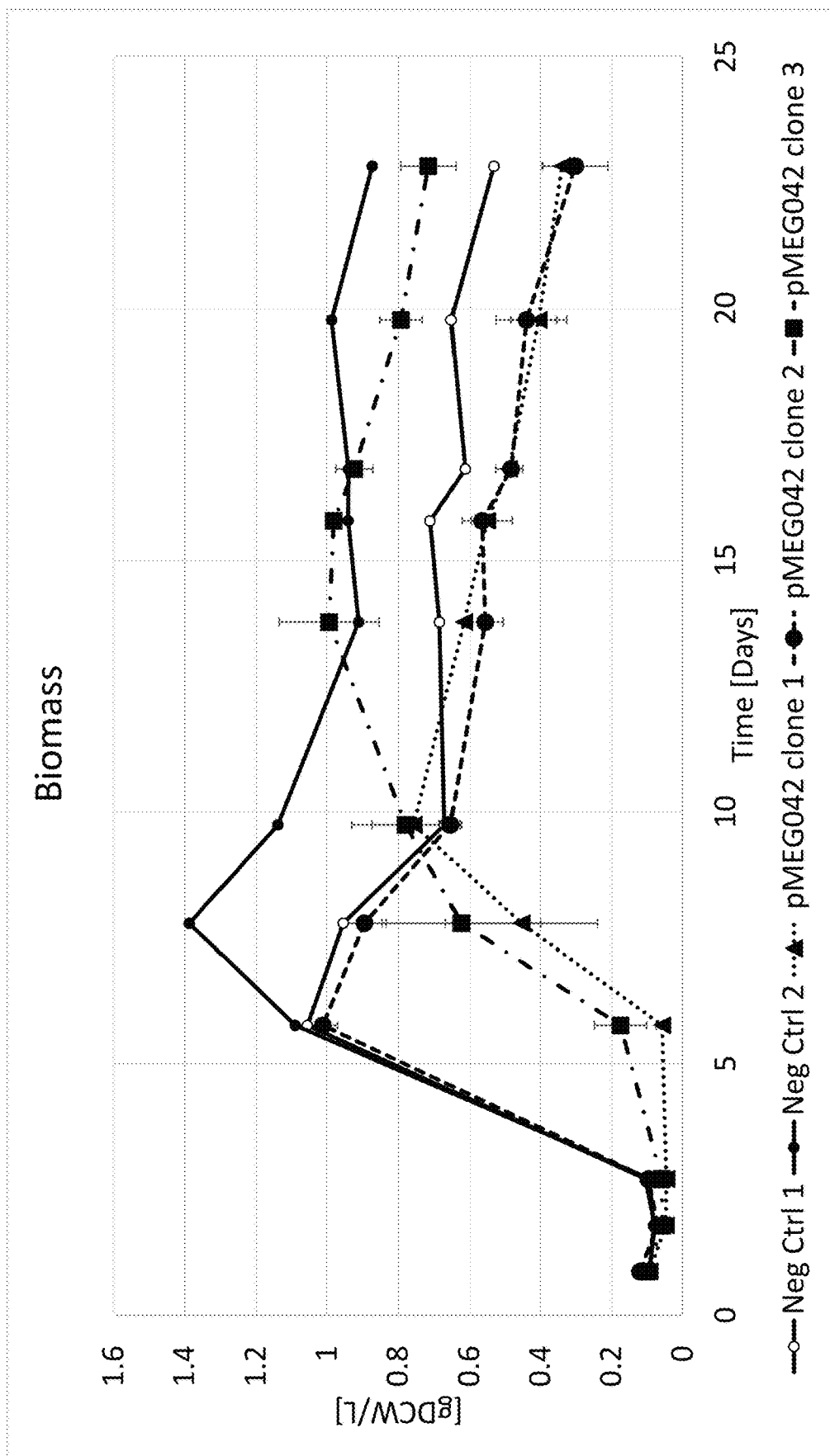
FIG. 3A shows biomass levels (g dry cell weight/L) of *C. autoethanogenum* expressing pMEG042 (clones 1-3) or *C. autoethanogenum* wild-type (Neg Ctrl 1 or Neg Ctrl 2).
Figure 3B:
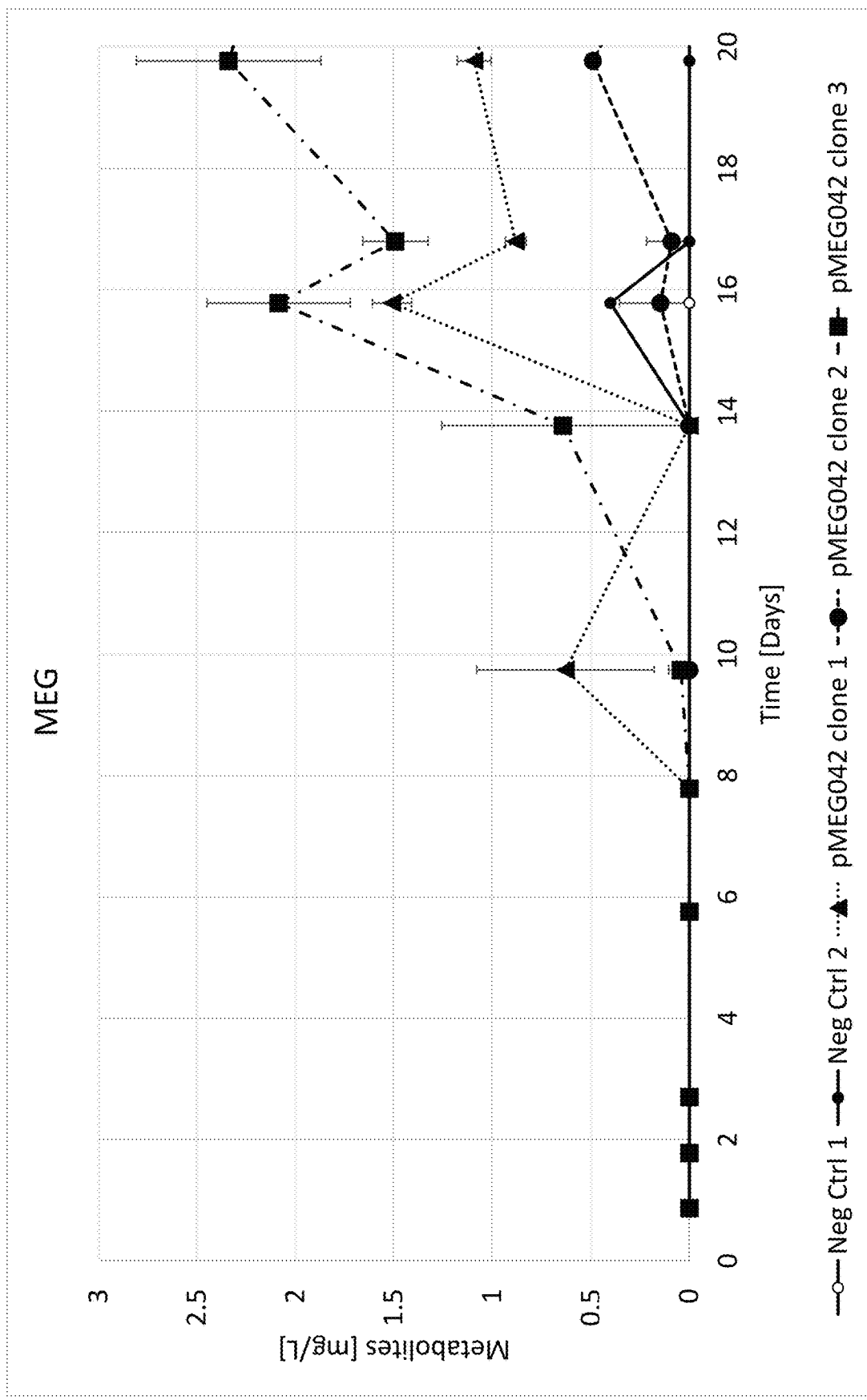
FIG. 3B shows ethylene glycol produced over time in *C. autoethanogenum* growing autotrophically and carrying expression vector pMEG042, as compared to the wild-type (Neg Ctrl 1 or Neg Ctrl 2).

Three distinct colonies of *C. autoethanogenum* bearing the pMEG042 plasmid were inoculated into 2 mL of PETC-MES media with 5 μg/mL clarithromycin and grown autotrophically at 37° C. with 50% CO, 10% $N_2$, 30% $CO_2$, 10% $H_2$ and 100 rpm orbital shaking with for three days. Cultures were diluted to $OD_{600}$ of 0.05 in 10 mL PETC-MES medium with 5 μg/mL clarithromycin in serum bottles and grown autotrophically at 37° C. with 50% CO, 10% $N_2$, 30% $CO_2$, 10% $H_2$ and 100 rpm orbital shaking for up to 20 days, sampling daily to measure biomass and metabolites (FIGS. 3A and 3B). Production of ethylene glycol was measured using gas chromatography mass spectrometry (GC-MS), and other metabolites were measured using high-performance liquid chromatography (HPLC), as described below.

Ethylene glycol concentrations were measured with a Thermo Scientific™ ISQ LT GCMS equipped an Agilent™ VF-WAXms column (15 m×0.25 μm×0.25 μm) and RSH autosampler. Samples were prepared by diluting 200 μL of broth with 200 μL of methanol. The samples were vortexed then centrifuged for 3 min at 14,000 rpm; 200 μL of the supernatant was transferred to a glass vial with insert. Samples were transferred to an autosampler for analysis using a 1.0 μL injection, a split ratio of 5 to 1, and an inlet temperature of 240° C. Chromatography was performed with an oven program of 80° C. with a 0.5 min hold to a ramp of 10° C./min to 150° C. to a ramp of 25° C./min to 220° C. with a 3 min final hold. The column flow rate was 4.0 mL/min with a 0.5 min hold then dropping to 1.5 ml/min at a rate of 100 ml/min/min using helium as the carrier gas. The MS ion source was kept at 260° C. with the transfer line set at 240° C. Quantitation was performed using a linear external standard calibration using 33.0 m/z as the quantitation peak and 31.0+62.0 m/z as the confirming peaks.

Ethanol, acetate, 2,3-butanediol, glyoxylate, and glycolate concentrations were measured by HPLC on an Agilent™ 1260 Infinity LC with Refractive Index (RI) detection at 35° C. Samples were prepared by heating for 5 min at 80° C., followed by a 3 min centrifugation at 14,000 rpm; the supernatant was transferred to a glass vial for analysis. Separation was carried out with a 10 μL injection on to a Phenomenex Rezex™ ROA-Organic Acid H+ (8%) column (300 mm×7.8 mm×8 μm) at 0.7 mL/min and 35° C. under isocratic conditions, using 5 mM sulphuric acid mobile phase.

Figure 3C:
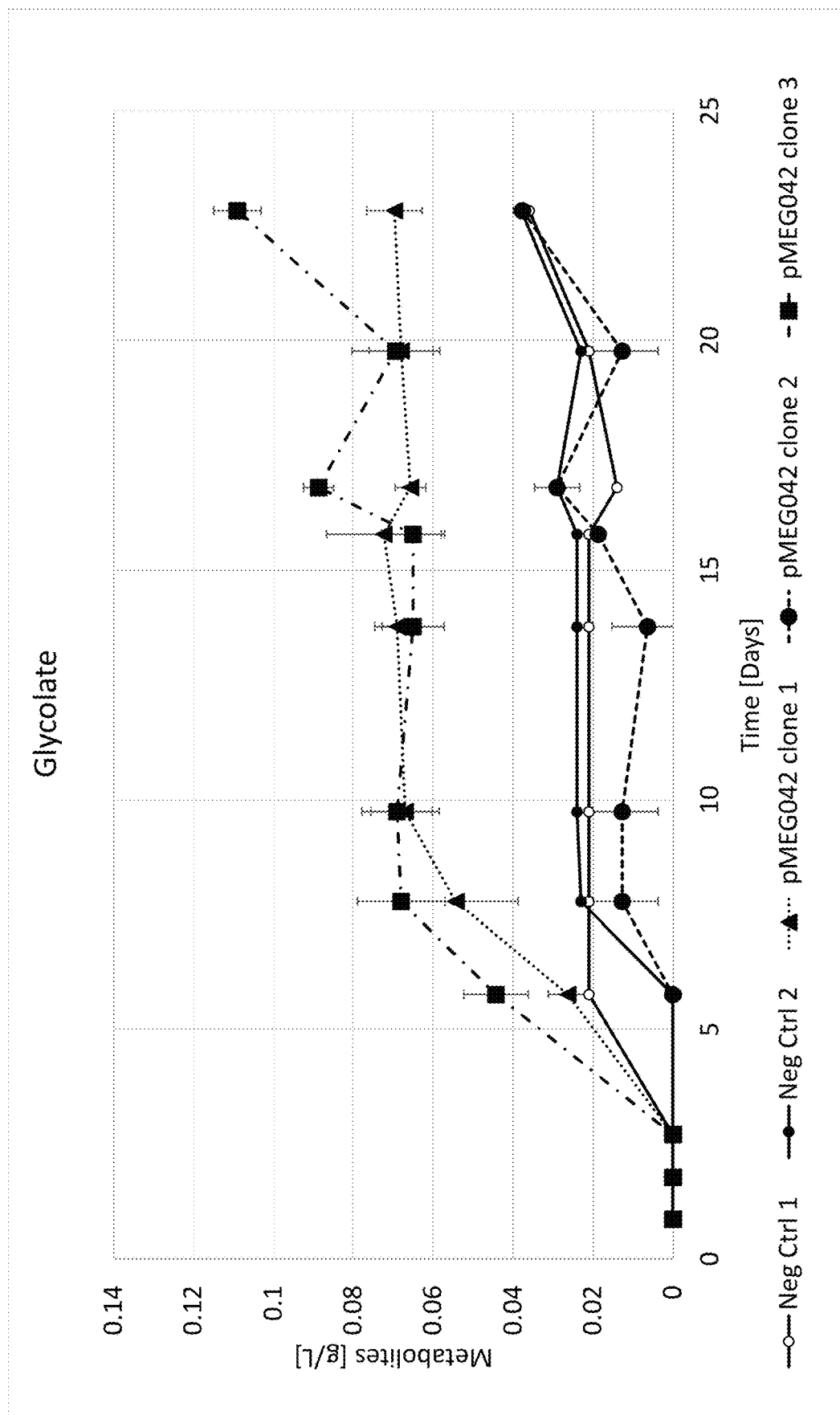
FIG. 3C shows glycolate produced over time in *C. autoethanogenum* growing autotrophically and carrying expression vector pMEG042. See Example 1.

After approximately 3 days of autotrophic growth, the ethylene glycol precursor glycolate was observed, and after 10 days, production of ethylene glycol was observed (FIG. 3B). Glycolate produced over time in *C. autoethanogenum* growing autotrophically and carrying expression vector pMEG042 (FIG. 3C).

Example 2: Construction of Heterologous Expression Vector Comprising *S. thiotaurini* Alanine-Glyoxylate Aminotransferase and *P. fluorescens* Aldehyde Dehydrogenase for Production of Ethylene Glycol from CO and/or $CO_2$ and $H_2$ in *C. autoethanogenum*

Figure 2C:
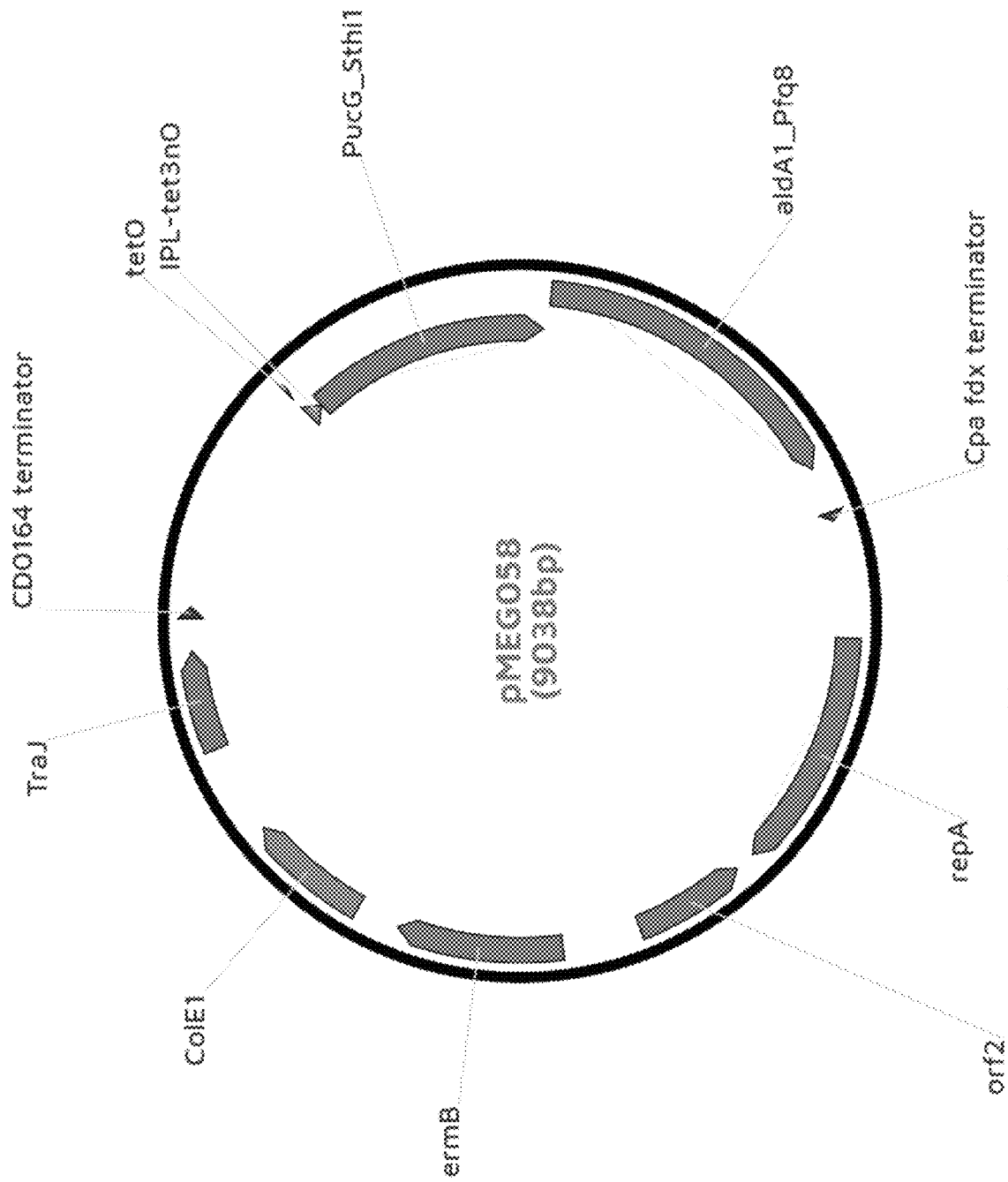

Genes coding for an alanine-glyoxylate aminotransferase from *S. thiotaurini* (pucG; SEQ ID NOs: 15-16) and aldehyde dehydrogenase from *P. fluorescens* Q8r1-96 (aldA1; SEQ ID NOs: 57-58) were codon-adapted and synthesized for expression in *C. autoethanogenum*. The codon-adapted genes were cloned into pIPL12 (FIG. 2A), and the resulting expression vector, pMEG058, was introduced into *C. autoethanogenum*, as described in Example 1. See FIG. 2C.

TABLE 3

Oligos used to construct pMEG058 expression vector.

| SEQ ID NO | Name | Sequence |
|---|---|---|
| 69 | pIPL12-bb-F | CACACCAGGTCTCAAACCATGGAGATCTCGAGGCCTG |
| 70 | pIPL12-bb-R | CACACCAGGTCTCACATATGATAAGAAGACTCTTGGC |
| 77 | PucG_Sthi1-F | CACACCAGGTCTCACATATGCAATTTAGGCCTTTTAATCCACCA |
| 78 | PucG_Sthi1-R | CACACCAGGTCTCAGTGTTCCTCCTATGTGTTCTTATGCTTGCGCAAGTGCCT |
| 79 | aldA1_Pfq8-F | CACACCAGGTCTCAACACATATGTCTTCAGTGCCTGTATTCCAG |
| 80 | aldA1_Pfq8-R | CACACCAGGTCTCAGGTTAAGACTGGAGATATACTGCATGAG |

Figure 4A:
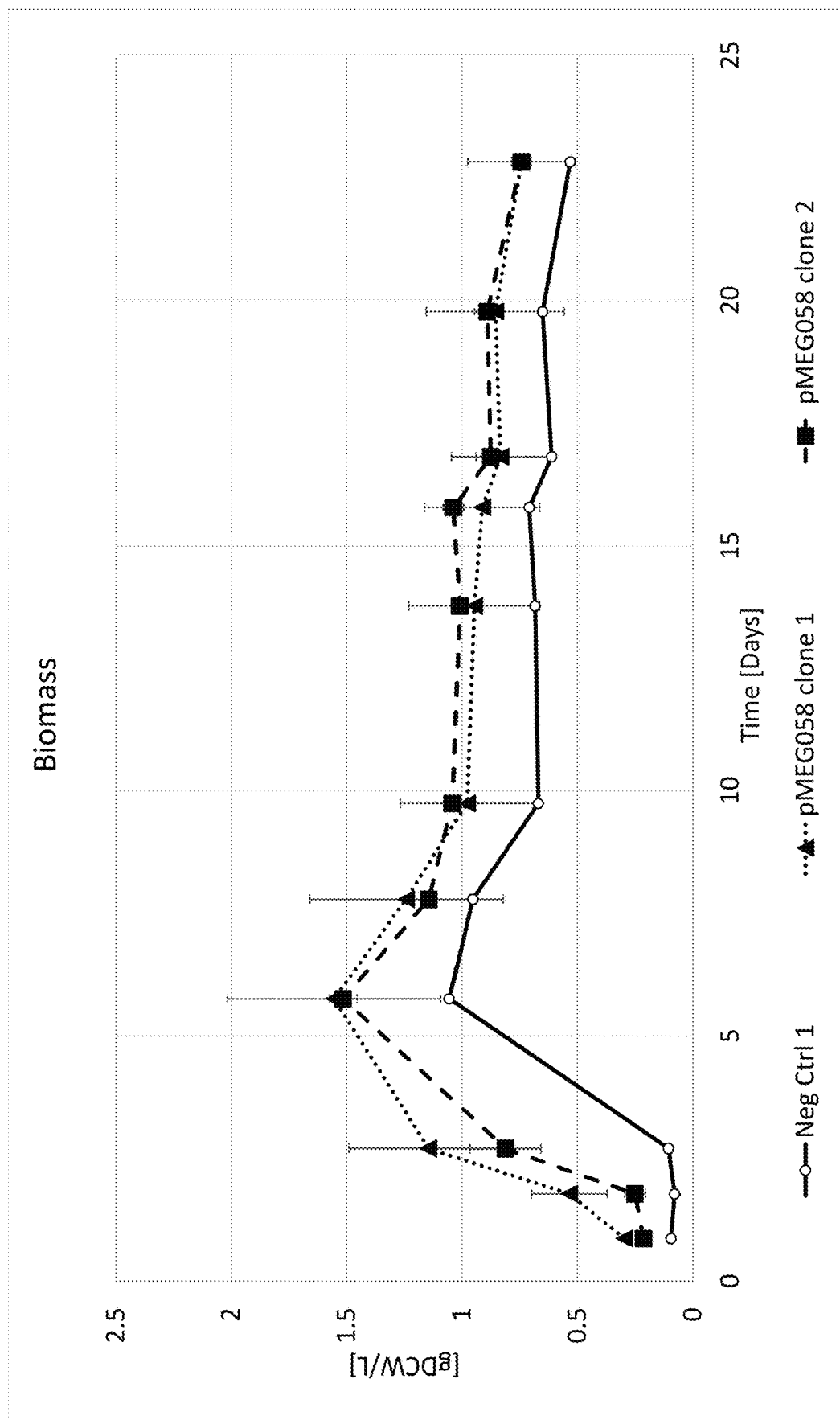
FIG. 4A shows biomass levels (g dry cell weight/L) of *C. autoethanogenum* expressing pMEG058 (clones 1-2) or *C. autoethanogenum* wild-type (Neg Ctrl 1).
Figure 4B:
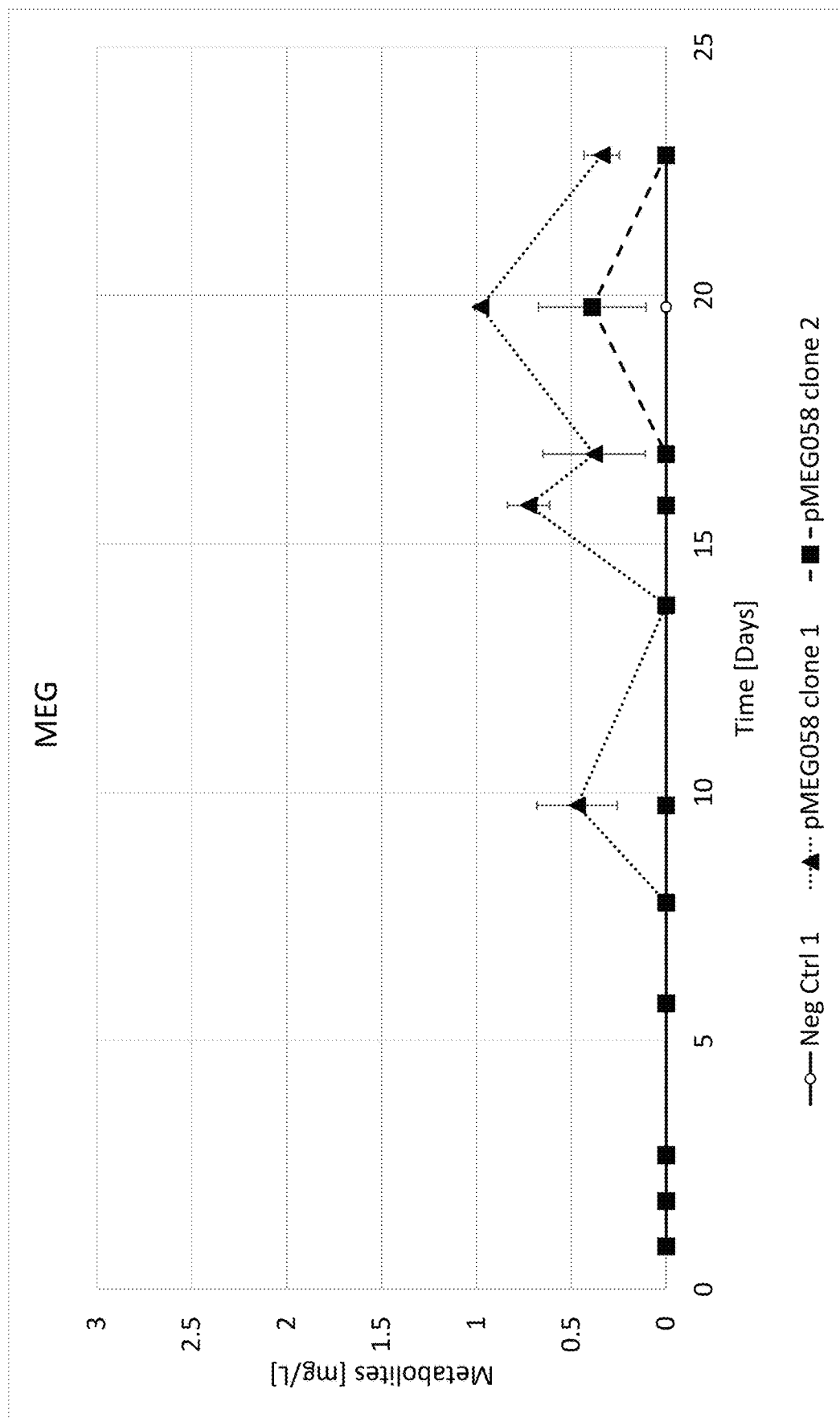
FIG. 4B shows ethylene glycol produced over time in *C. autoethanogenum* growing autotrophically and carrying expression vector pMEG058, as compared to the wild-type (Neg Ctrl 1). See Example 2.

Two distinct colonies of *C. autoethanogenum* bearing the pMEG058 plasmid were inoculated into 2 mL of PETC-MES media with 5 μg/mL clarithromycin and grown autotrophically, as described in Example 1. See FIG. 4A. After approximately 3 days of autotrophic growth, glycolate was observed, and after 8 days production of ethylene glycol was observed (FIG. 4B).

Example 3: Construction of Heterologous Expression Vector Comprising *S. thiotaurini* Alanine-Glyoxylate Aminotransferase and *G. oxydans* Glycolaldehyde Dehydrogenase for Production of Ethylene Glycol from CO and/or $CO_2$ and $H_2$ in *C. autoethanogenum*

Figure 2D:
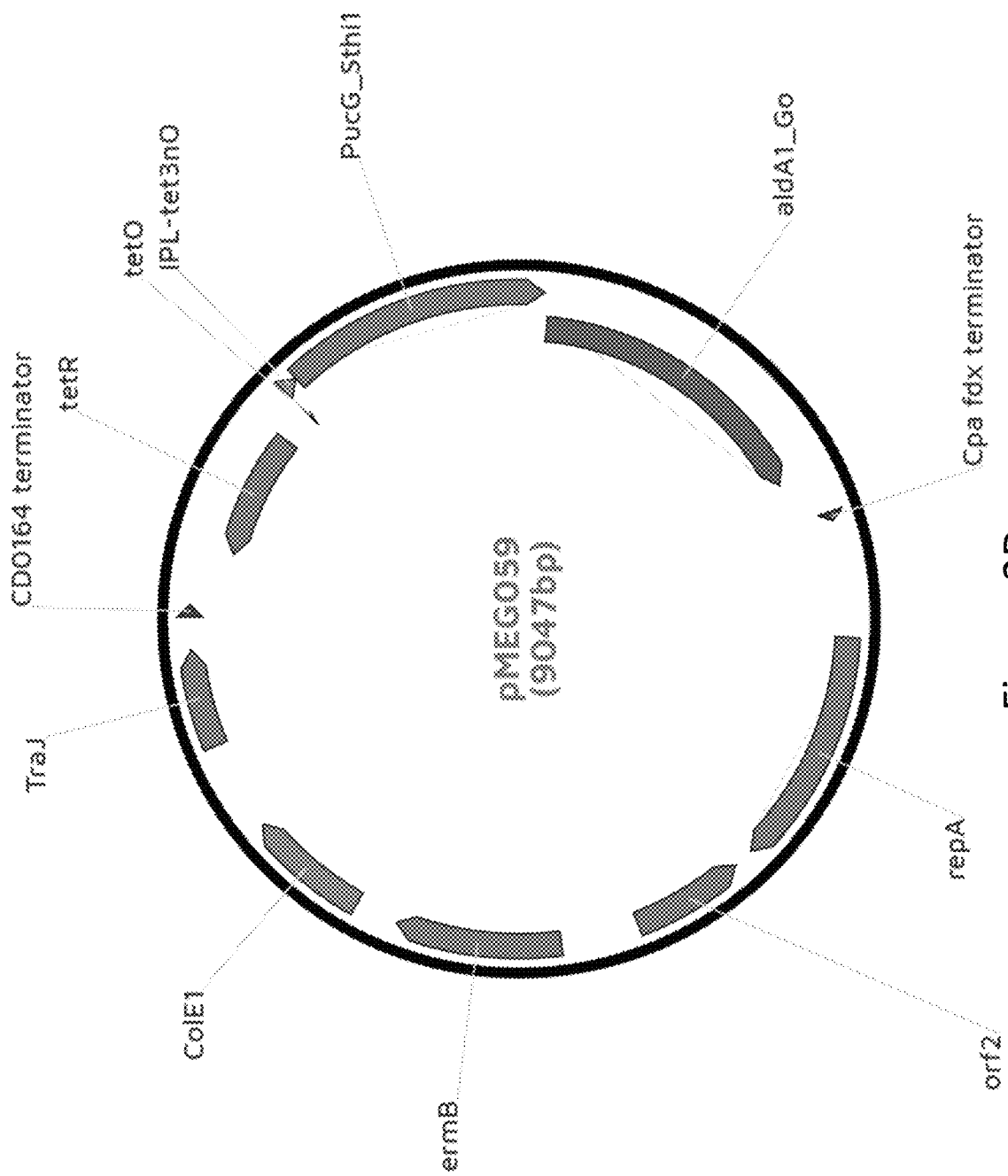

Genes coding for an alanine-glyoxylate aminotransferase from *S. thiotaurini* (pucG; SEQ ID NOs: 15-16) and glycolaldehyde dehydrogenase from *G. oxydans* (aldA1; SEQ ID NOs: 55-56) were codon-adapted and synthesized for expression in *C. autoethanogenum*. The codon-adapted genes were cloned into pIPL12 (FIG. 2A), and the resulting expression vector, pMEG059, was introduced into *C. autoethanogenum*, as described in Example 1. See FIG. 2D.

TABLE 4

Oligos used to construct pMEG059 expression vector.

| SEQ ID NO | Name | Sequence |
|---|---|---|
| 69 | pIPL12-bb-F | CACACCAGGTCTCAAACCATGGAGATCTCGAGGCCTG |
| 70 | pIPL12-bb-R | CACACCAGGTCTCACATATGATAAGAAGACTCTTGGC |
| 77 | PucG_Sthi1-F | CACACCAGGTCTCACATATGCAATTTAGGCCTTTTAATCCACCA |
| 78 | PucG_Sthi1-R | CACACCAGGTCTCAGTGTTCCTCCTATGTGTTCTTATGCTTGCGCAAGTGCCT |

TABLE 4-continued

Oligos used to construct pMEG059 expression vector.

| SEQ ID NO | Name | Sequence |
|---|---|---|
| 75 | aldA1_Go-F | CACACCAGGTCTCAACACATATGACTGAAAAAAATAATTTATTCATAAATGGATC |
| 76 | aldA1_Go-R | CACACCAGGTCTCAGGTTATGCATTTAGATATATTGTTTTTGTCTGTACG |

Figure 5A:
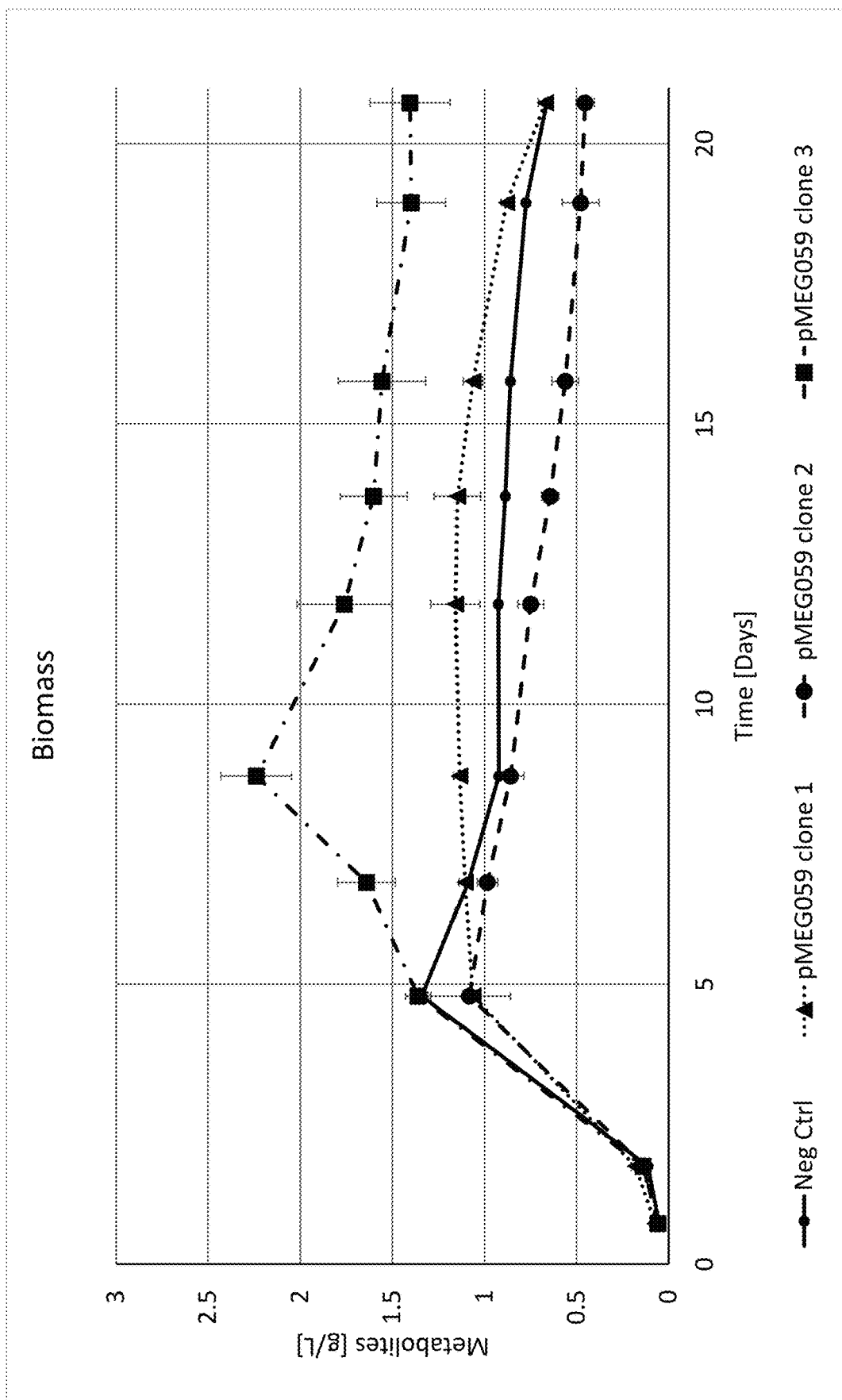
FIG. 5A shows biomass levels (g dry cell weight/L) of *C. autoethanogenum* expressing pMEG059 (clones 1-3) or *C. autoethanogenum* wild-type (Neg Ctrl).
Figure 5B:
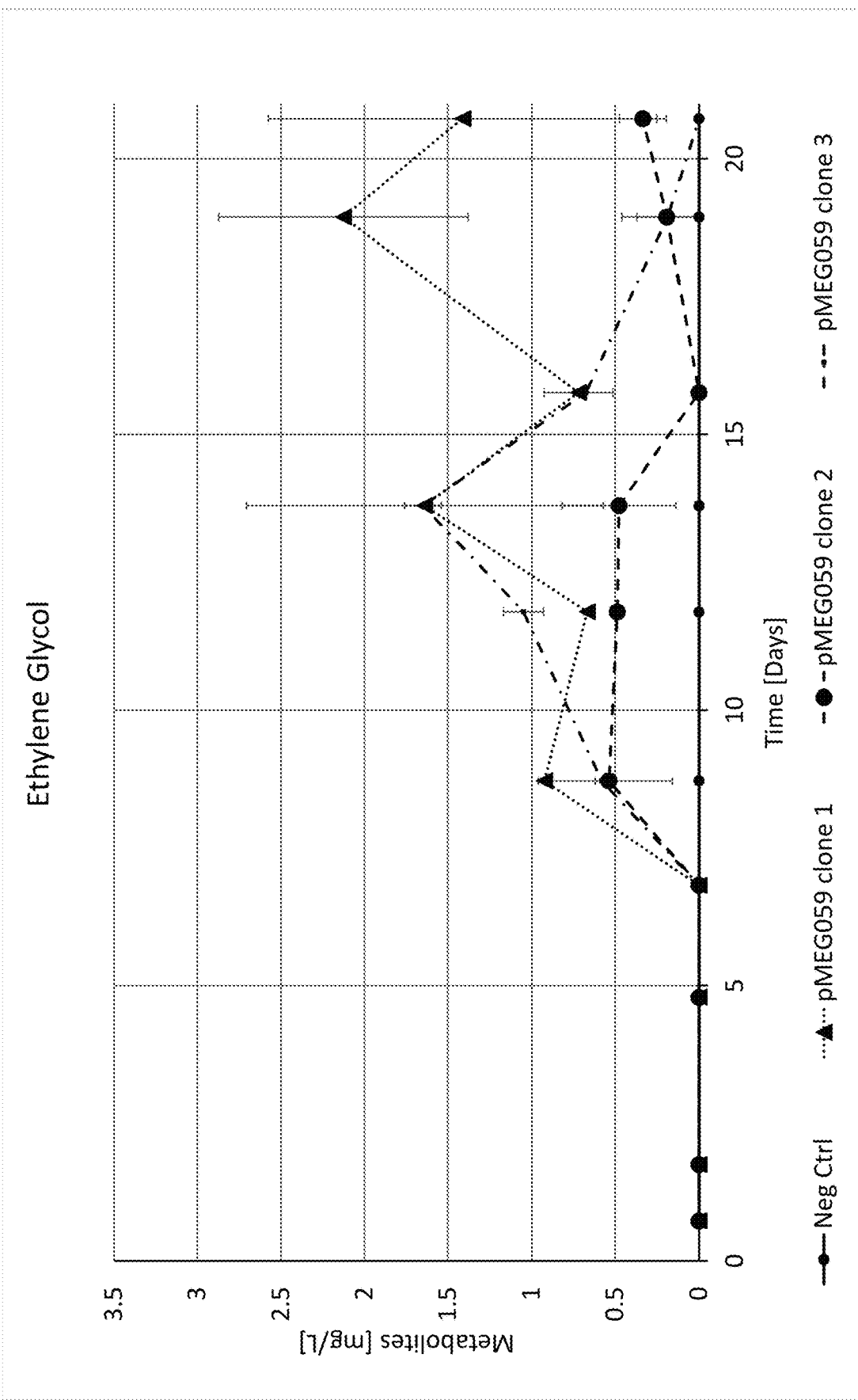
FIG. 5B shows ethylene glycol produced over time in *C. autoethanogenum* growing autotrophically and carrying expression vector pMEG059, as compared to the wild-type (Neg Ctrl). See Example 3.

Two distinct colonies of *C. autoethanogenum* bearing the pMEG059 plasmid were inoculated into 2 mL of PETC-MES medium with 5 μg/mL clarithromycin and grown autotrophically, as described in Example 1. See FIG. 5A. After approximately 3 days of autotrophic growth, glycolate was observed, and after 10 days, production of ethylene glycol was observed (FIG. 5B).

Example 4: Construction of Heterologous Expression Vector Comprising Alanine-Glyoxylate Aminotransferase and Aldehyde Dehydrogenase for Production of Ethylene Glycol from CO and/or $CO_2$ and $H_2$ in *C. autoethanogenum*

Figure 2E:
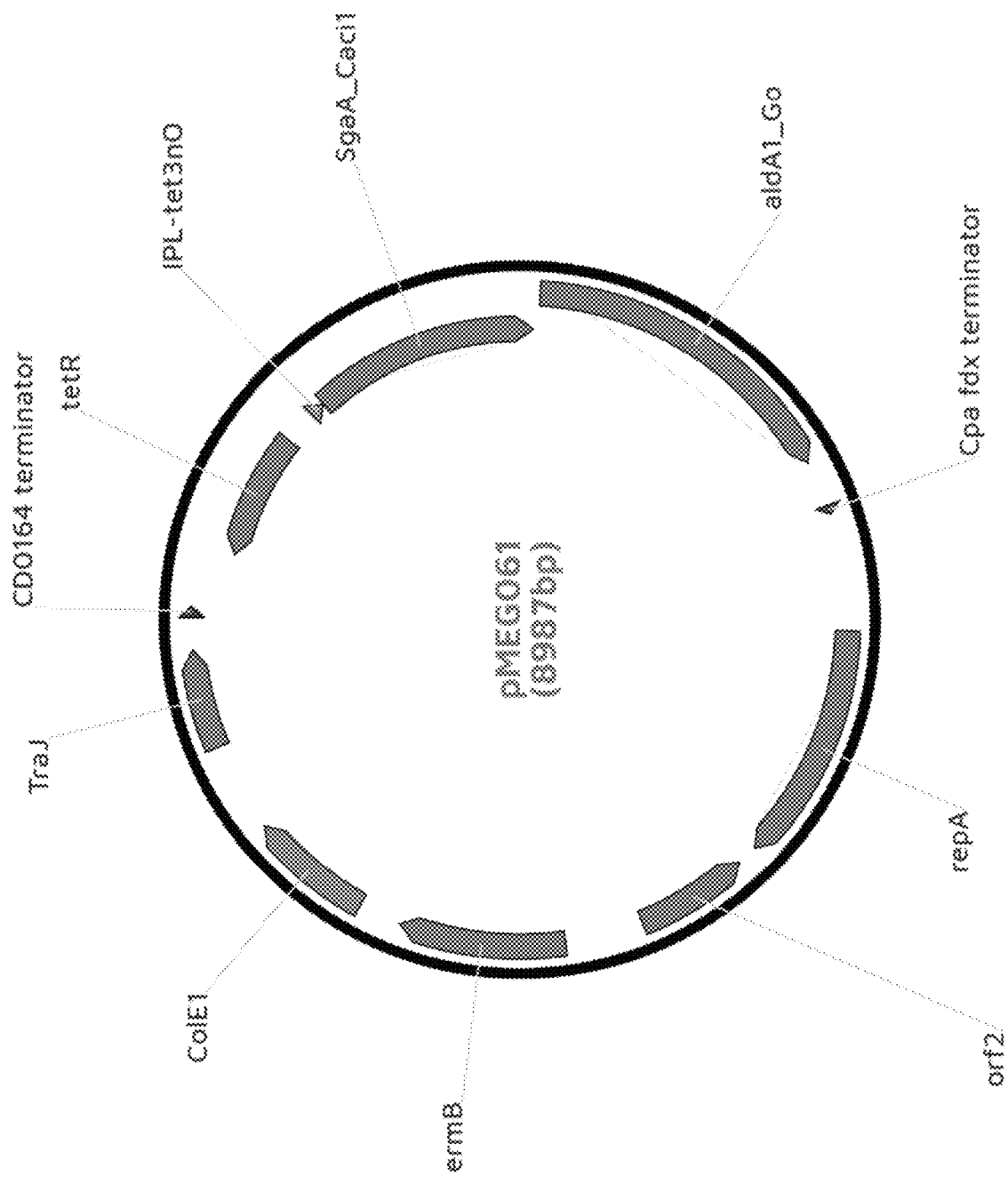

Genes coding for class V aminotransferase from *C. acidurici* (SgA; SEQ ID NOs: 19, 20) and aldehyde dehydrogenase from *P. fluorescens* Q8r1-96 (aldA1; SEQ ID NOs: 57-58) were codon-adapted and synthesized for expression in *C. autoethanogenum*. The codon-adapted genes were cloned into pIPL12 (FIG. 2A), and the resulting vector, pMEG061, was introduced into *C. autoethanogenum*, as described in Example 1. See FIG. 2E.

TABLE 5

Oligos used to construct pMEG061 expression vector.

| SEQ ID NO | Name | Sequence |
|---|---|---|
| 69 | pIPL12-bb-F | CACACCAGGTCTCAAACCATGGAGATCTCGAGGCCTG |
| 70 | pIPL12-bb-R | CACACCAGGTCTCACATATGATAAGAAGACTCTTGGC |
| 81 | SgaA_Caci1-F | CACACCAGGTCTCACATATGAGAACTCCATTTATTATGAC |
| 82 | SgaA_Caci1-R | CACACCAGGTCTCAGTGTTCCTCCTATGTGTTCCTAATCTACAAAGTGCTTG |
| 79 | aldA1_Pfq8-F | CACACCAGGTCTCAACACATATGTCTTCAGTGCCTGTATTCCAG |
| 80 | aldA1_Pfq8-R | CACACCAGGTCTCAGGTTAAGACTGGAGATATACTGCATGAG |

Figure 6A:
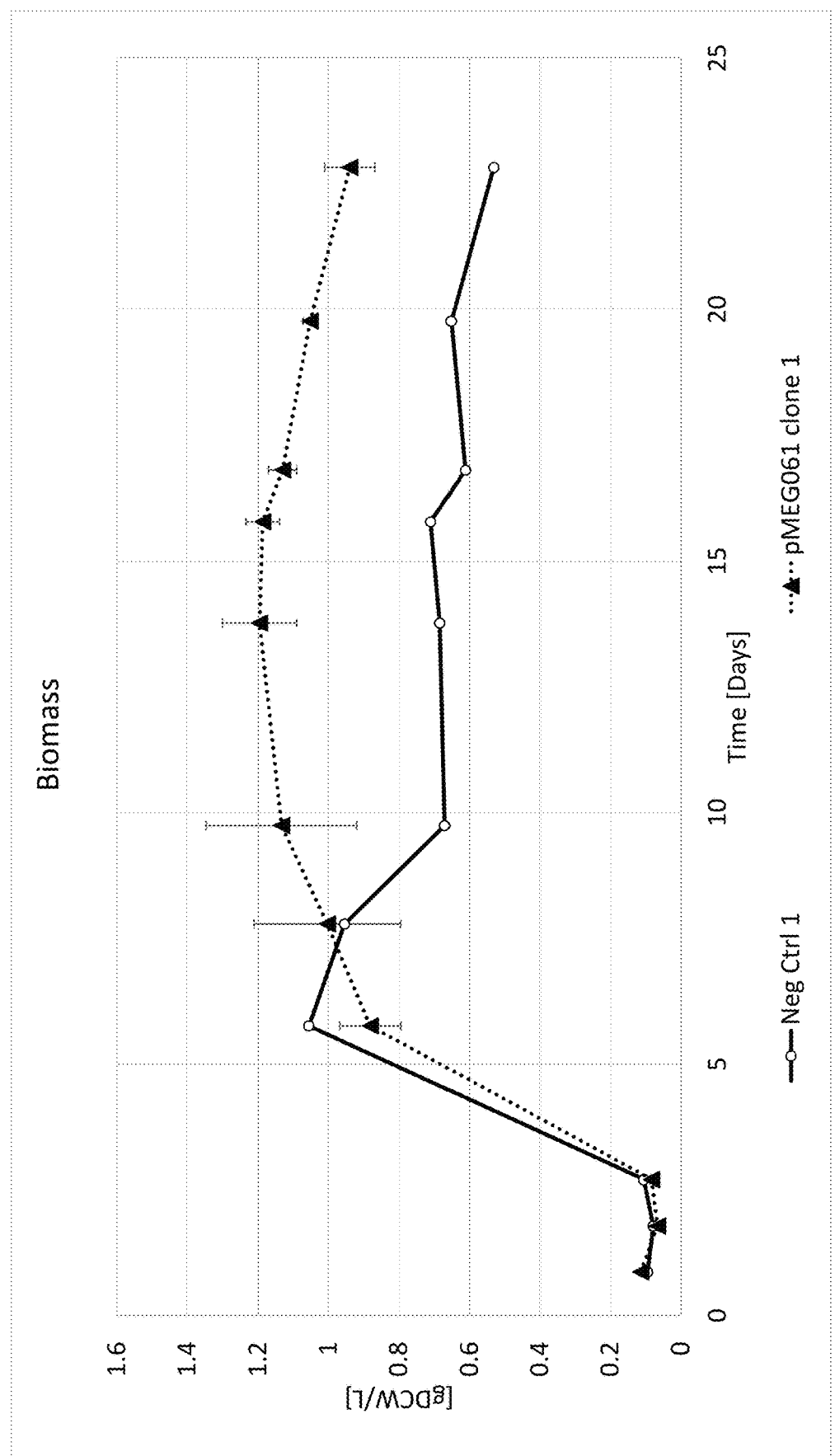
FIG. 6A shows biomass levels (g dry cell weight/L) of *C. autoethanogenum* expressing pMEG061 (clones 1) or *C. autoethanogenum* wild-type (Neg Ctrl 1).
Figure 6B:
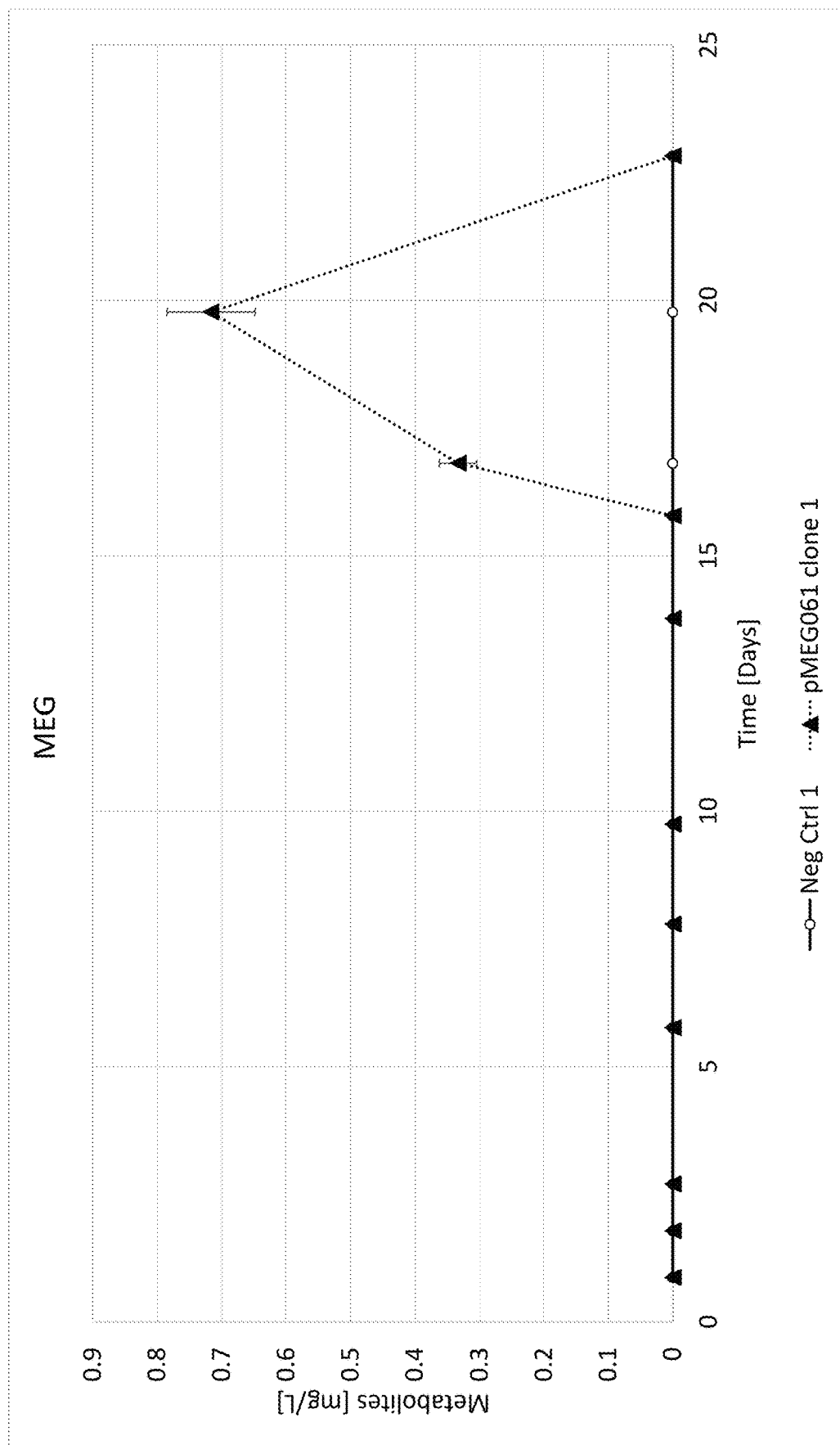
FIG. 6B shows ethylene glycol produced over time in *C. autoethanogenum* growing autotrophically and carrying expression vector pMEG061, as compared to the wild-type (Neg Ctrl 1). See Example 4.

Three distinct colonies of *C. autoethanogenum* bearing the pMEG061 plasmid were inoculated into 2 mL of PETC-MES medium with 5 μg/mL clarithromycin and grown autotrophically, as described in Example 1. See FIG. 6A. After approximately 3 days of autotrophic growth, glycolate was observed, and after 16 days, production of ethylene glycol was observed (FIG. 6B).

Example 5: Modeling of Maximum Yields of Different Routes to Ethylene Glycol

A genome-scale metabolic model of *Clostridium autoethanogenum* like the one described by Marcellin, *Green Chem*, 18: 3020-3028, 2016 was utilized to predict maximum yields of different routes to ethylene glycol. Heterologous metabolic reactions were added to the wild type *Clostridium autoethanogenum* model structure to represent the incorporation of the non-native compound production pathway. Although the model used for the experimental work described herein is based on *Clostridium autoethanogenum*, the results can reasonably be expected to apply to other Wood-Ljungdahl microorganisms as well, given similarities in metabolism.

Ethylene glycol production was simulated using constraint-based computational modeling techniques flux balance analysis (FBA) and linear minimization of metabolic adjustment (LMOMA) (Maia, *Proceedings of the Genetic and Evolutionary Computation Conference Companion on—GECCO '17*, New York, New York, ACM Press, 1661-1668, 2017) using cobrapy version 0.8.2 (Ebrahim., COBRApy: COnstraints-Based Reconstruction and Analysis for Python, *BMC Syst Biol*, 7: 74, 2013), with optlang version 1.2.3 (Jensen, Optlang: An Algebraic Modeling Language for Mathematical Optimization," The Journal of Open Source Software, 2, doi:10.21105/joss.00139, 2017) as the solver interface and Gurobi Optimizer version 7.0.2 as the optimization solver.

Modeling revealed a predicted yield of 0.37 mol ethylene glycol/mol CO by the pathways described herein in Examples 1-4. This is more than double the predicted yield by the hypothetical pathways described by Islam et al. *Metab Eng*, 41: 173-181, 2017, which require gluconeogenesis; the highest predicted yields were found to be ~0.0.44 g ethylene glycol/g CO, which equals ~0.0.18 mol ethylene glycol/mol CO.

Example 6: Ethylene Glycol Production and Diol Dehydratase Knockout

Figure 7:
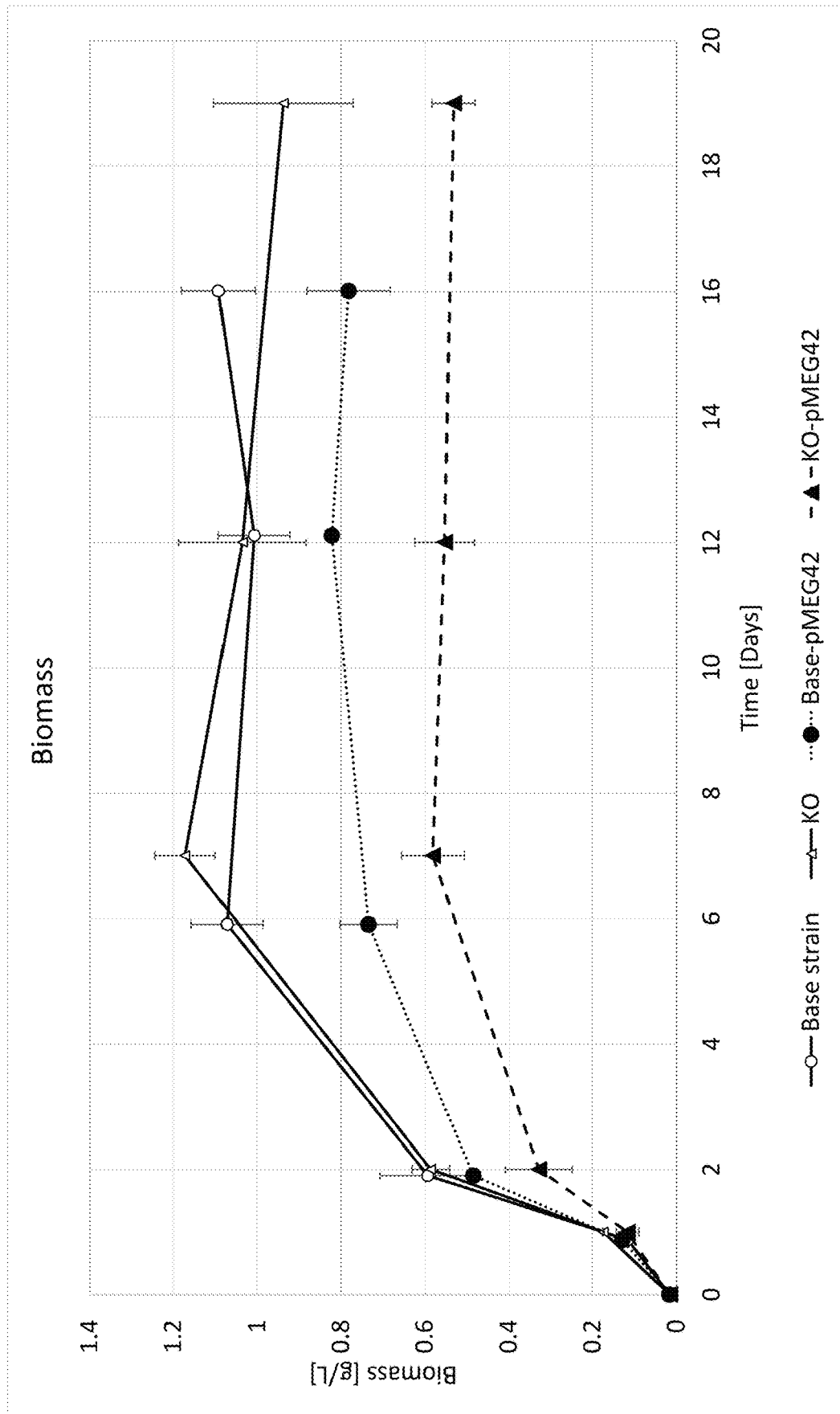
FIG. 7 shows biomass levels (g dry cell weight/L) of two different genotypes of *C. autoethanogenum*: one containing the identified native diol dehydratase (Base), and one with the diol dehydratase gene deleted (KO). Each strain has two variants, one carrying the pMEG042 expression vector, and one carrying no vector (negative control). Values shown are calculated from the average of 3 technical replicates. Error bars show standard deviation.
Figure 8A:
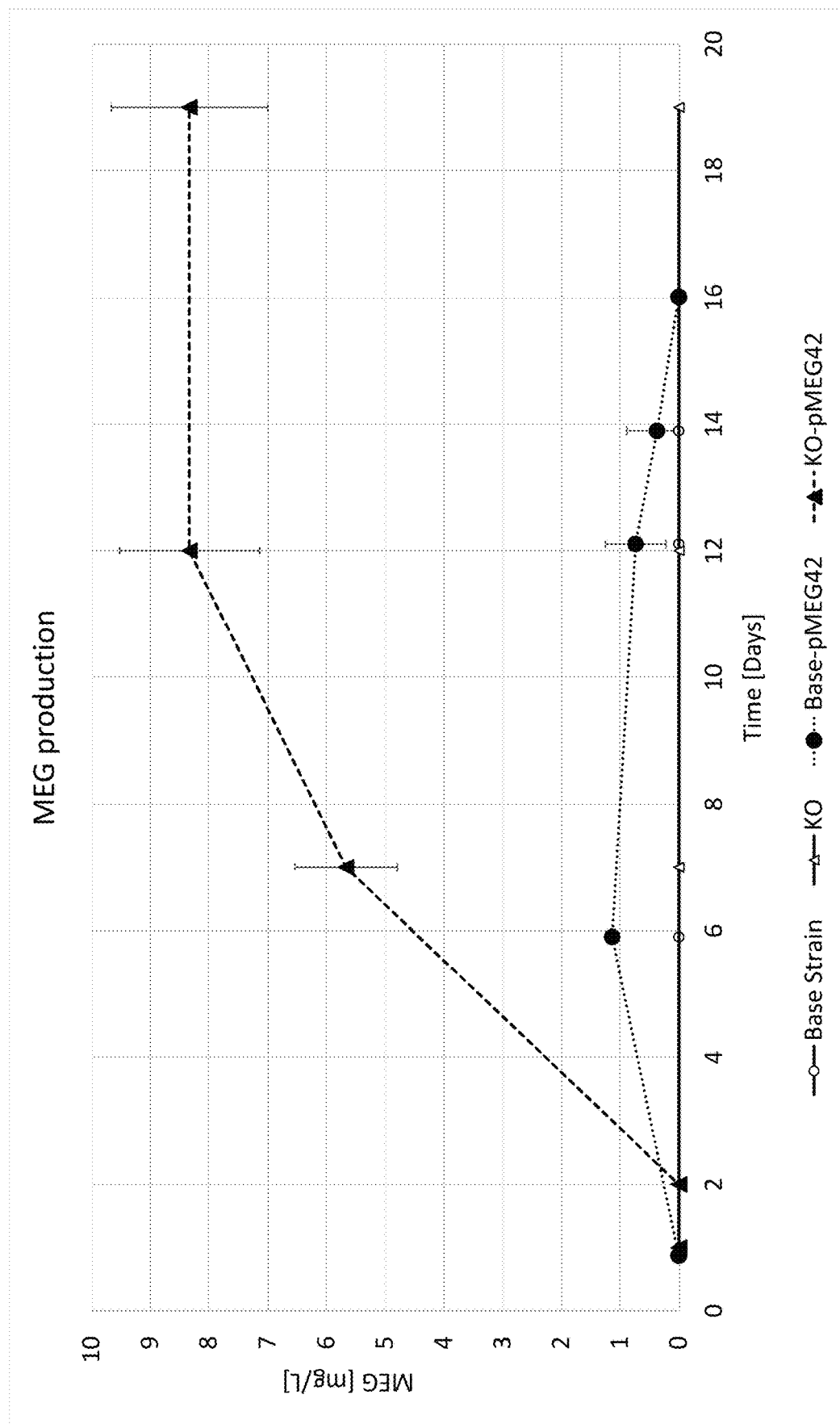
FIG. 8A shows MEG (mg/L) produced over time in two different genotypes of *C. autoethanogenum*: one containing the identified native diol dehydratase (Base), and one with the diol dehydratase gene deleted (KO). Each strain has two variants, one carrying the pMEG042 expression vector, and one carrying no vector (negative control). Values shown are calculated from the average of 3 technical replicates. Error bars show standard deviation.
Figure 8B:
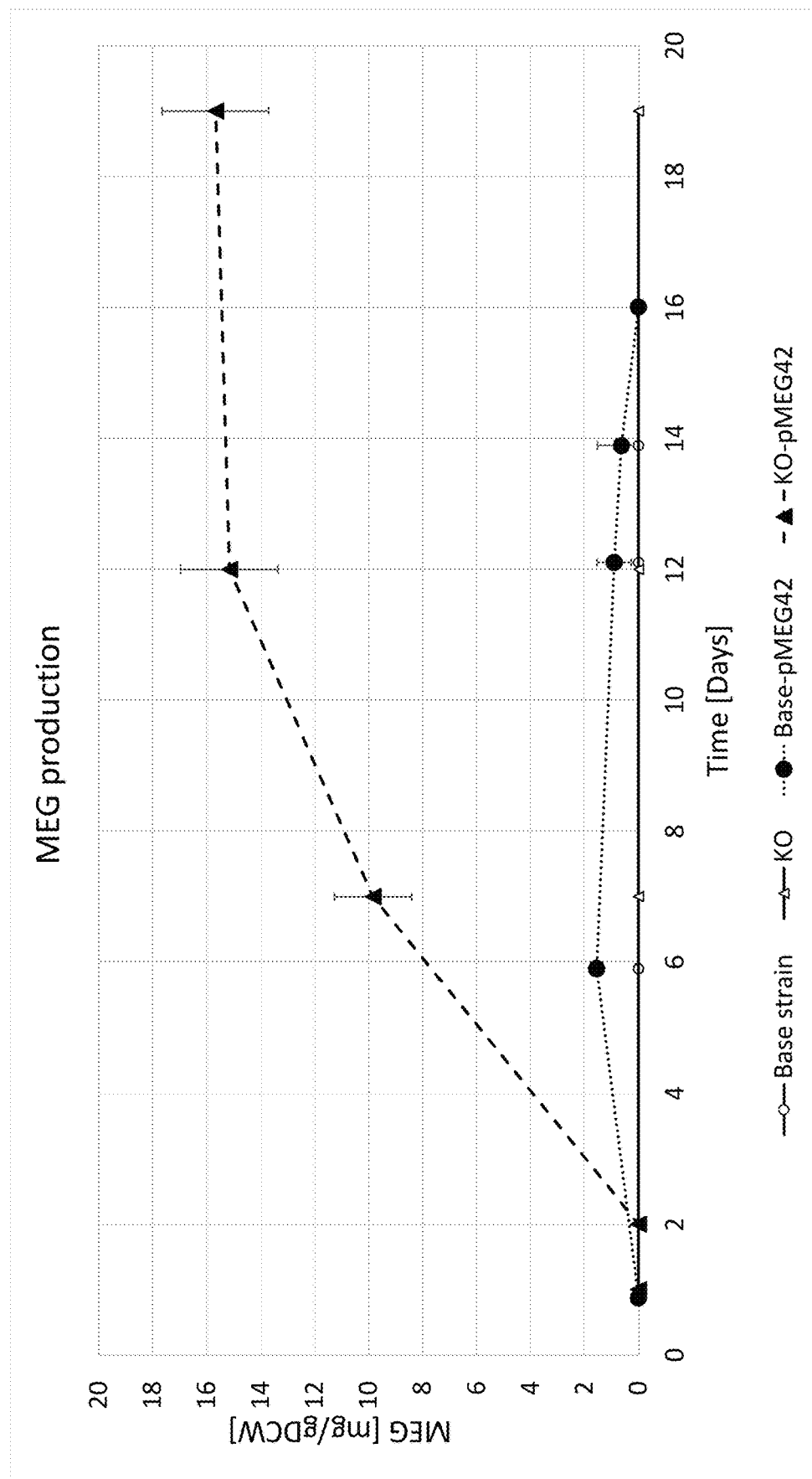
FIG. 8B shows MEG (mg/g dry cell weight) produced over time in different genotypes of *C. autoethanogenum*: one containing the identified native diol dehydratase (Base), and one with the diol dehydratase gene deleted (KO). Each strain has two variants, one carrying the pMEG042 expression vector, and one carrying no vector (negative control). Values shown are calculated from the average of 3 technical replicates. Error bars show standard deviation.

Biomass levels (g dry cell weight/L) of two different genotypes of *C. autoethanogenum*: one containing the identified native diol dehydratase (Base), and one with the diol dehydratase gene deleted (KO). Each strain has two variants, one carrying the pMEG042 expression vector, and one carrying no vector (negative control). Values shown are calculated from the average of 3 technical replicates. See FIG. 7. Ethylene glycol (mg/L) produced over time in two different genotypes of *C. autoethanogenum*: one containing the identified native diol dehydratase (Base), and one with the diol dehydratase gene deleted (KO). Each strain has two variants, one carrying the pMEG042 expression vector, and one carrying no vector (negative control). Values shown are calculated from the average of 3 technical replicates. See FIG. 8A. Ethylene glycol (mg/L/g dry cell weight) produced over time in different genotypes of *C. autoethanogenum*: one containing the identified native diol dehydratase (Base), and one with the diol dehydratase gene deleted (KO). Each strain has two variants, one carrying the pMEG042 expression vector, and one carrying no vector (negative control). Values shown are calculated from the average of 3 technical replicates. See FIG. 8B.

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavour in any country.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. The term "consisting essentially of" limits the scope of a composition, process, or method to the specified materials or steps, or to those that do not materially affect the basic and novel characteristics of the composition, process, or method. The use of the alternative (e.g., "or") should be understood to mean either one, both, or any combination thereof of the alternatives. As used herein, the term "about" means±20% of the indicated range, value, or structure, unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. For example, any concentration range, percentage range, ratio range, integer range, size range, or thickness range is to be understood to include the value of any integer within the recited range and, when appropriate, fractions thereof (such as one tenth and one hundredth of an integer), unless otherwise indicated.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A genetically engineered C1-fixing microorganism capable of producing ethylene glycol or a precursor of ethylene glycol from a gaseous substrate comprising: a disruptive mutation in a gene encoding diol dehydratase.

2. The microorganism of claim 1, wherein the microorganism produces ethylene glycol or the precursor of ethylene glycol through one or more intermediates selected from the group consisting of 5,10-methylenetetrahydrofolate, oxaloacetate, citrate, malate, and glycine.

3. The microorganism of claim 1, wherein the microorganism comprises one or more of:
   a. a nucleic acid encoding a heterologous enzyme capable of converting oxaloacetate to citrate;
   b. a nucleic acid encoding a heterologous enzyme capable of converting glycine to glyoxylate;
   c. a nucleic acid encoding a heterologous enzyme capable of converting iso-citrate to glyoxylate; and
   d. a nucleic acid encoding a heterologous enzyme capable of converting glycolate to glycolaldehyde.

4. The microorganism of claim 3, wherein:
   a. the heterologous enzyme capable of converting oxaloacetate to citrate is a citrate [Si]-synthase having the EC number 2.3.3.1, an ATP citrate synthase having the EC number 2.3.3.8; or a citrate (Re)-synthase having the EC number 2.3.3.3;
   b. the heterologous enzyme capable of converting glycine to glyoxylate is an alanine-glyoxylate transaminase having the EC number 2.6.1.44, a serine-glyoxylate transaminase having the EC number 2.6.1.45, a serine-pyruvate transaminase having the EC number 2.6.1.51, a glycine-oxaloacetate transaminase having the EC number 2.6.1.35, a glycine transaminase having the EC number 2.6.1.4, a glycine dehydrogenase having the EC number 1.4.1.10, an alanine dehydrogenase having the EC number 1.4.1.1, or a glycine dehydrogenase having the EC number 1.4.2.1;
   c. the heterologous enzyme capable of converting iso-citrate to glyoxylate is an isocitrate lyase having the EC number 4.1.3.1; or
   d. the heterologous enzyme capable of converting glycolate to glycolaldehyde is a glycolaldehyde dehydrogenase having the EC number 1.2.1.21, a lactaldehyde dehydrogenase having the EC number 1.2.1.22, a succinate-semialdehyde dehydrogenase having the EC number 1.2.1.24, a 2,5-dioxovalerate dehydrogenase having the EC number 1.2.1.26, an aldehyde dehydrogenase having the EC number 1.2.1.3/4/5, a betaine-aldehyde dehydrogenase having he EC number 1.2.1.8, or an aldehyde ferredoxin oxidoreductase having the EC number 1.2.7.5.

5. The microorganism of claim 3, wherein one or more of the heterologous enzymes are derived from a genus selected from the group consisting of *Bacillus, Clostridium, Escherichia, Gluconobacter, Hyphomicrobium, Lysinibacillus, Paenibacillus, Pseudomonas, Sedimenticola, Sporosarcina, Streptomyces, Thermithiobacillus, Thermotoga, Cupriavidus*, and *Zea*.

6. The microorganism of claim 3, wherein one or more of the heterologous enzymes are codon-optimized for expression in the microorganism.

7. The microorganism of claim 3, wherein the microorganism further comprises one or more of an enzymes capable of converting acetyl-CoA to pyruvate; an enzyme capable of converting pyruvate to oxaloacetate; an enzyme capable of converting pyruvate to malate; an enzyme capable of converting pyruvate to phosphoenolpyruvate; an enzyme capable of converting oxaloacetate to citryl-CoA; an enzyme capable of converting citryl-CoA to citrate; an enzyme capable of converting citrate to aconitate and aconitate to iso-citrate; an enzyme capable of converting phosphoenolpyruvate to oxaloacetate; an enzyme capable of converting phosphoenolpyruvate to 2-phospho-D-glycerate; an enzyme capable of converting 2-phospho-D-glycerate to 3-phospho-D-glycerate; an enzyme capable of converting 3-phospho-D-glycerate to 3-phosphonooxypyruvate; an enzyme capable of converting 3-phosphonooxypyruvate to 3-phospho-L-serine; an enzyme capable of converting 3-phospho-L-serine to serine; an enzyme capable of converting serine to glycine; an enzyme capable of converting 5,10-methylenetetrahydrofolate to glycine; an enzyme capable of converting serine to hydroxypyruvate; an enzyme capable of converting D-glycerate to hydroxypyruvate; an enzyme capable of converting malate to glyoxylate; an enzyme capable of converting glyoxylate to glycolate; an enzyme capable of converting hydroxypyruvate to glycolaldehyde; and an enzyme capable of converting glycolaldehyde to ethylene glycol.

8. The microorganism of claim 3, wherein the microorganism overexpresses:
  a. the heterologous enzyme capable of converting oxaloacetate to citrate;
  b. the heterologous enzyme capable of converting glycine to glyoxylate; and/or
  c. the heterologous enzyme capable of converting glycolate to glycolaldehyde.

9. The microorganism of claim 7, wherein the microorganism overexpresses:
  a. the enzyme capable of converting pyruvate to oxaloacetate;
  b. the enzyme capable of converting citrate to aconitate and aconitate to iso-citrate;
  c. the enzyme capable of converting phosphoenolpyruvate to oxaloacetate;
  d. the enzyme capable of converting serine to glycine;
  e. the enzyme capable of converting 5,10-methylenetetrahydrofolate to glycine;
  f. the enzyme capable of converting glyoxylate to glycolate; or
  g. the enzyme capable of converting glycolaldehyde to ethylene glycol.

10. The microorganism of claim 1, wherein the microorganism further comprises a disruptive mutation in one or more of isocitrate dehydrogenase, glycerate dehydrogenase, glycolate dehydrogenase, aldehyde ferredoxin oxidoreductase, and aldehyde dehydrogenase.

11. The microorganism of claim 1, wherein the microorganism is a member of a genus selected from the group consisting of *Acetobacterium, Alkalibaculum, Blautia, Butyribacterium, Clostridium, Cupriavidus, Eubacterium, Moorella, Oxobacter, Sporomusa*, and *Thermoanaerobacter*.

12. The microorganism of claim 1, wherein the microorganism is derived from a parental microorganism selected from the group consisting of *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Cupriavidus necator, Eubacterium limosum, Moorella thermautotrophica, Moorella thermoacetica, Oxobacter pfennigii, Sporomusa ovata, Sporomusa silvacetica, Sporomusa sphaeroides*, and *Thermoanaerobacter kiuvi*.

13. The microorganism of claim 12, wherein the microorganism is derived from a parental bacterium selected from the group consisting of *Clostridium autoethanogenum, Clostridium ljungdahlii*, and *Clostridium ragsdalei*.

14. The microorganism of claim 1, wherein the microorganism comprises a native or heterologous Wood-Ljungdahl pathway.

15. The microorganism of claim 1, wherein the precursor of ethylene glycol is glyoxylate or glycolate.

16. A method of producing ethylene glycol or a precursor of ethylene glycol comprising culturing the microorganism of claim 1 in a nutrient medium in the presence of a gaseous substrate, whereby the microorganism produces ethylene glycol or the precursor of ethylene glycol.

17. The method of claim 16, wherein the gaseous substrate comprises one or more of CO, $CO_2$, and $H_2$.

18. The method of claim 16, wherein the precursor of ethylene glycol is glyoxylate or glycolate.

19. The method of claim 16, further comprising separating ethylene glycol or the precursor of ethylene glycol from the nutrient medium.

20. The method of claim 16, wherein the microorganism further produces one or more of ethanol, 2,3-butanediol, and succinate.

* * * * *